(12) United States Patent
Torii et al.

(10) Patent No.: US 8,497,226 B2
(45) Date of Patent: *Jul. 30, 2013

(54) WATER ABSORBENT AND PRODUCING METHOD OF SAME

(75) Inventors: Kazushi Torii, Himeji (JP); Hirofumi Shibata, Himeji (JP); Taku Iwamura, Himeji (JP); Yoshio Irie, Himeji (JP); Yorimichi Dairoku, Himeji (JP); Yoshiro Mitsukami, Himeji (JP); Sayaka Machida, Himeji (JP)

(73) Assignee: Nippon Shokubai Co., Ltd., Osaka-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/805,685

(22) Filed: Aug. 13, 2010

(65) Prior Publication Data

US 2010/0308263 A1  Dec. 9, 2010

Related U.S. Application Data

(62) Division of application No. 10/572,565, filed as application No. PCT/JP2004/014015 on Sep. 17, 2004, now Pat. No. 7,803,880.

(30) Foreign Application Priority Data

Sep. 19, 2003  (JP) ................................. 2003-329109
Sep. 19, 2003  (JP) ................................. 2003-329110

(51) Int. Cl.
*B01J 20/26* (2006.01)
*C08F 20/06* (2006.01)

(52) U.S. Cl.
USPC ........ 502/402; 525/329.7; 525/418; 523/111; 252/194

(58) Field of Classification Search
USPC . 525/329.7, 418; 523/111; 502/402; 252/194
See application file for complete search history.

(56) References Cited

U.S. PATENT DOCUMENTS

| | | | |
|---|---|---|---|
| 4,771,105 A | 9/1988 | Shirai et al. | |
| 4,973,632 A | 11/1990 | Nagasuna et al. | |
| 5,026,800 A | 6/1991 | Kimura et al. | |
| 5,185,413 A | 2/1993 | Yoshinaga et al. | |
| 5,244,735 A | 9/1993 | Kimura et al. | |
| 5,264,495 A | 11/1993 | Irie et al. | |
| 5,599,335 A | 2/1997 | Goldman et al. | |
| 5,801,238 A | 9/1998 | Tanaka et al. | |
| 6,087,002 A | 7/2000 | Kimura et al. | |
| 6,150,582 A * | 11/2000 | Wada et al. ................... | 604/372 |
| 6,335,406 B1 | 1/2002 | Nagasuna et al. | |
| 6,403,700 B1 | 6/2002 | Dahmen et al. | |
| 6,417,425 B1 | 7/2002 | Whitmore et al. | |
| 6,433,058 B1 | 8/2002 | Weir et al. | |
| 6,448,320 B1 | 9/2002 | Igarashi et al. | |
| 6,605,673 B1 | 8/2003 | Mertens et al. | |
| 6,620,889 B1 | 9/2003 | Mertens et al. | |
| 2001/0025093 A1 | 9/2001 | Ishizaki et al. | |
| 2002/0040095 A1 | 4/2002 | Dairoku et al. | |
| 2002/0127166 A1 | 9/2002 | Bergeron et al. | |
| 2002/0128618 A1 | 9/2002 | Frenz et al. | |
| 2002/0165288 A1 | 11/2002 | Frenz et al. | |
| 2002/0169252 A1 | 11/2002 | Wilson | |
| 2002/0193492 A1 | 12/2002 | Wilson | |
| 2003/0207997 A1 | 11/2003 | Mertens et al. | |
| 2004/0042952 A1 | 3/2004 | Bergeron et al. | |
| 2004/0071966 A1 | 4/2004 | Inger et al. | |
| 2004/0106745 A1 | 6/2004 | Nakashima et al. | |
| 2005/0049379 A1 | 3/2005 | Adachi et al. | |
| 2005/0070071 A1 | 3/2005 | Henley et al. | |
| 2005/0221980 A1 | 10/2005 | Adachi et al. | |
| 2007/0078231 A1 | 4/2007 | Shibata et al. | |
| 2007/0207924 A1 | 9/2007 | Ikeuchi et al. | |
| 2008/0139693 A1 | 6/2008 | Ikeuchi et al. | |

FOREIGN PATENT DOCUMENTS

| | | |
|---|---|---|
| CA | 2 433 044 | 7/2002 |
| EP | 0 668 080 A | 8/1995 |
| EP | 0761241 A2 | 3/1997 |
| EP | 0 837 076 A | 4/1998 |
| EP | 0 937 739 A | 8/1999 |
| EP | 1 130 045 A | 9/2001 |
| EP | 1 153 656 A | 11/2001 |
| JP | 64-056707 A | 3/1989 |
| JP | 2-196802 | 8/1990 |
| JP | 02-255804 | 10/1990 |
| JP | 02-300210 | 12/1990 |
| JP | 03-179008 A | 8/1991 |
| JP | 4-227705 | 8/1992 |

(Continued)

OTHER PUBLICATIONS

EPO Notice of Opposition dated Oct. 17, 2012, issued in EP Application No. 04773399.3 and English translation thereof.
Edited by Fredric L. Buchholz and Andrew T. Graham, "Modern Superabsorbent Polymer Technology", pp. 148-153, Copyright 1998.

*Primary Examiner* — Robert C Boyle
(74) *Attorney, Agent, or Firm* — Harness, Dickey & Pierce, P.L.C.

(57) ABSTRACT

An object of the present invention is to provide a water absorbent having excellent gel properties and showing excellent properties when used in a water-absorbing material of a sanitary/hygienic material such as paper diaper. Moreover, another object of the present invention is to provide a water absorbent which is safe and excellent in liquid permeability, and in which an amount of liquid permeability improver for improving the liquid permeability is reduced. The water absorbent is made from a water-absorbing resin prepared by a specific polymerization method and having a high degree of cross-linking, a high liquid holding property and a high gel strength (its swelling pressure of gel layer of is 35 kdyne/cm2 or more). This water absorbent is further processed to have a particular particle size distribution (95 wt % or more of its particles are less than 850ƒÊm but not less than 106ƒÊm, and logarithmic standard deviation (ƒĐƒÄ) is in a range of 0.25 to 0.45) and then surface cross-linked. After that, a liquid permeability improver is added therein.

11 Claims, 4 Drawing Sheets

| | FOREIGN PATENT DOCUMENTS | |
|---|---|---|
| JP | 09-077832 | 3/1997 |
| JP | 09-124710 A | 5/1997 |
| JP | 10-147724 A | 6/1998 |
| JP | 2002-85959 | 3/2002 |
| JP | 2002-121291 | 4/2002 |
| JP | 2002-513043 | 5/2002 |
| JP | 2002-513059 | 5/2002 |
| JP | 2002-212204 | 7/2002 |
| JP | 2003-088553 | 3/2003 |
| JP | 2003-105092 | 4/2003 |
| JP | 2004-217911 * | 8/2004 |
| WO | WO 95/22356 | 8/1995 |
| WO | WO98/48857 | 11/1998 |
| WO | WO99/55393 | 11/1999 |
| WO | WO99/55767 | 11/1999 |
| WO | WO 00/53644 | 9/2000 |
| WO | WO 00/53664 | 9/2000 |
| WO | WO 01/66056 A1 | 9/2001 |
| WO | WO 02/053199 | 7/2002 |
| WO | WO 02/100451 | 12/2002 |
| WO | WO/02/100451 * | 12/2002 |
| WO | WO 03/051415 A | 6/2003 |
| WO | WO2004/069293 A1 | 8/2004 |
| WO | WO2004/069915 A2 | 8/2004 |
| WO | WO2004/113452 A1 | 12/2004 |

* cited by examiner

WATER ABSORBENT AND PRODUCING METHOD OF SAME

PRIORITY STATEMENT

This application is a divisional application under 35 U.S.C. §121 of U.S. application Ser. No. 10/572,565, filed Mar. 17, 2006, now issued U.S. Pat. No. 7,803,880, which is a national phase application under 35 U.S.C. §371 of International Application No. PCT/JP2004/014015, filed Sep. 17, 2004, which claims priority under 35 U.S.C. §119 to JP 2003-329109, filed Sep. 19, 2003, and JP 2003-329110, filed Sep. 19, 2003, the entire contents of each of which is incorporated herein in by reference.

TECHNICAL FIELD

The present invention relates to a water absorbent and producing method of the same. More particularly, the present invention relates to a water absorbent, which is suitably applicable to sanitary/hygienic materials such as paper diapers, sanitary napkins, so-called incontinent pads and the like, and a producing method of the same.

BACKGROUND ART

Today, water-absorbing resin and hydrophilic fibers such as pulps are widely used as components of sanitary/hygienic materials (hereinafter, they are collectively referred to as sanitary materials, sometime) such as paper diapers, sanitary napkins, so-called incontinent pads and the like, in order to use the water-absorbing resins and the hydrophilic fibers to absorb body fluids.

As a main raw material of the water-absorbing resins, the following materials are used, for example: a cross-linked polymer containing partially-neutralized polyacrylic acid; starch-acrylic graft polymer; saponificated vinyl acetate-acrylic ester copolymer; hydrolyzed acrylonitril copolymer; hydrolyzed acrylamide copolymer; cross-linked hydrolyzed acrylonitril copolymer; cross-linked hydrolyzed acrylamide copolymer; and cross-linked polymer prepared from a cationic monomer; and the like material.

In case where they have a high water absorbency, these generally-used water-absorbing resins tend to be poor in tolerance against urine (anti-urine tolerance), durability, and temporal stability (stability in terms of changes over time), when they become swelled gels. Therefore, the generally-used water-absorbing resins have such problems that the swelled gels become sticky (slimy), or are liquidized as time passes by. In order to solve the problems, various methods to give the swelled gels a better durability or a better temporal stability have been suggested.

For examples, the following methods are suggested: a method in which a water-soluble ethylene-based unsaturated monomer is polymerized by reverse-phase suspension polymerization in the presence of a cross-linking agent and a water-soluble chain transfer agent (Japanese Laid open patent application, Tokukaihei, publication No. 2-255804; Reference 1); a method in which a highly water-absorbing polymer is prepared by polymerizing, in the presence of a hypophosphorus compound, a water-soluble monomer whose main component is an acrylic acid and its alkali (Japanese Laid open patent application, Tokukaihei, publication No. 2-300210; Reference 2); a method in which a water-soluble ethylene unsaturated monomer is polymerized by aqueous polymerization in the presence of a cross-linking agent and a water-soluble chain transfer agent (Japanese laid open patent application, Tokukaihei, publication No. 3-179008; Reference 3); a method of producing an absorbent by polymerizing, in the presence of a cross-linking agent, a water-soluble radical polymerizable monomer having an acid base or its salt, with a thiol compound having a radical polymerizable double bond (Japanese laid-open patent application, Tokukaihei, Publication No. 9-77832; Reference 4); a method in which a water-absorbing resin is surface-treated, the water-absorbing resin prepared by aqueous polymerization of a hydrophilic unsaturated monomer in the presence of an internal cross-linking agent, and phosphorous acid and/or its salt, the hydrophilic unsaturated monomer containing, as its main component, acrylic acid and/or its alkali metal salt (Japanese laid-open patent application, Tokukaihei, Publication No. 9-124710; Reference 5); and the like method.

In these methods, a chain transfer agent is used in the polymerization so as to change an internal structure of a gel, thereby improving durability of the swelled gel, and temporal stability and anti-urine tolerance of the gel. However, objects of these arts are to improve the gel having a high water absorbency, in terms of durability, anti-urine tolerance, and temporal stability, in which the gel is poor. Therefore, the water-absorbing resins (or absorbents) have insufficient property as a gel. Thus, in order to be used in a water-absorbing material for a paper diaper or the like, these water-absorbing resins need to be improved in terms of properties.

Moreover, in these days there is an upward trend in an amount of the water-absorbing resin per sanitary material in a paper diaper, a sanitary napkin, or the like, and in a percentage by weight of the water-absorbing resin in a water-absorbing material that is constituted of the water-absorbing resin, the hydrophilic fiber, and the like. That is, the water-absorbing material in these days contains the water-absorbing resin in a higher ratio by reducing an amount of the hydrophilic fiber (pulp) having a small bulk density, while increasing the water-absorbing resin having a large bulk density. Hereby, thin sanitary materials are attained without reducing their water absorbency. As a result, the water-absorbing resins should have a function of liquid transportation and liquid distribution, in lieu of the hydrophilic fiber such as a pulp or the like. These functions may be simply referred to as liquid permeability.

In case of the water-absorbing resin in a particle shape, the liquid permeability is considered as an ability of transporting, through insides or gaps of particles, a liquid added onto the water-absorbing resin, so as to three-dimensionally distribute the liquid throughout the water-absorbing resin as swelling the water-absorbing resin. In the gel, which is obtained by swelling the water-absorbing resin as such, this process is carried out by the liquid transportation caused by capillary phenomenon by which the liquid is transported through gaps of particles in the gel.

Moreover, when the liquid passes through the swelled water-absorbing resin, actual liquid transportation follows a rule of diffusion. This is such a slow process that is almost useless to carry out the liquid distribution under the condition under which the sanitary goods are used. On the other hand, in a water-absorbing resin in which the capillary transportation is impossible due to instability of its gel, these materials are so arranged that they are planted in matrix of the fibers so as to separate particles from each other, in order to avoid blocking phenomenon in the gel. Diapers of a new generation has such a structure in which a water-absorbing resin layer contains none or a little amount of a fiber material for assisting the liquid transport. Accordingly, the water-absorbing resin used therein should have a sufficiently high stability when the water-absorbing resin is swelled (to be the swelled gel). With, such high stability, the swelled gel would have a sufficient amount of capillary gaps and thus the liquid transport would be allowed in the swelled gel.

In general, in order that a water-absorbing resin may have a high gel strength when swelled, the water-absorbing resin should be prepared from a polymer having a higher cross-linking level. However, the higher cross-linking level inevitably results in loss of swelling volume and retention capacity. Moreover, U.S. Pat. No. 6,403,700 discloses a method of improving a swelling pressure of a gel of a surface cross-linked water-absorbing resin that is neutralized after prepared by acidic polymerization that is carried out at a low neutralization ratio (5 mol % to 30 mol %). However, because it is necessary to deal with the highly acidic polymer, this method has problems in terms of safety and process complexity. Therefore, this method is hard to apply in an industrial production. Moreover, this method cannot attain such a liquid permeability of the water-absorbing resin that allows the structure of the diaper to include a layer solely made of the water-absorbing resin.

Moreover, it is well known that the surface treatment gives the water-absorbing resin a high gel strength. A water-absorbing resin having a high gel strength and a high liquid absorbing ability against pressure is obtained by treating the water-absorbing resin with a surface cross-linking agent of various kinds, or a certain polymer, which are reactive with carboxyl groups of polymer molecules on a surface of the water-absorbing resin. The surface treatment prevents the gel blocking phenomenon.

There are proposed a number of methods to improve the liquid permeability and the diffusibility by modifying the surface of the water-absorbing resin by the surface treatment. Examples of the methods include: a method in which a water-absorbing resin cross-linked via a certain metal ion is used (Japanese laid-open applications, publication Nos. 2002-513043, and 2002-513059); a method in which a water-absorbing resin is improved by a polyamine or a polyimine dissolved in an organic solvent (pamphlet of international publication No. 95/22356); a method in which a water-absorbing resin is surface-treated with a surface cross-linking agent containing a polyol and an aqueous cation (pamphlet of international publication No. 00/53644); a method in which a water-absorbing resin is surface-treated with a surface cross-linking agent containing an aqueous cation and an organic cross-linked compound except polyols (pamphlet of international publication No. 00/53664). It is possible to prevent the gel blocking by these well-known methods. However, in case where the surface treatment is carried out according to these methods, it is not possible to sufficiently improve the diaper having a high water-absorbing resin content in terms of the liquid permeability, especially Saline Flow Conductivity for a sodium chloride solution of 0.69% by weight (Hereinafter, referred to as SFC). Moreover, the surface cross-linking improves the gel strength by increasing the cross-linking density only in a vicinity of surfaces of the particles of the water-absorbing resin, but not interiors of the particles. Thus, the gel strength is not principally improved because the surface cross-linking cannot increase the cross-linking density in the insides of the particles.

Especially, it is well known to improve handling easiness, preservability, or water-absorbing property of a water-absorbing resin powder by adding an inorganic compound to the water-absorbing resin powder.

Examples of the methods include: a method of producing a water-absorbing resin by dry-blending the water-absorbing resin produced with a multivalent metal salt such as aluminum sulfate and then causing the water-absorbing resin to contact with a binding agent (such as water), whereby the water-absorbing resin becomes elastic and difficult to cause the gel blocking (pamphlet of international publication No. 98/48857); a method in which a water-absorbing resin is applied with a mechanical stress by an Osterizer blender or the like after mixed with a permeability retaining agent (such as silica, alumina, titania, clay, an emulsified polymer, suspension polymer, or the like) by a Vortex mixer (pamphlet of international publication No. WO 01/66056); a method in which a surface-treated water-absorbing resin having a specific gel strength is coated with structural or electrostatic spacer; a method of producing a highly water-absorbing resin material containing a highly water-absorbing resin and particles that are agglomerations of hydrate oxide containing two types of metals M1 and M2 at least partially having -M1-O-M2 bond (Japanese laid open patent application, publication No. 10-147724).

By these well known methods, it is possible to prevent the gel blocking. However, with these methods the water-absorbing resin cannot have sufficient liquid diffusibility, especially SFC, to be used in a diaper, or can be used in the diaper only if a very large amount of a liquid permeability improver such as organic or inorganic particles is added therein. Therefore, these methods have a dusting problem (flying of powder, clogging of filters and the like problems in productions of the water absorbent and the diaper). Therefore, it is necessary to improve the water absorbing resin (or water absorbent) in terms of safety and cost.

DISCLOSURE OF INVENTION

Accordingly, an object of the present invention is to solve the aforementioned problems and provide (a) such a water absorbent that has an excellent gel property (that is, a particular particle size distribution, a particular absorbency for 0.9 wt % saline (CRCs), a particular absorbency against pressure (AAPs) for 0.9 wt % saline, a particular chemical cross-linking index or chemical cross-linking index against pressure), and shows excellent properties when used in a water-absorbing material for use in sanitary/hygienic materials such as paper diapers, and (b) a method of producing the water absorbent.

The inventors of the present invention, as a result of diligent studies in an attempt to solve the aforementioned problems, found out a water absorbent showing excellent properties when used in a water absorbing material such as paper diapers, the water absorbent having more excellent gel properties than conventional ones by having a particular particle size distribution, a particular CRCs, a particular AAPs, and a particular chemical cross-linking index (chemical cross-linking index against pressure).

Moreover, the inventors of the present invention, as a result of diligent studies in an attempt to attain the aforementioned objects, found out a water absorbent showing excellent properties when used in a water absorbing material such as paper diapers, the water absorbent having more excellent gel properties than conventional ones by being prepared from a water-absorbing resin (a) prepared by polymerization in the presence of an internal cross-linking agent of a particular amount and a water-soluble chain transfer agent of a particular amount, (b) processed to have a particular particle size distribution, and (c) subjected to a surface treatment so as to have a particular absorbency.

Moreover, in addition to the above findings, the inventors found out that the water absorbent according to the present invention having the excellent gel properties shows excellent liquid permeability and diffusibility than the conventional ones, by containing a liquid permeability improver.

Specifically, a water absorbent according to the present invention containing water-absorbing resin particles, which are surface cross-linked and prepared from a water-absorbing resin having a cross-linked structure prepared by polymerizing a monomer including at least acrylic acid and/or its salt, the water absorbent satisfying:

(a) 90% by weight or more of the particles have a diameter less than 850 μm but not less than 150 μm;

(b) a logarithmic standard deviation ($\sigma\zeta$) of the particle size distribution is in a range of 0.25 to 0.45;

(c) AAPs for 0.9 wt % saline is 20 g/g or more;

(d) CRCs for 0.9 wt % saline is not less than 29 g/g but less than 39 g/g;

(e) a chemical cross-linking index is 160 or more, the chemical cross-linking index represented by Formula (1):

$$\text{Chemical Cross-Linking Index} = (CRCs)/(CRCdw) \times 1000 \quad (1),$$

where CRCs(g/g) is an absorbency for 0.9 wt % saline, and CRCdw(g/g) is an absorbency for deionized water.

Moreover, a water absorbent according to the present invention containing water-absorbing resin particles, which are surface cross-linked and prepared from a water-absorbing resin having a cross-linked structure prepared by polymerizing a monomer including at least acrylic acid and/or its salt, satisfies:

(a) 90% by weight or more of the particles have a diameter less than 850 μm but not less than 150 μm;

(b) a logarithmic standard deviation ($\sigma\zeta$) of the particle size distribution is in a range of 0.25 to 0.45;

(c) AAPs for 0.9 wt % saline is 20 g/g or more;

(f) CRCs for 0.9 wt % saline is not less than 15 g/g but less than 29 g/g;

(g) a chemical cross-linking index against pressure is 100 or more, the chemical cross-linking index against pressure represented by Formula (2):

$$\text{Chemical Cross-Linking Index Against Pressure} = (CRCs) \div (AAPdw) \quad (2),$$

where CRCs(g/g) is an absorbency for 0.9 wt % saline, and AAPdw (g/g) is an absorbency against pressure for deionized water.

With these arrangements, the water absorbent shows the excellent gel properties and is more excellent than the conventional ones in terms of the properties when used as a water absorbent for use in a water absorbing material such as paper diapers, sanitary napkins or the like.

A method, according to the present invention, of producing a water absorbent whose main component is water-absorbing resin particles (E) prepared by polymerizing a monomer (A) in a presence of an internal cross-linking agent (B) in a range of 0.005 mol % to 5 mol %, and a water-soluble chain transfer agent (C) in a range of 0.001 mol % to 1 mol %, in order to obtain a water-absorbing resin (D), the monomer (A) containing acrylic acid and/or its salt, and then performing surface cross-linking of the water-absorbing resin (D) in order to attain the water-absorbing resin particles (E), wherein the water absorbent satisfies:

(a) 90% by weight or more of the particles have a diameter less than 850 μm but not less than 150 μm; and (b) a logarithmic standard deviation ($\sigma\zeta$) of the particle size distribution is in a range of 0.25 to 0.45.

According to the above method, it is possible to produce a water absorbent that shows the excellent gel properties and is more excellent than the conventional ones in terms of the properties when used as a water absorbent for use in a water absorbing material such as paper diapers, sanitary napkins or the like.

Moreover, an object of the present invention is to solve the aforementioned problem and to provide a water absorbent and a method of producing the same, the water absorbent having a high absorbency, a high instinct gel stability, a higher liquid permeability, and high safety, thereby being suitably applicable in sanitary/hygienic materials or absorbing goods that have a high content of a water-absorbing resin and a thin thickness.

As a result of diligent studies in an attempt to attain the objects, the inventors of the present invention found out that a particular polymerization method attains such a water-absorbing resin that compossibly have high cross-linking level, high absorbency, high swelling pressure of gel layer, even though it is impossible to compossibly have these properties by the conventional polymerization methods.

Furthermore, the inventors of the present invention found out that addition of a liquid permeability improver to the water-absorbing resin particles obtained by the producing method according to the present invention attains a higher SFC than the water-absorbing resin prepared by the conventional polymerization methods, the water-absorbing resin particles having an excellent swelling pressure (specified by a later described measuring method) of the gel layer and being regulated to have a particular particle size distribution and surface cross-linked.

Specifically, the method according to the present invention of producing a water absorbents is as any one of (1) to (3):

(1) a method of producing a water absorbent containing water-absorbing resin particles, which are surface cross-linked and prepared from a water-absorbing resin prepared by cross-linking polymerization of a monomer including acrylic acid and/or its salt, wherein: the water absorbing resin has. Swelling Pressure of Gel Layer (SPGL (B)) of 35.0 (kdyne/cm$^2$) or more; the particles has such a particle size distribution that 95% to 100% by weight of the particles have a diameter less than 850 μm but not less than 106 μm, the particle size distribution measured by JIS standard sieve; and a logarithmic standard deviation ($\sigma\zeta$) of the particle size distribution is in a range of 0.25 to 0.45.

(2) A method of producing a water absorbent containing water-absorbing resin particles, which are surface cross-linked and prepared from a water-absorbing resin prepared by cross-linking polymerization of a monomer including acrylic acid and/or its salt, wherein: the water-absorbing resin has a swelling pressure of gel layer (SPGL(B)) of 35.0 (kdyne/cm$^2$) or more and is surface cross-linked until the water-absorbing resin has Saline Flow Conductivity (SFC) of 40 ($10^{-7}$ cm$^3$s g$^{-1}$) or more for a sodium chloride solution of 0.69% by weight, and then adding a liquid permeability improver to the water-absorbing resin.

(3) A method of producing a water absorbent containing water-absorbing resin particles, which are surface cross-linked and prepared from a water-absorbing resin prepared by cross-linking polymerization of a monomer including acrylic acid and/or its salt, wherein: the cross-linking polymerization is a boiling polymerization that is carried out in the presence of a water-soluble chain transfer agent of 0.001 mol % to 10 mol % with respect to the monomer to be polymerized by the boiling polymerization.

As described above, one arrangement of the present invention is to obtain a water-absorbing resin having a high swelling pressure of a gel layer, perform surface cross linking of the water-absorbing resin, and then to add liquid permeability improver.

The measurement of the gel layer in the present invention is carried out by measuring a swelling force of the gel layer of the water-absorbing resin that has not been surface cross-linked, the swelling force being a force to swell from a certain volume which the gel layer is adjusted to have. In water-absorbing resins for use in thin diaper having high water-absorbing resin contents, gel stability of the water absorbing resins is obtained for attaining a high liquid permeability in the diapers, and in order to obtain the gel stability, improving gel strength and modifying a surface, of the water absorbing resins by the surface cross-linking. However, what is essentially important is how stable the water-absorbing resins before surface cross-linked is in swelling.

In the measurement, used in the present invention, for measuring the swelling pressure of the gel layer, instinct stability of the gel shown during the swelling thereof. The high liquid permeability required for the thin diaper having a higher water absorbent content can be attained by using a water absorbent prepared from the water-absorbing resin according to the present invention being excellent in this swelling pressure of the gel layer, and containing a liquid permeability improver added after the surface cross-linking treatment.

For a fuller understanding of the nature and advantages of the invention, reference should be made to the ensuing detailed description taken in conjunction with the accompanying drawings.

BEST MODE FOR CARRYING OUT THE INVENTION

Figure 1:
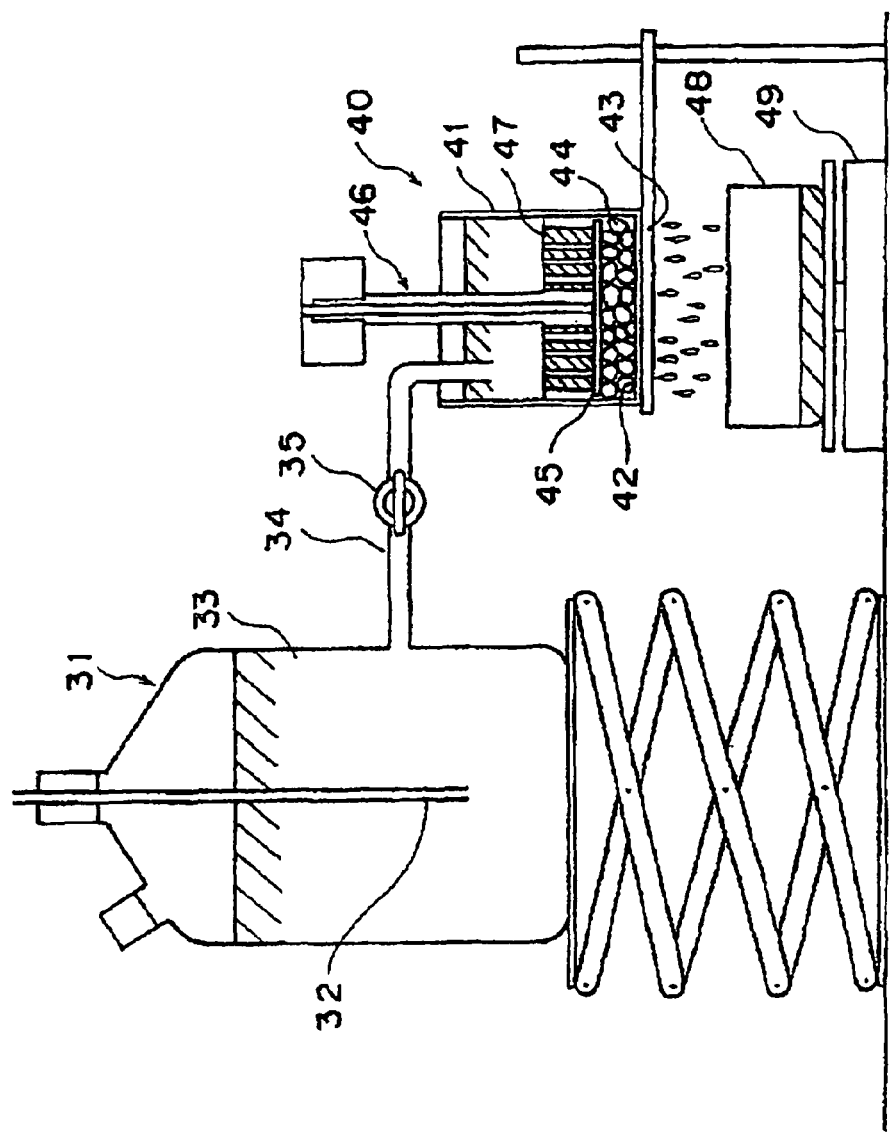
FIG. 1 is a cross sectional view schematically showing a measuring apparatus for use in measurement of Saline Flow Conductivity (SFC) for 0.69 wt % saline.

[First Embodiment]
To begin with, abbreviations used in the present invention are defined here. CRCs (Centrifuge Retention Capacity saline) is absorbency for 0.9 wt % saline.

CRCdw (Centrifuge Retention Capacity deionized water) is absorbency for deionized water.

AAPs (Absorbency Against Pressure saline) is absorbency for a saline measured when pressure is applied on a sample.

AAPdw (Absorbency Against Pressure deionized water) is absorbency for deionized water measured when pressure is applied on a sample.

SFC (Saline Flow Conductivity) is flow conductivity for 0.69 wt % saline.

CSF (Capillary Suction Force) indicates absorbency due to capillary suction.

D50 is a weight-average particle diameter.

σζ is a logarithmic standard deviation of particle size distribution.

Measuring methods for those figures will be described in Example later. The saline is an aqueous solution of sodium chloride.

In the present invention, the terms "weight" and "mass" are considered to have the same meaning, and the term "weight" is used for the sake of uniform expression.

The present invention is described in detail below. Note that a water absorbent of the present invention is water-absorbing resin particles (particles of water-absorbing resin) or a material whose main component is water-absorbing resin particles. The water absorbent of the present invention is preferably a material containing the water-absorbing resin particles preferably in a range of 90% to 100% by weight, more preferably in a range of 95% to 100% by weight. The water absorbency of the present invention is suitably applicable to sanitary/hygienic materials such as paper diapers, sanitary napkins, so-called incontinent pads, and the like.

The water absorbent according to the present invention is or contains water-absorbing resin particles having a particular gel characteristics. The water absorbent is, if necessary, arranged such that the water-absorbing resin particles contain a liquid permeability improver.

A method, of the present invention, of producing a water absorbent, is a method of synthesizing a particular water-absorbing resin, processing the water-absorbing resin to be water-absorbing resin particles having a particular particle size distribution, and performing surface treatment of the water-absorbing resin particles with a particular surface treatment agent. Moreover, a method, of the present invention, of producing a water absorbent is a method arranged such that a permeability improver is added, if necessary.

(1) Method of Producing Particles of Water-Absorbing Resin
(1-1) Monomer (A)

A monomer used in the present invention contains acrylic acid and/or its salt. Content of acrylic acid and/or its salt (acrylic acid content and/or acrylic salt content) is preferably in a range of 70 mol % to 100 mol %, more preferably in a range of 80 mol % to 100 mol %, and most preferably in a range of 90 mol % to 100 mol %, in order to further improve water-absorbing properties and gel property of the water absorbent.

Examples of the acrylic salt include: alkali metal salts of acrylic acid with sodium, potassium, lithium or the like; ammonium salts, amine salts, and the like salt, of acrylic acid.

As the salt of acrylic acid, sodium salt is preferable. It is preferable that the monomer (A) contain, as its constituents, acrylic acid in a range of 0 mol % to 50 mol %, and acrylic salt in a range of 100 mol % to 50% mol (where a total amount of them is not more than 100 mol %). It is more preferable that the monomer (A) contain, as its constituents, acrylic acid in a range of 10 mol % to 40 mol %, and acrylic salt in a range of 90 mol % to 60% mol (where a total amount of them is not more than 100 mol %). Note that a molar ratio between the acid and the salt is a neutralization ratio. For example, a monomer constituted of acrylic acid by 30 mol % and acrylic salt by 70 mol % has a neutralization ratio of 70%. To form the salt, neutralization of carboxylic group may be performed (a) before polymerization, that is, when the monomer is still a monomer, (b) during or after the polymerization, when the monomer becomes a polymer, or (c) in combination of (a) and (b). It is preferable that the neutralization be carried out (a) before the polymerization when the monomer is still a monomer. Note that the acrylic acid used here may be acrylic acid prepared by a well known method. For example, the well known acrylic acid is described in publication of US patent application, No. 2001-0016668, U.S. Pat. Nos. 5,817,865 and 6,596,901.

The monomer (A) used in the present invention for obtaining the water-absorbing resin may contain a monomer other than the acrylic acid (salt) as required. The monomer other than acrylic acid (salt) (hereinafter, sometimes referred to as "other monomer") is not particularly limited. Specific examples of the monomer other than acrylic acid (salt) include:
anionic unsaturated monomers (and their salts) such as methacrylic acid, maleic acid (anhydrate), itaconic acid, cinnamic acid, allyltoluenesulfonic acid, vinyl toluenesulfonic acid, 2-(meth)acryloylethanesulfonic acid, 2-hydroxyethyl(meth)acryloylphosphate, vinyl sulfonic acid, stylenesulfonic acid 2-(meth)acrylamide-2-methylpropanesulfonic acid, 2-(meth)acryloylethanesulfonic acid, 2-(meth)acryloylpropanesulfonic acid, and the like; mercaptan group-containing unsaturated monomers; phenolic hydroxy group containing unsaturated monomers; non-ionic hydrophilic group containing unsaturated monomers such as (meth)acryl amide, N-ethyl(meth)acrylamide, N-n-propyl(meth)acrylamide, N-isopropyl(meth)acrylamide, N,N-dimethyl(meth)acrylamide, 2-hydroxyethyl(meth)acrylate, 2-hydroxypropyl (meth)acrylate, methoxypolyethyleneglycol(meth)acrylate, polyethyleneglycolmono(meth)acrylate, vinylpyridine, N-vinylpyrrolidone, N-acryloylpiperidine, N-acryloylpyrrolidine, N-vinylacetoamide, and the like; cationic unsaturated monomers such as N,N-dimethylaminoethyl(meth)acrylate, N,N-dimethylaminoethyl(meth)acrylate, N,N-diethylaminoethyl(meth)acrylate, N,N-dimethylaminopropyl(meth)acrylate, N,N-dimethylaminopropyl(meth)acrylamide, and their quaternary salts. These other monomers may be used solely or, two or more of them may be used in appropriate combination. In terms of the properties and the cost of the resultant water absorbing resin, it is preferable to use, as the main component, acrylic acid and/or its salt (for example, with sodium, lithium, potassium, ammonium, amines, and the like) It is especially preferable to use sodium salt of acrylic acid in terms of cost.

In the present invention, in case where the other monomer than acrylic acid (salt) is used, the other monomer content is preferably 30 mol % or less, and more preferably 10 mol % or less. By containing the other monomer in the content, the absorbing properties of the resultant water-absorbing resin (or absorbent) are further improved and a cost of the resultant water-absorbing resin (or absorbent) is further reduced.

(1-2) Internal Cross-Linking Agent (B)

The water-absorbing resin for use in the present invention may be of self-cross-linking type in which no cross-linking agent may be used. It is preferable that the water-absorbing resin be a resin prepared by copolymerizing a monomer with or reacting a monomer with a cross-linking agent (internal cross-linking agent (B) for the water-absorbing resin). The internal cross-linking agent (B) may be a cross-linking agent having, per molecule, two or more polymerizable unsaturated group and/or reactive group, or a cross-linking agent that is a cyclic compound that have, per molecule, two or more reactive groups after open-ring reaction. It is further preferable that the water-absorbing resin be a resin prepared by polymerization in the presence of the internal cross-lining agent (B).

Examples of the internal cross-lining agent (B) includes N,N'-methylenebis(meth)acrylamide, (poly)ethyleneglycoldi(meth)acrylate, (poly)propyleneglycoldi(meth)acrylate, trimethylolpropanetri(meth)acrylate, glycerictri(meth)acrylate glycericacrylatemethacrylate, ethyleneoxide denatured trimethylolpropanetri(meth)acrylate, pentaerythritoltetra (meth)acrylate, triallylcyanurate, triallylisocyanurate, triallylphosphate, triallylamine, poly(meth)allyloxyalkanes, polyethyleneglycoldiglycidylether, glyceroldiglycidylether, glyceroldiglycidylether; multivalent alcohols such as ethyleneglycol, polyethyleneglycol, propyleneglycol, 1,3-butanediol, 1,4-butanediol, glycerin, pentaerythritol, and the like; ethylenediamine, ethylenecarbonate, propylenecarbonate, polyethyleneimine, glycidyl(meth)acrylate, and the like; and the like.

These internal cross-linking agents (B) may be used solely, or two or more of them may be used in appropriate combination. Moreover, the internal cross-linking agent (B) may be added into a reaction system at once or stage by stage. In the case where at least one of or two or more of the internal cross-linking agents (B) are used, it is preferable that the polymerization be carried out at least with a compound having two or more polymerizable unsaturated groups, in consideration of the water absorbing properties or the like of the resultant water-absorbing resin or the water absorbent.

With respect to the monomer (A) (excluding the internal cross-linking agent (B)), internal cross-linking agent (B) content is preferably in a range of 0.005 mol % to 5 mol %, more preferably in a range of 0.06 mol % to 0.30 mol %, and most preferably in a range of 0.08 mol % to 0.20 mol %. The internal cross-linking agent (B) content of less than 0.005 mol %, and the internal cross-linking agent (B) content of more than 5 mol % would possibly result in insufficient water absorbing properties.

Introduction of a cross-linked structure into the polymer by using the internal cross-linking agent (B), the internal cross-linking agent (B) is added before, during, or after the polymerization of the monomer (A). It is preferable to add the internal cross-linking agent (B) before the polymerization.

(1-3) Water-Soluble Chain Transfer Agent (C)

In the present invention, a chain transfer agent for use in the polymerization of the monomer (A) is preferably a water-soluble chain transfer agent. A water-insoluble change transfer agent would possibly fail to give the resultant water absorbent a sufficient chemical cross-linking index (or chemical cross-linking index against pressure). The water-soluble chain transfer agent (C) for use in the present invention is not particularly limited, provided that the water-soluble chain transfer agent (C) is soluble in water, or a solution of acrylic acid and/or its salt. The water-soluble chain transfer agent (C) may be a thiol, a thiol acid, a secondary alcohol, an amine, a phosphorous compound, a transition metal complex, or the like. Specific examples of the water-soluble chain transfer agent (C) include: mercaptoethanol, mercaptopropanol, dodecyl mercaptan, thioglycolic acid and its salt, thiomalic acid and its salt, 3-mercaptopropionic acid and/or its salt, isopropanol, formic acid and its salt, hypophosphorous acid and its salt, and phosphorous acid and/its salt. One of, or two or more of the water-soluble chain transfer agents (C) are selected and used. Because of their effect, it is preferable that the water-soluble chain transfer agent (C) be one of, or two or more of thiomalic acid and its salt, hypophosphorous acid and its salt, and phosphorous acid and its salt. It is more preferable that the water-soluble chain transfer agent (C) be one of, or two or more of hypophosphorous acid and its salt, and phosphorous acid and/or its salt.

An amount of the water-soluble transfer agent (C) to add is, with respect to the monomer (A), in a range of 0.001 mol % to 10 mol %, preferably in a range of 0.001 mol % to 2 mol %, more preferably in a range of 0.001 mol % to 1 mol %, further preferably in a range of 0.005 mol % to 0.5 mol %, and most preferably in a range of 0.01 mol % to 0.3 mol %, even though it depends on concentration of the monomer in its aqueous solution, and the amount of the internal cross-linking agent (B). If the amount of the water-soluble transfer agent (C) to add was less than 0.001 mol %, a sufficient chemical cross-linking index (or chemical cross-linking index against pressure) would not be obtained possibly. If the amount of the water-soluble transfer agent (C) to add was more than 10 mol %, an increase in water soluble content would possibly make it impossible to obtain a water absorbent having sufficient chemical cross-linking index (or chemical cross-linking index against pressure).

(1-4) Water-Absorbing Resin (D)

The polymerization of the monomer (A) to prepare water-absorbing resin (D) for use in the present invention may be carried by bulk polymerization or suspension polymerization. However, because of resultant properties, easy control of polymerization process, and water absorbing properties of the swelled gel, it is preferable to carry out the polymerization by aqueous polymerization or reverse-phased suspension polymerization. The aqueous polymerization is most preferable. The aqueous polymerization is well known, and described, for example, in U.S. Pat. Nos. 4,625,001, 4,769,427, 4,873,299, 4,093,776, 4,367,323, 4,446,261, 4,683,274, 4,690,996, 4,721,647, 4,738,867, and 4,748,076, and European Patent No. 1178059, and the like. In case where an aqueous solution of the monomer (A) (hereinafter, referred to as a monomer aqueous solution) is prepared, monomer (A) content in the monomer aqueous solution depends on a temperature of the monomer aqueous solution or type of the monomer (A), and is not particularly limited. However, the monomer (A) content is preferably in a range of 30% to 70% by weight, and more preferably in a range of 35% to 70% by weight. A monomer (A) content of less than 30% by weight reduces productivity per unit reaction volume, and requires a drying step thereby requiring a longer time and more energy and thus resulting in lower productivity. Therefore, the monomer (A) content of less than 30% by weight is not industrially preferable.

The aqueous polymerization may be carried out (i) by polymerizing the aqueous solution of the monomer (A) in a two-armed kneader while crushing a hydrate gel obtained from the polymerization, (ii) by supplying the aqueous solution of the monomer (A) into a prescribed container or onto a moving belt, and polymerizing (or boiling-polymerizing) the monomer (A) therein/thereon so as to obtain the gel, and then crushing the gel with a meat chopper or the like, or (iii) by the like method.

There is no particular limit in the polymerization initiator. The polymerization may be started by using a radical polymerization initiator, or an optical polymerization initiator. The radical polymerization initiator may be, for example, a persulfate (potassium persulfate ammonium persulfate, sodium persulfate or the like); a peroxide (hydrogen peroxide, t-butylhydroperoxide, a methylethylketone peroxide, or the like); an azo compound (an azonitril compound, an azoamidine compound, a cyclic azoamidine compound, an azoamide compound, an alkyl azo compound, 2,2'-azobis(2-amizinopropane)dihydrochloride, 2,2'-azobis[2-(2-imidazoline-2-il)propane]dihydrochloride, or the like). The optical polymerization initiator may be, for example, a benzoin derivative, a benzyl derivative, an acetophenone derivative, a benzophenone derivative, an azo compound, or the like.

Furthermore, a redox type initiator may be applied by using a reductant in addition to the polymerization initiator, the reductant facilitating decomposition of these kinds of polymerization initiators. The reductant may be, but not limited to, a persulfate (salt) or a bisulfate salt such as sodium persulfate, sodium hydrogen persulfate or the like; L-ascorbic acid (salt); a reducing metal (salt) such as a primary iron salt or the like; an amine; or the like.

An amount of the polymerization initiator to add is generally in a range of 0.001 mol % to 2 mol %, and preferably in a range of 0.01 mol % to 0.1 mol %, with respect to the monomer (A). The amount of the polymerization initiator of less than 0.001 mol % is not preferable because, if so, an amount of the monomer (A) left unreacted would be increased, thus increasing an amount of the monomer remained in the resultant water-absorbing resin (D) and water absorbent. On the other hand, there is a case that the amount of the polymerization initiator of more than 2 mol % is not preferable because, if so, the resultant water-absorbing resin (D) and water absorbent would possibly have a higher water-soluble content.

Moreover, the polymerization may be started by radiating onto the reaction system active energy rays such as radioactive rays, electron rays, ultraviolet rays, or the like. Further, the polymerization may be started by radiating the active energy rays in combination of the use of the polymerization initiator. A reaction temperature is not particularly limited, but is preferably in a range of 10° C. to 130° C., more preferably in a range of 15° C. to 120° C., and especially preferably in a range of 20° C. to 100° C. Moreover, there is no particular limit in reaction time and polymerization pressure, which may be arbitrarily set to be suitable for the types of the monomer and the polymerization initiator, the reaction temperature, and the like.

The polymerization may be carried out with an additive added to the reaction system. Examples of the additive include: various foaming agents which contains a hydrophilic polymer in a range of 0% to 50% by weight (with respect to the monomer), another component in a range of 0% to 10% by weight, and the like, where the hydrophilic polymer may be starch/cellulose, derivatives of starch/cellulose, polyvinyl alcohol, polyacrylic acid (salts), polyacrylic acid (salt)-based cross linking material, or the like, and the another component may be (hydrogen) carbonate, carbon dioxide, an azo compound, and an inert organic solvent, or the like; various surfactants; chelating agents; inorganic particulates such as kaolin, talc, silicon dioxide, and the like; multivalent metal salts such as aluminum polychloride, aluminum sulfate, magnesium sulfate, and the like; and the like.

In case where the cross-linked polymer is one prepared by the aqueous polymerization and in a gel form, that is, the cross-linked polymer is a hydrate gel-form cross-linked polymer, the cross-linked polymer is dried if necessary, and crushed before and/or after the drying, thereby obtaining the water-absorbing resin (D). The drying is carried out at a temperature generally in a range of 60° C. to 250° C., preferably in a range of 100° C. to 220° C., and more preferably in a range of 120° C. to 200° C. Drying time depends on a surface area of the polymer, moisture content, and a type of dryer to use, and is arbitrarily selected to attain a target moisture content.

There is no particular limit in the target moisture content of the water-absorbing resin (D) that can be used in the present invention (the moisture content is defined by a water content in the water-absorbing resin (D), is determined by weight loss after 3-hour drying at a temperature of 180° C.), provided that the water-absorbing resin (D) is flowable even at room temperatures. The water-absorbing resin (D) is in a particle form, and has the moisture content more preferably in a range of 0.2% to 30% by weight, further preferably in a range of 0.3% to 15% by weight, and especially preferably in a range of 0.5% to 10% by weight. High moisture content would possibly give the water-absorbing resin (D) a poor flowability (particle flowability) and hinder production. Further, the high moisture content would possibly make it impossible to crush the water-absorbing resin and to control the particle size distribution of the water-absorbing resin.

The water-absorbing resin (D) of the present invention may be in particle form, powder form, or particle-shaped dried agglomeration-formed, and may be inconstant in shape and be able to be crushed with ease.

The water-absorbing resin (D) is obtained by crushing with a crushing machine, if necessary. The crushing machine is not particularly limited but the following machines may be used as the crushing machine, for example: a roll-type crushing machine such as a roll mill; a hummer-type crushing machine such as a hummer mill; an impact-shock applying type crushing machine, a cutter mill, a turbo grinder, a ball mill, a flush mill, and the like. Among them, the roll mill is preferable for controlling the particle size distribution. The crushing may be carried out sequentially twice or more (that is, the crushing is carried out sequential two or more stages) in order to control the particle size distribution. It is preferable to carry out the crushing sequentially three times or more (that is, the crushing is carried out sequential three or more stages). The crushing carried out in two or more stages may be performed by using the same crushing machine for the stages, or by using different crushing machines in each stage.

The crushed water-absorbing resin may be classified with a sieve of a particular mesh size, in order to give the water-absorbing resin (D) a particular particle size distribution. There is no particular limit in terms of a classifier. For example, the classifier may be a vibrating sieve (unbalance weight driving type, resonance type, vibrating mortar type, electromagnetic type, circular vibrating type, or the like) an in-surface moving sieve (horizontal movement type, horizontal circular-linear movement type, three-dimensional movement type, or the like), a movable net type sieve, forced stirring type sieve, net-surface vibrating type sieve, a wind-force sieve, a sonic wave sieve, or the like. The vibrating sieve and the in-surface moving sieve are preferable. In order to obtain the water-absorbing resin (D) of the present invention, the mesh size of the sieve is preferably in a range of 1000 μm to 300 μm, more preferably in a range of 900 μm to 400 μm, and most preferably in a range of 710 μm to 450 μm. Sieves out of the range would possibly fail to give the particle size distribution to the water-absorbing resin (D). It is preferable to use two or more sieves having different mesh sizes.

In order to give the water-absorbing resin (D) of the present invention the particular particle size distribution, further classification may be performed so as to remove part or all of particles having a diameter less than a particular diameter. In this step, there is no particular limit in terms of the classifier. For example, the classifiers exemplified above can be used preferably. In addition to the classified, particulate-type classifiers (centrifugal force type, inertial force type and the like), and the like may be used. This step removes part or all of the particles having a diameter preferably less than 200 μm, more preferably less than 150 μm, and most preferably less than 106 μm, in order to obtain the water-absorbing resin (D) of the present invention.

Moreover, the present invention may be so arranged that the particles removed (removed fine particles) by the classification are recycled and transformed, for example by agglomeration, to larger particles or particle-shape agglomerations, so as to be used as the water-absorbing resin (D) of the present invention. The recycling of the removed fine particles may be carried out by well-known arts such as a method in which a warm water and fine powder of a water-absorbing resin are mixed and then dried (U.S. Pat. No. 6,228,930), a method in which fine powder of a water-absorbing resin and a monomer aqueous solution are mixed and then polymerization is carried out; a method in which water is added to fine powder of a water-absorbing resin and agglomeration is carried out with a surface-pressure equal to or higher than a particular level (European Patent No. 844270); a method in which a fine powder of a water-absorbing resin is wetted sufficiently so as to form an amorphous gel, and then the amorphous gel is dried and crushed (U.S. Pat. No. 4,950,692); a method in which fine powder of the water-absorbing resin and a polymerization gel are mixed (U.S. Pat. No. 5,478,879), and the like method. The method in which a warm water and fine powder of a water-absorbing resin are mixed and then dried is preferable. Moreover, the recycled water-absorbing resin may be used as the water-absorbing resin (D) of the present invention, or may be returned to the pulverizing step (that is, the pulverizing step may be repeated with the recycled water-absorbing resin). In order to attain the targeted water-absorbing resin (D), the recycled particles are preferably returned to the pulverizing step. The thus recycled water-absorbing resin has a porous structure substantially. A ratio of the recycled water-absorbing resin in the water-absorbing resin (D) of the present invention is preferably 30% by weight or lower, more preferably 20% by weight or lower, and most preferably 10% by weight or lower.

The water-absorbing resin thus obtained is arbitrarily adjusted in terms of its properties such as absorbency (CRCs) for 0.9 wt % saline is preferably in a range of 15 g/g to 45 g/g, more preferably in a range of 20 g/g to 45 g/g, further preferably in a range of 20 g/g to 40 g/g, further more preferably in a range of 25 g/g to 40 g/g, and most preferably in a range of 28 g/g to 40 g/g. The properties such as the absorbency are arbitrarily adjusted according to a purpose (usage) of the water-absorbing resin. However, in case CRCs is less than 15 g/g or more than 45 g/g, there is a possibility that the water absorbent of the present invention cannot be obtained.

The water-absorbing resin (D) thus obtained has a cross-linked structure and has the water-soluble content of preferably 25% by weight or lower, more preferably 20% by weight or lower, further preferably 15% by weight or lower, and especially preferably 10% by weight or lower. The water-soluble content of the water-soluble resin (D) is measured by a method later described.

The water-absorbing resin (D) of the present invention is preferably arranged to have such particle size distribution that particles less than 850 μm and not less than 106 μm in diameter share 90% to 100% by weight in the total of water-absorbing resin (D). The water-absorbing resin (D) of the present invention is more preferably arranged to have such particle size distribution that particles less than 850 μm and not less than 150 μm in diameter share 90% to 100% by weight in the total of water-absorbing resin (D). The water-absorbing resin (D) of the present invention is further preferably arranged to have such particle size distribution that the particles less than 850 μm and not less than 106 μm in diameter share 95% to 100% by weight in the total of water-absorbing resin (D). The water-absorbing resin (D) of the present invention is preferably arranged to have such particle size distribution that the particles less than 850 μm and not less than 150 μm in diameter in is 95% to 100% by weight in the total of water-absorbing resin (D). If the content of the particles less than 850 μm and not less than 106 μm in diameter is less than 90% by weight, the water-absorbing resin (D) would possibly contain too much dust (become dusty), thereby deteriorating liquid permeability and diffusibility of the resultant water absorbent.

The water-absorbing resin (D) of the present invention is preferably in a particle form having a weight-average particle diameter in a range of 100 μm to 600 μm, more preferably in a particle form having a weight-average particle diameter in a range of 200 μm to 500 μm, and most preferably in a particle form having a weight-average particle diameter in a range of 250 μm to 450 μm. If the weight average particle diameter was less than 100 μm, the resultant water absorbent would possibly become difficult to handle, and would possibly be dusty and poor in liquid permeability and diffusibility. If the weight average particle diameter was more than 600 μm, the resultant absorbent would possibly be susceptible to damages and become easy to deteriorate in property.

A logarithmic standard deviation (σζ) of the particle size distribution of the water-absorbing resin (D) of the present invention is preferably in a range of 0.25 to 0.45, more preferably in a range of 0.27 to 0.43, and further preferably in a range of 0.30 to 0.40. The logarithmic standard deviation (σζ) of the particle size distribution indicates how wide the particle size distribution is. A smaller logarithmic standard deviation (σζ) of the particle size distribution indicates the particle size distribution is narrower. That is, if the logarithmic standard deviation (σζ) was larger than 0.45, the particle size distribution would be too wide. Thus, the resultant water absorbent would become difficult to handle and poor in the liquid permeability and diffusibility. If the logarithmic standard deviation (σζ) was less than 0.25, productivity would be significantly deteriorated. Thus, there would be a case that an effect thus obtained is not worthwhile with respect to the cost needed.

As described above, it is preferable that the water-absorbing resin (D) of the present invention satisfy the following requirements (a) and (b):

(a) 0.90% by weight or more of the particles has a diameter less than 850 μm and not less than 150 μm; and (b) logarithmic standard deviation (σζ) of the particles size distribution is in a range of 0.25 to 0.45.

(1-5) Water-Absorbing Resin Particles (E)

The water-absorbing resin particles (E) (Particles (E) of water-absorbing resin) for use in the present invention are obtained preferably by cross-linking a surface of the thus obtained water-absorbing resin (D), with a particular surface cross-linking agent (that is, surface cross-linking of the water-absorbing resin (D) with the particular surface cross-linking agent).

Preferably, the surface cross-linking is carried out so as to attain CRCs not less than 15 g/g but less than 39 g/g, and/or AAPs of 20 g/g or more. Moreover, the surface cross-linking is carried out until a difference between the water-absorbing resin (D) and the water-absorbing resin particles (E) in terms of CRCs becomes preferably 3 g/g or more, and more preferably 5 g/g or more. If the difference between the water-absorbing resin (D) and the water-absorbing resin particles (E) in terms of CRCs was less than 3 g/g, the resultant water absorbent would possibly have insufficient AAPs and SFC.

Examples of the surface cross-linking agent suitably applicable in the present invention include a compound having at least two functional groups that are reactive with a functional group of the water-absorbing resin (D). Functional groups that undergo, with carboxyl group, dehydration reaction or ester interchange are preferable as the functional groups of the compound. Anionic dissociation groups are preferable as the functional groups of the compound, whereas carboxyl group is more preferable as the functional groups of the compound.

Examples of the surface cross-linking agent include: polyhydroxy alcohols such as ethyleneglycol, diethyleneglycol, propyleneglycol, triethyleneglycol, tetraethyleneglycol, polyethyleneglycol, 1,3-propanediol, dipropyleneglycol, 2,2,4-trimethyl-1,3-pentanediol, polypropyleneglycol, glycerin, polyglycerin, 2-butene-1,4-diol, 1,3-butanediol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, oxyethylene-oxypropylene block copolymer, pentaerythritol, sorbitol, and the like; epoxy compounds such as ethyleneglycoldiglycidylether, polyethylenediglycidylether, glycerolpolyglycidylether, diglycerolpolyglycidylether, polyglycerolpolyglycidylether, propylene glycoldiglycidylether, polypropyleneglycoldiglycidylether, glycidol, and the like; multivalent compounds such as ethylenediamine, diethylenetriamine, triethylenetetramine, tetraethylenepentamine, pentaethylenehexamine, polyethyleneimine and the like, and their inorganic or organic salts (for example, azitinium salts and the like); multivalent isocyanate compounds such as 2,4-tolylenediisocyanate, hexamethylenediisocyanate, and the like; aziridine compounds such as polyaziridine and the like; multivalent oxazoline compounds such as 1,2-ethylenebisoxazoline, bisoxazoline, and the like; carbonic acid derivatives such as urea, thio urea, guanidine, dicyandiamide, 2-oxazolidinon, and the like; alkylene carbonate compounds such as 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one, 1,3-dioxopan-2-one, and the like; haloepoxy compounds such as epichlorohydrin, α-methyl epichlorohydrin, and the like, and their multivalent addition compounds with amine (for example, Kymene (Registered Trademark) made by Hercules Inc.); oxetane compounds; oxazolidones such as 2-oxazolidone; silane binding agents such as γ-glycidoxypropyltrimethoxysilane, γ-aminopropyltriethoxysilane, and the like; and the like. They may be used solely or in combination.

Moreover, an amount of the surface cross-linking agent to use is in a range of 0.001 parts to 10 parts by weight, and preferably in a range of 0.01 parts to 5 parts by weight, with respect to 100 parts by weight of the water-absorbing resin (D). The amount of the surface cross-linking agent exceeding 10 parts by weight is not economical because the property attained is not in balance with the amount of the surface cross-linking agent added. Further, the amount of the surface cross-linking agent exceeding 10 parts by weight result in a large amount of residual surface cross-linking agent left unused after the surface treatment. Therefore, the amount of the surface cross-linking agent exceeding 10 parts by weight is not preferable. Further, the amount of the surface cross-linking agent is less than 0.001 part by weight would possibly result in insufficient AAPs.

Moreover, in order to speed up the reaction of the surface cross-linking agent and improve the absorbing properties, inorganic acids, organic acids, and polyamino acid and the like described in the publication of European Patent No. 0668080 may be used. Specific examples of the acids include: sulfuric acid, phosphoric acid, hydrochloric acid, citric acid, glyoxylic acid, glycolic acid, glycerophosphoric acid, glutaric acid, cinnamic acid, succinic acid, acetic acid, tartaric acid, lactic acid, pyruvic acid, fumaric acid, propionic acid, 3-hydroxypropionic acid, malonic acid, butyric acid, isobutyric acid, imidino acetic acid, malic acid, isethionic acid, citraconic acid, adipic acid, itaconic acid, crotonic acid, oxalic acid, salicylic acid, gallic acid, sorbic acid, gluconic acid, p-toluenesulfonic acid, and the like. An amount of the acid to use depends on pH and the like of the water-absorbing resin (D), but is preferably in a range of 0 parts to 10 parts by weight, and more preferably in a range of 0.1 parts to 5 parts by weight, with respect to 100 parts by weight of the water-absorbing resin (D).

In the present invention, it is preferable to use water as a solvent in mixing the water-absorbing resin (D) and the surface cross-linking agent. An amount of water to add is preferably more than 0 parts but not more than 20 parts by weight, more preferably in a range of 0.5 parts to 10 parts by weight, and further preferably in a range of 0.5 parts by weight to 5 parts by weight, with respect to 100 parts by weight of a solid parts of the water-absorbing resin (D), even though the amount of water to add depends on the type, particle diameter, and the like of the water-absorbing resin (D).

Moreover, if necessary, a hydrophilic organic solvent may be added as a solvent in mixing the water-absorbing resin (D) and the surface cross-linking agent. Examples of the hydrophilic organic solvent include: lower alcohols such as methyl alcohol, ethyl alcohol, n-propyl alcohol, isopropyl alcohol, n-butyl alcohol, isobutyl alcohol, t-butyl alcohol, and the like; ketones such as acetone and the like; ethers such as dioxane, tetrahydrofuran, alkoxypolyethyleneglycols, and the like; amides such as N,N-dimethylformaldehyde and the like; sulfoxides such as dimethylsulfoxide and the like; and the like. An amount of the hydrophilic organic solvent to add is preferably not more than 20 parts by weight, more preferably not more than 10 parts by weight, and further preferably not more than 5 parts by weight, with respect to 100 parts by weight of a solid parts of the water-absorbing resin (D), even though the amount of water to add depends on the type, particle diameter, and the like of the water-absorbing resin (D). However, it is most preferable not to use organic solvents, for the sake of safety and the like.

Moreover, in order to more uniformly mix the water-absorbing resin (D) and the surface cross-linking agent, the mixing of the water-absorbing resin (D) and the surface cross-linking agent may be carried out in the presence of a non-cross-linking water-soluble inorganic salt and/or a non-reducing alkali metal salt pH buffer. The non-cross-linking water-soluble inorganic salt is preferably an alkali metal salt, an ammonium salt, an alkali metal hydroxide, ammonia, hydroxide of ammonia, or the like. The non-reducing alkali metal salt pH buffer is preferably a hydrogen carbonate, dihydrogenphosphate, hydrogen phosphate, or the like. An amount of the non-cross-linking water-soluble inorganic salt and/or non-reducing alkali metal salt pH buffer to add is preferably in a range of 0.005 parts to 10 parts by weight, and more preferably in a range of 0.05 parts to 5 parts by weight, with respect to 100 parts by weight of a solid parts of the water-absorbing resin (D), even though the amount of water to add depends on the type, particle diameter, and the like of the water-absorbing resin (D).

The surface cross-linking agent may be added, for example, after the water-absorbing resin (D) is dispersed in the hydrophilic organic solvent. However, if necessary, it is preferable that an solution of the surface cross-linking agent be prepared by dissolving or dispersing the surface cross-linking agent in water and/or the hydrophilic solvent, and then mixing the solution, and then the solution of the surface cross-linking agent be added to the water-absorbing resin (D) by directly spraying or dropping the solution onto the water-absorbing resin (D). Moreover, in the case where water is used in the mixing, the mixing may be carried out in the presence of a water-insoluble inorganic particle powder, a water-soluble multivalent metal salt, a surfactant and/or the like.

A mixing apparatus for use in mixing the water-absorbing resin (D) and the surface cross-linking agent has preferably a large mixing power, in order to uniformly and surely mix them. The mixing apparatus may be, for example, a circular-tube type mixing apparatus, a double-wall circular cone type mixing apparatus, a V-shape type mixing apparatus, a ribbon type mixing apparatus, a screw type mixing apparatus, a fluidized furnace rotary desk type mixing apparatus, an air-flow mixing apparatus, a two-armed kneader, an internal mixing apparatus, a pulverizing type kneader, a rotary mixing apparatus, a screw type extruder, a stirring type mixing apparatus, ant the like.

After mixing the water-absorbing resin (D) and the surface cross-linking agent, a resultant mixture thereof is subjected to heat treatment, thereby performing the surface cross-linking of the water-absorbing resin (D). It is preferable that the surface cross-linking be carried out so as to attain CRCs (absorbency for 0.9 wt % saline) of not less than 15 g/g but less than 39 g/g, and/or AAPs (absorbency against pressure for 0.9 wt % saline) of not less than 20 g/g. Duration of the heat treatment in the present invention is preferably in a range of 1 minute to 180 minutes, more preferably in a range of 3 minutes to 120 minutes, and further preferably in a range of 5 minutes to 100 minutes. Heating temperature (temperature of a heating medium) of the heat treatment is preferably in a range of 60° C. to 250° C., more preferably in a range of 100° C. to 210° C., and further preferably in a range of 120° C. to 200° C.

If the heating temperature was less than 60° C., the duration of the heat treatment would be too long, thereby deteriorating the productivity. Further, uniform cross-linking would not be attained. Thereby, it would possibly become impossible to obtain the targeted water absorbent. Moreover, if the heating temperature was more than 250° C., the resultant water-absorbing resin particles (E) would be damaged, thereby making it difficult to obtain the water absorbent excellent in the water absorbency.

The heating treatment may be carried out by using a generally used dryer or a heating furnace. The dryer may be, for example, a trench type mixing dryer, a rotary type dryer, a disk type dryer, a fluidized bed type dryer, an air-flow type dryer, an infrared dryer, or the like. In case where the light radiation treatment is carried out in the present invention instead of the heating treatment, it is preferable to use ultraviolet rays, and the optical polymerization initiator may be used.

It is preferable to cool the water-absorbing resin (D) after heating the water-absorbing resin (D) in the surface treatment step. It is preferable to cool the water-absorbing resin (D) to a temperature in a range of 20° C. to 100° C. A cooling apparatus for use in the cooling may be an apparatus that forms a heat exchanger in combination with the heating apparatus, by utilizing, as a cooling medium, the heating medium used in the heating apparatus.

After those steps, the thus obtained water-absorbing resin particles (E) is preferably subjected to a particle-size regulating step so as to regulate the particle size distribution thereof.

In the water-absorbing resin particles (E) of the present invention, the content of particles less than 850 μm and not less than 150 μm is preferably 90% by weight or more, and more preferably 95% by weight or more. If the content of the particles of this size is less than 90% by weight, the water-absorbing resin particles (E) would be possibly dusty, thereby deteriorating liquid permeability and diffusibility of the resultant water absorbent.

The water-absorbing resin particles (E) of the present invention is preferably in a particle form (particle shape)

having a weight-average particle diameter in a range of 100 μm to 600 μm, more preferably in a particle form having a weight-average particle diameter in a range of 200 μm to 500 μm, and most preferably in a particle form having a weight-average particle diameter in a range of 250 μm to 450 μm. If the weight average particle diameter was less than 100 μm, the resultant water absorbent would possibly become difficult to handle, and would possibly be dusty and poor in liquid permeability and diffusibility. If the weight average particle diameter was more than 600 μm, the resultant absorbent would possibly be susceptible to damages and become easy to deteriorate in property.

A logarithmic standard deviation ($\sigma\zeta$) of the particle size distribution of the water-absorbing resin particles (E) of the present invention is preferably in a range of 0.25 to 0.45, more preferably in a range of 0.27 to 0.43, and further preferably in a range of 0.30 to 0.40. The logarithmic standard deviation ($\sigma\zeta$) of the particle size distribution indicates how wide the particle size distribution is. A smaller logarithmic standard deviation ($\sigma\zeta$) of the particle size distribution indicates the particle size distribution is narrower. That is, if the logarithmic standard deviation ($\sigma\zeta$) was larger than 0.45, the particle size distribution would be too wide. Thus, the resultant water absorbent would become difficult to handle and the liquid permeability and diffusibility. If the logarithmic standard deviation ($\sigma\zeta$) was less than 0.25, productivity would be significantly deteriorated. Thus, there would be a case that an effect thus obtained is not worthwhile with respect to the cost needed.

The method of producing the water-absorbing resin particles (E) according to the present invention may, if necessary, further have the steps of adding a function of various kinds to the water-absorbing resin particles. The addition of the function may be carried out by adding an additive such as: a deodorant, anti-bacterial agent, a perfume material, a foaming agent, a pigment, a dye, a hydrophilic short fiber, a plasticizer, an adhesive, a metal soap, a surfactant, a fertilizer, an oxidant, a reductant, water, a salt, a chelating agent, a microbicide a hydrophilic polymer such as polyethyleneglycol or the like, a hydrophobic polymer such as paraffin or the like, a thermoplastic resin such as polyethylene, polypropylene or the like, a thermosetting resin such as polyester resin, urea resin or the like, or the like additive. An amount of the additive to add is in a range of 0 part to 10 parts by weight, and preferably in a range of 0 part to 1 part by weight, with respect to 100 parts by weight of the water-absorbing resin particles (E).

As described above, it is preferable that the water-absorbing resin particles (E) of the present invention satisfy the following requirements (a) and (b):

(a) 90% by weight or more of the particles has a diameter less than 850 μm and not less than 150 μm; and (b) logarithmic standard deviation ($\sigma\zeta$) of the particles size distribution is in a range of 0.25 to 0.45.

There is no particular limit in the water-absorbing resin particles for use in the present invention, but it is preferable that the water-absorbing resin particles be the water-absorbing resin particles (E) thus obtained by the above method. The water-absorbing resin particles (E) may be utilized as the water absorbent of the present invention. In the case where the water-absorbing resin particles (E) are used as the water absorbent, of the present invention, the water absorbent preferably have the CRCs, AAPs, SFC, CSF, particle size distribution, bulk density, water-soluble content, shape, moisture content, and the like described later in Item (3). However, the water absorbent of the present invention may be prepared by the other method.

(2) Liquid Permeability Improver (F)

The water absorbent of the present invention may be a water-absorbing resin material containing water-absorbing resin particles and a liquid permeability improver. The following explains a liquid permeability improver (F) for use in the present invention.

In the present invention, the liquid permeability improver refers to a substance that improves SFC of water-absorbing resin particles (which are not particularly limited) that contain the substance. Specifically, the liquid permeability improver is a substance that improves SFC of a water absorbent by 1 ($10^{-7} \cdot cm^3 \cdot s \cdot g^{-1}$) or more, and preferably by 5 ($10^{-7} \cdot cm^3 \cdot s \cdot g^{-1}$) or more, the water absorbent being prepared by mixing the liquid permeability improver and the surface-cross-linked water-absorbing resin particles. It is possible to confirm whether or not the substance is the liquid permeability improver, for example, by adding the substance to water-absorbing resin particle (E7) obtained in Example 7 of the present invention, and comparing SFC before and after the addition of the substance. The liquid permeability improver (F) may be contained inside, on surfaces, or in a vicinity of the surfaces of the water-absorbing resin particles. It is preferable that the liquid permeability improver (F) is located on the surface or in the vicinity of the surface. Moreover, the liquid permeability improver (F) may be reacted with a functional group of the water-absorbing resin particles. The addition of the water-absorbing resin particles may be carried out before, after, and/or during the surface treatment. The liquid permeability improver (F) widens gaps between swelled water-absorbing resin particles by acting as a spacer or the like, or by giving ionic surface cross-linking effect, thereby improving the liquid permeability of the water-absorbing resin particles.

The liquid permeability improver (F) for use in the present invention may be, for example, a hydrophilic inorganic compound. Water-insoluble hydrophilic inorganic particulates, water-soluble multivalent metal salt, or the like may be used preferably. The hydrophilic property in the present invention may be, for example, that of hydrophilicity of 70% or more as described in European Patent No. 0629411. In the present invention, a cationic polymer compound (that is exemplified in column 11 of U.S. Pat. No. 5,797,893, for example), hydrophobic inorganic particulates, or the like, which improves the liquid permeability, may be used as the liquid permeability improver (F), but sometime are not preferable because they increase contact angle of the water absorbent and sometimes reduce CSF. A surfactant that reduces surface tension of the water absorbent is not preferable in the present invention, because the surfactant reduces CSF.

In the case where the liquid permeability improver (F) used in the present invention is inorganic particulates, the inorganic particulates have a particle diameter preferably not more than 500 μm, more preferably not more than 300 μm, and most preferably not more than 150 μm, for the sake of easy handling and effective addition. When the particulates are primary particles, the particle diameter refers to a diameter of the primary particles, whereas the particle diameter refers to a diameter of secondary particles (integrated particles or agglomerations (agglomerated particles)). In case where particles of a compound (such as non-agglomerated (primary-particle) silica, alumina or the like) which have a high degree of hardness and are difficult to break by impact force, are used, the primary particles of the agglomerated particles and the granulated particles have a particle diameter of preferably 5 μm or less, more preferably, 1 μm or less, and most preferably, 0.1 μm or less.

Specific examples of the liquid permeability improver (F) for use in the present invention include: ores such as talc, kaolin, fuller's earth, bentonite, activated earth, barite, natural asphaltene, strontium ore, ilmenite, pealite, and the like; aluminum compounds such as aluminum sulfate 14-18 water (or anhydrate thereof), aluminum potassium sulfate 12 water, aluminum sodium sulfate 12 water, aluminum chloride, poly aluminum chloride, aluminum oxide, and the like; other multivalent metal salts; hydrophilic amorphous silica (prepared, for example, by drying method (Tokuyama Reolosil QS-20; by sedimentation method Degussa Ag. Sipernat 22S, Sipernat 2200); a complex of oxide complexes such as silicon oxide, aluminum oxide, and magnesium oxide (eg. Attaagel #50 of Engelhard), a complex of silicon oxide and aluminum oxide, a complex of, silicon oxide, magnesium oxide, and the like; and the like. Moreover, permeability improvers exemplified in U.S. Pat. No. 5,164,459, European Patent No. 761241, and the like may be used in the present invention. Of those particles, the hydrophilic particles (such as aluminum sulfate 14 to 18 water, hydrophilic amorphous silica, and the like) are preferable. However, particles having low hydrophilic property may be treated with a hydrophilic compound to cause surfaces of the particles to be hydrophilic, before use. Those particles may be used solely or two or more kinds of them may be used in combination.

There is no particular limit as to a method of adding the liquid permeability improver (F) for use in the present invention. The addition of the liquid permeability improver (F) may be carried out by adding the liquid permeability improver (F) as an aqueous solution thereof, by adding the liquid permeability improver (F) as a slurry thereof, or by adding the liquid permeability improver (F) as a powder. In addition, the addition of the liquid permeability improver (F) may be carried out, for example, by a method (in which an aqueous solution of a liquid permeability improver is added before the surface treatment) described in Japanese laid-open applications, Nos. 2002-539281 and 2002-538275, by a method (in which a liquid permeability improver is dry-blended, and then a bonding agent is added) described in Japanese laid-open application No. 2001-523289, by a method (in which an aqueous solution of a liquid permeability improver is added after the surface treatment) described in Japanese laid-open application No. 2001-523287, or by the like method. Moreover, the addition of the liquid permeability improver (F) may be carried out, for example, by a method in which the liquid permeability improver (F) is added after adding a bonding agent to the water-absorbing resin particles, or by a method in which at least part of the liquid permeability improver (F) is thermally bonded to at least part of a surface of the water-absorbing resin particles. An amount of the liquid permeability improver (F) for use in the present invention is preferably in a range of 0.01% to 10% by weight, and more preferably in a range of 0.05% to 5% by weight, with respect to the water-absorbing resin particles. If the amount of the liquid permeability improver (F) was more than 10% by weight, the absorbency would be reduced, whereas, if the amount was less than 0.01% by weight, there is a risk that the effect of the addition of the liquid permeability improver would not be attained. Moreover, it is possible to adjust the liquid permeability of the water absorbent. A mixing apparatus for use in mixing the liquid permeability improver (F) and the water-absorbing resin particles does not need a large mixing power. For example, they may be mixed with a crushing apparatus, or sieving apparatus. The mixing apparatus may be, for example, a circular-tube type mixing apparatus, a double-wall circular cone type mixing apparatus, a V-shape type mixing apparatus, a ribbon type mixing apparatus, screw type mixing apparatus, a fluidized furnace rotary desk type mixing apparatus, an air-flow mixing apparatus, a two-armed kneader, an internal mixing apparatus, a pulverizing type kneader, a rotary mixing apparatus, a screw type extruder, a static mixing apparatus, and the like. Moreover, as to timing of the addition, the addition may be performed before, during or after obtaining the water-absorbing resin particles. It is preferable to perform after the surface cross-linking.

The thus obtained water absorbent preferably have the CRCs, AAPs, SFC, CSF, particle size distribution, bulk density, water-soluble content, shape, moisture content, and the like described later in Item (3). However, the water absorbent of the present invention may be prepared by the other method.
(3) Water Absorbent The water absorbent of the present invention is the water-absorbing resin particles or a water-absorbing resin material containing the water-absorbing resin particles (preferably a water-absorbing resin material containing the water-absorbing resin particles and the liquid permeability improver). The water absorbent of the present invention is suitably used as an absorbing material for use in a sanitary/hygienic material, the absorbing material used for absorbing body fluids such as urine, menstrual blood, sweat etc. The water-absorbing resin particles are preferably the particles thus prepared by the method described in (1-5) Water-Absorbing Resin Particles (E). Moreover, the liquid permeability improver is preferably the liquid permeability improver described in Item (2). A ratio of the water-absorbing resin particles contained in the water absorbent of the present invention is in a range of 90% to 100% by weight, preferably in a range of 95% to 100% by weight, and especially preferably in a range of 98% to 100% by weight. Moreover, the water absorbent of the present invention preferably contains phosphorus atom. The phosphorus atom is derived from a phosphorus compound, which is a water-soluble chain transfer agent.

The water-absorbent of the present invention has an excellent gel property. The excellent gel property is attained by having a particular particle size distribution, a particular CRCs, a particular AAPs, and a particular chemical cross-linking index (or chemical cross-linking index against pressure). The conventional polymerization (References 1 to 5) in the present of a chain transfer agent attains a water-absorbing resin having excellent gel durability, but fails to attain a sufficient gel property due to its high absorbency. Moreover, the conventional art fails to recognize the importance of the particle size distribution, which determines the property of the water absorbent. As a result of intensive studies for attaining a water absorbent having an excellent gel property, the inventors of the present invention found that the water absorbent attains the excellent gel property by having the particular CRCs, the particular AAPs, and the particular chemical cross-linking index (or chemical cross-linking index against pressure). There has been no full explanation why the excellent gel property can be attained by arranging as such. However, it is postulated that the use of the chain transfer agent in polymerization can reduce a molecular weight of a main-chain macromolecule in the water-absorbing resin, thereby reducing entanglement (physical entangling) of the main-chain macro molecule, and thus reducing physical cross-linking due to the entanglement. As a result, the resultant water-absorbing resin has a higher absorbency than the case where no chain transfer agent is used. In this case, the decrease in the physical cross-linking due to the reduction in the entanglement can be compensated for by chemical cross-linking by adding a more amount of the internal cross-linking agent. The water-absorbing resin as such has the excellent gel property because the water-absorbing resin has more chemical cross-linking than the water-absorbing resin prepared by an ordinary polymerization. Further, the inventors of the present invention found an index for indicating a degree of the chemical cross-linking, and that the water-absorbent shows the excellent gel property when the water-absorbent has a particular value of the index, a particular particle size distribution, a particular CRCs, and a particular AAPs. The present invention is based on these findings. These particular values of the properties will be later described in detail.

A water absorbent of the present invention is so arranged that, in case where CRCs is not less than 29 g/g but less than 39 g/g, a chemical cross-linking index represented by the following Formula (1) is 160 or more, preferably 170 or more, more preferably 175 or more, and most preferably 180 or more. The chemical cross-linking index has an upper limit of 1000 in general.

$$\text{Chemical Cross-Linking Index} = (CRCs)/(CRCdw) \times 1000 \quad (1),$$

where CRCs(g/g) is an Absorbency for 0.9 wt % saline, and CRCdw(g/g) is an absorbency for deionized water.

A water absorbent of the present invention is so arranged that, in case where CRCs is not less than 15 g/g but less than 29 g/g, a chemical cross-linking index against pressure represented by the following Formula (2) is 100 or more, preferably 110 or more, more preferably 115 or more, and most preferably 120 or more. The chemical cross-linking index against pressure has an upper limit of 1000 in general.

$$\text{Chemical Cross-Linking Index Against Pressure} = (CRCs) \div (AAPdw) \quad (2),$$

where CRCs(g/g) is an absorbency for 0.9 wt % saline, and AAPdw (g/g) is an absorbency against pressure for deionized water.

The chemical cross-linking index, which is a feature of the water absorbent of the present invention, is shown by a ratio between the absorbency for deionized water and the absorbency for 0.9 wt % saline. A higher chemical cross-linking index is attained when the absorbency for deionized water is lower and the absorbency for 0.9 wt % saline is higher. When the absorbent is swelled with water, the physical cross-linking due to the entanglement of the main-chain macromolecules with each other is broken away due to disentanglement of the main-chain macromolecules. However, the swelling is still controlled by the chemical cross-linking. Thus, the water absorbent has a lower absorbency for deionized water when it has more chemical cross-linking. Further, in this case, the water absorbent with more chemical cross-linking has a higher chemical index, among water absorbents having the same absorbency for 0.9 wt % saline. For the same reason, the absorbency for deionized water against pressure is increased when there is more chemical cross-linking in the absorbent. That is, in the deionized water, the physical cross-linking due to the entanglement of the main-chain macromolecules is broken away. So, the water absorbent has a low ability of keeping strength of the gel against pressure. On the other hand, the chemical cross-linking has a high ability of keeping the strength of the gel against pressure. That is, among the water absorbents having the same absorbency for 0.9 wt % saline, the water absorbent with the more chemical cross-linking has a higher chemical cross-linking index against pressure. There are preferable ranges of CRCs of the water absorbent. In the ranges, these two indexes (chemical cross-linking index and the chemical cross-linking index against pressure) are preferably applicable. That is, within a higher range of CRCs (not less than 29 g/g but less than 39 g), the chemical cross-linking index is preferable. Within a lower range of CRCs (not less than 15 g/g but less than 29 g/g), the chemical cross-linking index against pressure is preferable. This is because, within the respective preferably ranges, the differences in the properties indicated by the indexes are more distinctive.

The water absorbent of the present invention is arranged in terms of the particle size distribution, such that 90% by weight or more of the particles have a diameter less than 850 μm but not less than 150 μm. It is preferable that 95% or more by weight of the particles have a diameter less than 850 μm but not less than 106 μm. It is more preferable that 95% or more by weight of the particles have a diameter less than 850 μm but not less than 150 μm. An upper limit of the ratio of the particles having this diameter is 100% by weight. If the content of the particles of this size is less than 90% by weight, the water-absorbing resin (D) would be possibly dusty, thereby deteriorating liquid permeability and diffusibility of the resultant water absorbent.

The water absorbent of the present invention is in a particle form having weight-average diameter is preferably in a range of 100 μm to 600 μm, more preferably in range of 200 μm to 500 μm, and most preferably in a range of 250 μm to 450 μm. If the weight average particle diameter was less than 100 μm, the resultant water absorbent would possibly become difficult to handle, and would possibly be dusty and poor in liquid permeability and diffusibility. If the weight average particle diameter was more than 600 μm, the resultant absorbent would possibly be susceptible to damages and become easy to deteriorate in property.

A logarithmic standard deviation ($\sigma\zeta$) of the particle size distribution of the water absorbent of the present invention is preferably in a range of 0.25 to 0.45, more preferably in a range of 0.27 to 0.43, and further preferably in a range of 0.30 to 0.40. The logarithmic standard deviation ($\sigma\zeta$) of the particle size distribution indicates how wide the particle size distribution is. A smaller logarithmic standard deviation ($\sigma\zeta$) of the particle size distribution indicates the particle size distribution is narrower. That is, if the logarithmic standard deviation ($\sigma\zeta$) was larger than 0.45, the particle size distribution would be too wide. Thus, the resultant water absorbent would become difficult to handle and the liquid permeability and diffusibility. If the logarithmic standard deviation ($\sigma\zeta$) was less than 0.25, productivity would be significantly deteriorated. Thus, there would be a case that an effect thus obtained is not worthwhile with respect to the cost needed.

As described above, it is preferable that the water absorbent of the present invention satisfy the following requirements (a) and (b):

(a) 90% by weight or more of the particles has a diameter less than 850 μm and not less than 150 μm; and (b) logarithmic standard deviation ($\sigma\zeta$) of the particles size distribution is in a range of 0.25 to 0.45.

The water absorbent of the present invention has CRCs (absorbency for 0.9 wt % saline) not less than 15 g/g but less than 39 g/g, preferably in a range of 20 to 35 g/g, more preferably in a range of 20 to 32 g/g and further preferably in a range of 24 to 32 g/g. A water absorbent with an absorbency (CRCs) lower than these ranges is inefficient for use in the sanitary materials such as diaper, and a water absorbent with an absorbency (CRCs) higher than these ranges would possibly cause property deterioration due to reductions in the gel strength.

In the water absorbent of the present invention, the absorbency against pressure (AAPs) for 0.9 wt % saline is 20 g/g or more, preferably 22 g/g or more, and more preferably 23 g/g or more, and most preferably 24 g/g or more. In general, an upper limit of AAPs is 100. If AAPs for 0.9 wt % saline is less than 20 g/g, the water absorbent would possibly have insufficient gel property that does not allow the water absorbent to be efficiently used as the water absorbent for the paper diaper and the like.

The water absorbent of the present invention has SFC for 0.69 wt % saline, of preferably in a range of 30 to 3000 ($10^{-7} \cdot cm^3 \cdot s \cdot g^{-1}$), more preferably in a range of 50 to 2000 ($10^{-7} \cdot cm^3 \cdot s \cdot g^{-1}$), further preferably in a range of 70 to 1000 ($10^{-7} \cdot cm^3 \cdot s \cdot g^{-1}$), especially preferably in a range of 80 to 300 ($10^{-7} \cdot cm^3 \cdot s \cdot g^{-1}$), more especially preferably in a range of 100 to 250 ($10^{-7} \cdot cm^3 \cdot s \cdot g^{-1}$), and most preferably 100 to 200 ($10^{-7} \cdot cm^3 \cdot s \cdot g^{-1}$).

In general, the SFC for 0.69 wt % saline has an upper limit of 3000. The SFC for 0.69 wt % saline is a figure indicating liquid permeability and diffusibility of a water absorbent. A water absorbent with a higher SFC has better liquid permeability and diffusibility. A higher SFC for 0.69 wt % saline is required for the sanitary material having a higher water absorbent content, even though this depends on how much the water absorbent content is.

The water absorbent of the present invention has CSF (Capillary Suction force) (with a negative pressure gradient of 20 cm) of preferably 15 g/g or more, more preferably 18 g/g or more, and most preferably 20 g/g. CSF indicates how strong a capillary suction force is. A higher CSF is preferable because absorbed liquid can be diffused upwardly with the higher CSF.

The water absorbent of the present invention has water soluble content of preferably 20% by weight or less, more preferably 15% by weight or less, especially preferably 13% by weight or less, and most preferably 10% by weight or less. The water absorbent having the water soluble content of 20% by weight or more would possibly fail to attain the effect of the present invention, and further would have lower properties to be used in the sanitary materials such as the diapers. Moreover, the water soluble content of 20% by weight or more is not preferable in terms of safety. One of the low property is that the polymer component in the water-absorbing resin is dissolved out when the water absorbent is swelled with water, whereby diffusion of the liquid is hindered. It is considered that the dissolved-out polymer component hinders the liquid flowing on the surface of the water-absorbing resin particles. Furthermore, the dissolution of the polymer component would possibly increase viscosity of the absorbed liquid while lowering the CSF. The water-soluble content of the water absorbent is measured by a later-described method.

There is no particular limit in the moisture content of the water absorbent of the present invention. The moisture content of the water absorbent of the present invention is preferably not less than 0% but not more than 50% by weight, more preferably not less than 0.01% but not more than 40% by weight, and further preferably not less than 0.1% but not more than 10% by weight.

There is no particular limit in bulk density of the present invention. The bulk density of the present invention, is preferably in a range of 0.40 g/ml to 0.90 g/ml, and more preferably in a range of 0.50 g/ml to 0.80 g/ml (a method of measuring the bulk density is prescribed in JIS K-3362). If the bulk density was less than 0.4 g/ml or more than 0.90 g/ml, the water absorbent would possibly become susceptible to damages during the production process and have low properties.

Phosphorus compound content in the water absorbent is preferably in a range of 10 ppm to 1% by weight, more preferably in a range of 20 ppm to 5000 ppm, further preferably in a range of 30 ppm to 4000 ppm, and especially preferably in a range of 50 ppm to 3000 ppm, based on phosphorus element, even though the phosphorus compound content depends on the quantity of the water absorbent to be used. The phosphorus compound content as the phosphorus element exceeding 1% by weight is not preferable, because, if so, the water soluble content would be increased thereby giving the water absorbent lower properties. Moreover, if the phosphorus compound content as the phosphorus element was less than 10 ppm, chain transfer ability would be too low to attain the target water absorbent sometimes.

Further, these water absorbents are preferably arranged to contain a liquid permeability improver of 0.001 parts to 5 parts by weight with respect to 100 parts by weight of the particles (particles of water-absorbing resin).

Moreover, in addition to the water-absorbing resin particles (E) and/or the liquid permeability improver (F), the absorbent of the present invention may contain an additive thereby having a function of various kinds. The additive may be, for example: a deodorant; anti-bacterial agent, a perfume material, a foaming agent, a pigment, a dye, a hydrophilic short fiber, a plasticizer, an adhesive, a metal soap, a surfactant, a fertilizer, an oxidant, a reductant, water, a salt, a chelating agent, a microbicide a hydrophilic polymer such as polyethyleneglycol or the like, a hydrophobic polymer such as paraffin or the like, a thermoplastic resin such as polyethylene, polypropylene or the like, a thermosetting resin such as polyester resin, urea resin or the like, or the like additive. An amount of the additive to be added is less than 10% by weight, preferably less than 5% by weight, more preferably less than 1% by weight, with respect to the weight of the water absorbent.

The use of the water absorbent of the present invention gives the sanitary material an excellent gel property. Therefore, if the absorbing material of the diaper or the like contains the water absorbent of the present invention in high content, the absorbing material can absorb urine or a body fluid more than twice because the urine or the body fluid applied to the absorbing material can be diffused inside the absorbing material, which provides the urine or the body fluid a room to be absorbed.

(4) Producing Method of Water Absorbing Material, and its Water Absorbing Properties A combination an appropriate material and the water absorbent thus prepared by the above method can be used as a water-absorbing material suitable as a water-absorbing layer of the sanitary material. The following explains the water-absorbing material according to the present invention.

The water-absorbing material of the present invention is a material made of the water-absorbent and the other material, and formed in a shape. The water-absorbing material is used for the sanitary/hygienic material such as paper diapers, sanitary napkins, incontinent pads, medical-use pads, and the like for absorbing blood, body fluid, urine, or the like. An example of the other material used in combination with the water absorbent is a cellulose fiber. Specific examples of the cellulose fiber are: mechanical pulp made from woods; chemical pulps; wood pulp fibers such as soluble pulps and the like; artificial cellulose fibers such as rayon, acetates and the like; and the like. The wood pulp fibers are preferable. These cellulose fibers may contain a synthetic fiber, such as nylon, polyester or the like, as part of its components. In the case where the water absorbent of the present invention is used as a component of the water absorbing material, weight of the water absorbent of present invention is preferably 20% or more by weight, more preferably 30% or more by weight, further preferably 40% or more by weight, and most preferably 50% or more by weight. The weight of the water absorbent of less than 20% by weight in the water-absorbing material would possibly be ineffective.

For obtaining the water-absorbing material by using the thus prepared water absorbent and the cellulose fiber, for example, the following well-known methods may be adopted arbitrarily: a method of obtaining the water-absorbing material by dispersing the water absorbent on a paper sheet or mat made of the cellulose fiber, and if necessary, by disposing (sandwiching) the absorbent between the paper sheets or mats thus prepared; a method of obtaining the water-absorbing material by blending the cellulose fiber and the absorbent uniformly; and the like methods. Preferably, a method of obtaining the water-absorbing material by dry-mixing the water absorbent and the cellulose fiber to obtain a mixture of them, and then compressing the mixture. This method can significantly inhibit fall-out of the water absorbent from the cellulose fiber. It is preferable that the compression be carried out while heating the mixture. The heating is carried out, for example, in a range of 50° C. to 200° C. Moreover, method described in the following publication may be suitably applied to obtain the water-absorbing material: Japanese laid-open application, Tokukaihyo, publication No. 9-509591 (a water-absorbing material containing a mixture of a water-absorbing resin, and a water-absorbing improved polymer reactive with at least one component contained in urine). Japanese laid-open Patent Application, publication No. 9-290000 (a water-absorbing material comprising a water-absorbing resin, a poly cation polymer, a glue fine fiber, and a supporting layer, the poly cation polymer bound with the water-absorbing resin on a surface thereof, the glue fine fiber dispersed in the water-absorbing resin, and the glue fine fiber bound with the water-absorbing resin via the glue fine fiber); Japanese Laid-Open Patent Application, publication No. 10-265582 (75 parts by weight of the water absorbent and 25 parts by weight of wood crushing pulp are dry-mixed by using a mixer, so as to obtain a mixture thereof. The mixture is, then, applied onto a wire screen of 400 mesh (mesh size of 38 μm) by using air flow by using a batch-type aerial application web-maker, so as to form a web of 120 mm×350 mm in size. After that the web is pressured with pressure of 2 kg/cm² for 5 seconds so as to obtain a water-absorbing material of 500 g/m². Then, a back sheet (liquid impermeable sheet), the water-absorbing material, and a top sheet (liquid permeable sheet) are combined together in this order by using a both-side sticky tape, the back sheet made of liquid impermeable polypropylene and having a so-called leg gather, and the top sheet made of liquid permeable polypropylene. Thereby a lamination material is obtained. So-called tow tape fasteners are attached to the lamination material, thereby obtaining a water-absorbing product (that is, paper diaper)).

The water absorbent of the present invention thus obtained gives the water-absorbing material an excellent absorption amount, an excellent liquid absorbing rate, an excellent dry-touch feeling against pressure after absorption, and an excellent stability of a swelled gel thereof for 16 hours or longer since the beginning of the swelling.

Furthermore, these excellent water absorbing properties allow the water absorbent to be used as water retaining agent for various usages, for example: water-retaining agents for absorbing goods such as sanitary napkins, incontinent pads, medical-use pads, and the like; water retaining agents for agriculture/horticulture uses, such as peat-moss (sphagnum), soil conditioners, water retaining agents, agricultural effect keeping agents, and the like; water retaining agents for construction/civil engineering usages, such as dew preventing agents, additives for cement, and the like; release controlling agents, cold insulating agents, disposable body warmers, sludge coagulating agents, freshness keeping materials, ion exchange column materials, dehydrating agents for sludge/oil, desiccating agents, humidity conditioning agents and the like; and the like. Moreover, the water absorbent obtained according to the present invention is especially suitable for the use in the sanitary material (such as sanitary napkin) for absorbing fecal, urine, and/or bloods.

In the case where the water absorbing material of the present invention is used in the sanitary material for the sanitary napkins, incontinent pads, medical-use pads, or the like, it is preferable that the water absorbing material be used in such an arrangement that (c) the water absorbing material is disposed between (a) a liquid-permeable top sheet provided next to a body of a user, and (b) a liquid-impermeable back sheet provided next to clothes of the user but far from the body of the user. The water-absorbent may be multi-layered (two or more layers). Further, the water absorbent may be used in combination of a pulp layer or the like.

It is preferable that the water absorbent used in the water-absorbing material have the properties as described above in the Item (3).

Specifically, a sanitary material according to the present invention, comprises (a) a liquid-permeable top sheet provided next to a body of a user, (b) a liquid-impermeable back sheet provided next to clothes of the user but far from the body of the user, and (c) a water absorbing material disposed therebetween, wherein: the water absorbing material includes a water absorbent by 20% or more by weight, preferably 30% or more by weight, more preferably 40% or more by weight, and most preferably 50% or more by weight, the water absorbent containing water-absorbing resin particles, which are surface cross-linked and prepared from a water-absorbing resin having a cross-linked structure prepared by polymerizing a monomer including at least acrylic acid and/or its salt, the water absorbent satisfying:

(a) 90% by weight or more of the particles have a diameter less than 850 μm but not less than 150 μm;

(b) a logarithmic standard deviation ($\sigma\zeta$) of the particle size distribution is in a range of 0.25 to 0.45;

(c) AAPs for 0.9 wt % saline is 20 g/g or more;

(d) CRCs for 0.9 wt % saline is not less than 29 g/g but less than 39 g/g;)

(e) a chemical cross-linking index is 160 or more, the chemical cross-linking index represented by Formula (1):

$$\text{Chemical Cross-Linking Index}=(CRCs)/(CRCdw)\times 1000 \qquad (1),$$

where CRCs(g/g) is an absorbency for 0.9 wt % saline, and CRCdw(g/g) is an absorbency for deionized water.

Specifically, a sanitary material according to the present invention, comprises (a) a liquid-permeable top sheet provided next to a body of a user, (b) a liquid-impermeable back sheet provided next to clothes of the user but far from the body of the user, and (c) a water absorbing material disposed therebetween, wherein: the water absorbing material includes a water absorbent by 20% or more by weight, preferably 30% or more by weight, more preferably 40% or more by weight, and most preferably 50% or more by weight, the water absorbent containing water-absorbing resin particles, which are surface cross-linked and prepared from a water-absorbing resin having a cross-linked structure prepared by polymerizing a monomer including at least acrylic acid and/or its salt, the water absorbent satisfying:

(a) 90% by weight or more of the particles have a diameter less than 850 μm but not less than 150 μm;

(b) a logarithmic standard deviation ($\sigma\zeta$) of the particle size distribution is in a range of 0.25 to 0.45;

(c) AAPs for 0.9 wt % saline is 20 g/g or more;

(f) CRCs for 0.9 wt % saline is not less than 15 g/g but less than 29 g/g;

(g) a chemical cross-linking index against pressure is 100 or more, the chemical cross-linking index against pressure represented by Formula (2):

$$\text{Chemical Cross-Linking Index Against Pressure} = (CRCs) + (AAPdw) \quad (2),$$

where CRCs(g/g) is an absorbency for 0.9 wt % saline, and AAPdw (g/g) is an absorbency against pressure for deionized water.

[Second Embodiment]

The following describes another embodiment of the present invention.

In the present embodiment, a water-absorbing resin is a water-swelling cross-linked polymer prepared by polymerization, drying, and then crushing, but have not been surface-treated with a surface cross-linking agent of various kinds. Further, in the present embodiment, a water absorbent contains water-absorbing resin particles whose surfaces have been cross-linked with the cross-linking agent (hereinafter, such water-absorbing resin particles sometime referred to as surface-treated water-absorbing resin particles), and may contains another component such as a liquid permeability improver or the like.

Content of the surface-treated water-absorbing resin particles in the water absorbent is preferably in a range of 80 to 100% by weight, more preferably in a range of 90% to 100% by weight, and more preferably in a range of 95% to 100% by weight (The surface-treated water-absorbing resin particles have a moisture content of 10% by weight or less).

(1) Water-Absorbing Resin and Polymerization Thereof

In the present embodiment, examples of a monomer component polymerizable to be the water-absorbing resin include the monomer components described in the first embodiment.

Moreover, examples of an internal cross-linking agent applicable to the present invention include the internal cross-linking agents described in the first embodiment. An amount of an internal cross-linking agent is, with respect to the monomer (excluding the internal cross-linking agent), preferably in a range of 0.10 mol % to 0.5 mol %, and especially preferably in a range of 0.20 mol % to 0.40 mol %. If the amount of the internal cross-linking agent was less than 0.001 mol %, or was more than 2 mol %, there is a possibility that the sufficient absorbing properties would not be attained.

Examples of a polymerization initiator applicable to the first embodiment include the polymerization initiators described in the first embodiment. However, persulfate is preferable because it reduces the cost and an amount of the residual monomer after polymerization. Moreover, an amount of the polymerization initiator in the present embodiment may be similar to that in the first embodiment.

Moreover, the polymerization may be started by radiating an active energy rays such as radiation rays, electron rays, ultraviolet rays, or the like. Further, the polymerization may be started by using the active energy rays in combination with the polymerization initiator. Note that the reaction temperature of polymerization described in the first embodiment is applicable as a reaction temperature of the polymerization in the present embodiment.

The polymerization may be carried out with an additive added to the reaction system. Examples of the additive include: hydrophilic polymers (such as starch, starch derivatives, cellulose, cellulose derivatives, polyvinyl alcohols, polyacrylic acid (salts), polyacrylic acid (salt)-based cross linking material, and the like), chelating agent, and the like. An amount of the additive to add is in a range of 0 part to 10 parts by weight, and preferably in a range of 0 part to 1.0 part by weight, with respect to 100 parts by weight of the water absorbent.

In order to attain the waver-absorbing resin for use in the present invention, the polymerization of the monomer is carried out by a specific method. Conventionally, Japanese Patent Application, Tokukai, Publication No. 2002-212204, discloses an economical aqueous polymerization by which a water-absorbing resin having an excellent quality is obtained with a low cost. However, it is expected that in this method a swelling pressure of a gel layer would be reduced due to high monomer concentration and reduction in an amount of the cross-linking agent contributing the cross-linking in the case of the production of the water-absorbing resin with the desirable low cost. As a result of diligent studies, the inventors of the present invention found out that the water-absorbing resin having the excellent swelling pressure of the gel layer can be obtained by polymerization carried out with a specific monomer concentration range and a maximum polymerization temperature of over 100° C.

Specifically, the concentration of the monomer component to be polymerized to be the water-absorbing resin in the present invention is preferably in a range of 30% to 60% by weight, more preferably in a range of 30% to 45% by weight, further preferably in a range of 30% to 40% by weight, and especially preferably in a range of 30% to 35% by weight. Concentration less than 30% by weight results in low productivity, while concentration more than 60% by weight lowers the swelling pressure of the gel layer of the water absorbing resin.

The higher swelling pressure of the gel layer can be attained when this polymerization method is carried out with the specific monomer concentration, because more amount of the cross-linking agent can contribute to the cross-linking. It is well known fact that the liquid absorbency is reduced when the amount of the cross-linking agent contributing the cross-linking is increased. In the present invention, on the contrary, it is possible to attain a water-absorbing resin having a high retention ability and high swelling pressure of the gel layer, even if the more amount of cross-linking agent is added and contributes to the cross-linking.

This phenomenon has not been well explained yet. However, from the fact that the water-absorbing resin of the present invention has a high liquid retention ability even if a large amount of the cross-linking agent is added, it is deduced that the water-absorbing resin has such cross-linked structure that is wholly more uniform and thus suitable for liquid retention. Such cross-linked structure gives high liquid retention ability to the water-absorbing resin.

Based on this, the swelling pressure of the gel layer of the water-absorbing resin of the present invention is further improved by using, in addition, a water-soluble chain transfer agent for keeping a molecular weight of the main chain at a certain level. Thereby, it is further ensured that the water-absorbing resin have the properties of the present inventions.

The water-soluble chain transfer agents described in the first embodiment are applicable as the water-soluble chain transfer agent for use in the present embodiment.

Moreover, in the present embodiment an amount of the water-soluble chain transfer agent to add is similar to that of the first embodiment.

There is no particular limit in neutralization of an acid group-containing monomer. For usages in which the water-absorbing resin or water absorbent may be in contact with human body, such as in the sanitary goods, the neutralization is preferably in a range of 50 mol % to 100 mol %, more preferably in a range of 50 mol % to 80 mol %, further preferably in a range of 55 mol % to 78 mol %, and most preferably in a range of 60 mol % to 75 mol %.

In case where acrylic acid is neutralized with an alkali, it is preferable to effectively utilize heat of neutralization and/or heat of dissolution (of acrylic acid and the alkali) in order to increase a monomer aqueous solution. It is preferable that polymerization be started by adding the cross-linking agent and the polymerization initiator into the monomer aqueous solution heated by the heat of neutralization in an insulated condition. It is also preferable that, as later described, the heat of neutralization and/or the heat of dissociation (of acrylic acid and the alkali) be utilized for removing dissolved oxygen.

The polymerization of the monomer component may be carried out by the bulk polymerization or the sedimentation polymerization. However, because of the resultant property, easy control, and further absorbing properties of the resultant swelled gel, it is preferable to perform the polymerization by the reverse-phased suspension polymerization and the aqueous polymerization in which an aqueous solution of the monomer is used. The aqueous polymerization is especially preferable. The aqueous polymerization is not particularly limited to a specific method. A static polymerization in which a monomer aqueous solution is polymerized in a static state, a stirring polymerization in which polymerization is carried out in a stirring apparatus.

It is preferable to use an endless belt in the static polymerization. The belt is preferably made of such a resin or rubber that makes it difficult for polymerization heat to escape via that surface of the belt which is in contact with the materials for polymerization.

In the stirring polymerization, a single-armed stirring apparatus may be used, but a multiple-armed stirring apparatus is preferably used.

In radical aqueous polymerization, dissolved oxygen is removed generally by introducing an inert gas into a reactor or reducing pressure inside the reactor to exhaust the reactor. Accordingly, facility and operating cost for the removal of the dissolved oxygen is required in the polymerization in reality. It is preferable that the removal of the dissolved oxygen be carried out by heating the monomer aqueous solution and evaporating off the dissolved oxygen by utilizing the heat of neutralization and/or the heat of dissociation (of acrylic acid and the alkali). If the heating by the neutralization and/or the heat of dissociation is not sufficient for heating the monomer aqueous solution to evaporate off the dissolved oxygen therefrom, it is preferable to preheat each component (monomer aqueous solution and/or an alkali solution, and/or deionized water) before adding them together.

It is more preferable that the raw materials of the monomer aqueous solution, namely acrylic acid, alkali aqueous solution, water, and the like, be heated up by the neutralization without performing the removal of dissolved oxygen, so as to attain a dissolved oxygen amount of preferably 4 ppm or less, more preferably 2 ppm or less, and most preferably 1 ppm or less, with respect to the monomer aqueous solution. The polymerization may be carried out with the thus prepared raw materials, without performing the removal of dissolved oxygen.

It is also preferable that the dissolved oxygen be partially removed from one, some, or all of the raw materials (acrylic acid, alkali aqueous solution, water, and the like) of the monomer aqueous solution, and then the dissolved oxygen be further removed from the raw materials by the heating by the neutralization. Moreover, in an arrangement in which acrylic acid and the alkali are subjected to line-mixing neutralization, then the polymerization initiator is further added by line-mixing, and then the polymerization of is carried out from such high initial polymerization temperature that is 80° C. or above, it is preferable that the dissolved oxygen be not removed from the raw materials (acrylic acid, alkali aqueous solution, water, and the like) of the monomer aqueous solution in advance, so as to prevent the polymerization from starting in line.

The polymerization is generally carried out under normal pressure. However, it is preferable to carry out the polymerization under reduced pressure thereby lowering a boiling point of a polymerization system, so as to perform the polymerization while distilling off water. For easy operation and the like, it is more preferable to perform the polymerization under normal pressure.

It is preferable that temperature of the monomer be increased in advance, because, by doing this, it becomes easier to perform the removal of the dissolved oxygen, and preferred polymerization initiation temperature, which will be discussed below, can be attained in a short time. There is no particular limit in terms of the temperature of the monomer. However, the monomer is heated to a temperature generally not less than 50° C. but not more than a boiling point of the monomer aqueous solution, preferably not less than 60° C. but not more than the boiling point of the monomer aqueous solution, more preferably not less than 70° C. but not more than the boiling point of the monomer aqueous solution, further preferably not less than 80° C. but not more than the boiling point of the monomer aqueous solution, especially preferably not less than 80° C. but not more than 120° C., and most preferably not less than 90° C. but not more than 110° C. If the temperature was less than 50° C., the productivity would be lowered due to longer induction period and longer polymerization period. Further, the property of the water-absorbing resin would be lowered. Note that the polymerization period is a time period from a time when the monomer aqueous solution is added into a polymerization reactor and condition for starting the polymerization is attained, and to a time a peak temperature is reached.

The polymerization initiation temperature is generally in a range of 50° C. to 120° C., preferably in a range of 60° C. to 120° C., more preferably in a range of 70° C. to 120° C., further preferably in a range of 80° C. to 110° C., further more preferably in a range of 90° C. to 110° C., especially preferably in a range of 90° C. to 105° C., and most preferably in a range of 90° C. to 100° C. If the polymerization initiation temperature was less than 50° C., the productivity would be lowered due to longer induction period and longer polymerization period. Further, the property of the water-absorbing resin would be lowered. If the polymerization initiation temperature was more than 105° C., foaming and stretching could not be carried out sufficiently. The polymerization initiation temperature can be observed by clouding, an increase in viscosity, and the like change, of the monomer aqueous solution.

In order to attain these temperatures of the monomer aqueous solution, and to initiate the polymerization temperature, it is preferable to utilize the heat of neutralization and/or the heat of dissociation (of acrylic acid and the alkali) generated in the monomer aqueous solution as described above.

One of the features of the present invention is to obtain the polymer by boiling polymerization of a monomer aqueous solution. The "boiling polymerization" is a polymerization during which a temperature maximally reaches a temperature (polymerization maximum temperature) equal to or higher than 100° C. With this arrangement, the water-absorbing resin (water absorbent) of the present invention can be obtained.

The polymerization maximum temperature is preferably in a range of 100° C. to 150° C., more preferably in a range of 100° C. to 130° C., further preferably in a range of 100° C. to 120° C., and most preferably in a range of 100° C. to 115° C. The polymerization maximum temperatures less than 100° C. or above than 150° C. are not preferably because, if so, the properties of the resultant polymer(hydrate polymer, and the water-absorbing resin particles) would be deteriorated.

In the present invention, a temperature difference ΔT between the polymerization initiation temperature and the polymerization maximum temperature is preferably 70° C. or below, more preferably 60° C. or below, further preferably 50° C. or below, further more preferably 40° C. or below, especially preferably 30° C. or below, and most preferably 25° C. or below. The temperature difference ΔT larger than 70° C. is not preferably because, if so, the properties of the resultant polymer(hydrate polymer, and the water-absorbing resin particles) would be deteriorated.

There is no particular limit in terms of polymerization period. However, the polymerization period is preferably 5 minutes or shorter, more preferably 3 minutes or shorter, further preferably 2 minute or shorter, and further more preferably 1 minutes or shorter. Polymerization period longer than 5 minutes is not preferable because, if so, the properties of the resultant polymer (hydrate polymer, and the water-absorbing resin particles) would be deteriorated.

Moreover, the method according to the present invention is characterized in that the polymerization is started and carried out with a high polymerization initiation temperature. It is postulated that, this feature, of the method of the present invention is the reason why water absorbent, water-absorbing materials, and the like prepared according to the method have such high properties. In the case of the polymerization performed under normal pressure, it is preferable that the temperature be 100° C. or above at a rate of polymerization of 40 mol %, and it be still kept at 100° C. or above at a rate of polymerization of 50 mol %. It is more preferable that the temperature be already 100° C. or above at a rate of polymerization of 30 mol %, and it be still kept at 100° C. or above at the rate of polymerization of 50 mol %. It is further preferable that the temperature be already 100° C. or above at a rate of polymerization of 20 mol %, and it be still kept at 100° C. or above at the rate of polymerization of 50 mol %. In the case of the polymerization performed under reduced pressure, it is again preferable that the temperature be already at the boiling temperature or above at the rate of polymerization of 40 mol %, and it be still kept at the boiling temperature or above at the rate of polymerization of 50 mol %. It is more preferable that the temperature be already at the boiling temperature or above at the rate of polymerization of 30 mol %, and it be still kept at the boiling temperature or above at the rate of polymerization of 50 mol %. It is most preferable that the temperature be already at the boiling temperature or above at the rate of polymerization of 20 mol %, and it be still kept at the boiling temperature or above at the rate of polymerization of 50 mol %.

Because such high temperature is reached at such low rate of polymerization, the polymerization is accomplished in a short time (polymerization complete time is short), generally within 10 minutes or less, preferably within 5 minutes or less. Here, the polymerization complete time is from a time when the monomer aqueous solution to which the polymerization initiator is added is added into the polymerization reactor, to a time the hydrate polymer is removed from the polymerization reactor.

In the present invention, it is preferable that the polymerization be carried out while evaporating off moisture so that a ratio (condensation ratio) between solid content of the hydrate polymer thus obtained by the polymerization, and solid content of the monomer aqueous solution will be preferably in a range of 1.10 to 1.50, more preferably in a range of 1.15 to 1.45, and further preferably in a range of 1.25 to 1.40. The condensation ratio of less than 1.10 indicates that the heat generated during, polymerization is not utilized sufficiently. Here, the solid content of the monomer aqueous solution is the monomer and the additive added thereto, except water and the solvent.

The solid content of the hydrate polymer thus obtained by the polymerization is preferably in a rang of 35% to 68% by weight, more preferably in a range of 40% to 60% by weight, further preferably in a range of 40% to 50% by weight. If the solid content of the hydrate polymer was more than 65% by weight, the pulverization would be carried out with a large burden, thus resulting in the property deterioration.

The hydrate polymer is dried and pulverized after fragmented. Hereby, the water-absorbing resin (water absorbing resin before the surface treatment) is obtained.

The hydrate polymer thus obtained according to the present invention may be crushed (fragmented) by using a crusher of meat chopper-type with ease.

The drying of the crushed (pulverized) hydrate polymer may be carried out at a drying temperature similar to that of the first embodiment.

The moisture content of the water-absorbing resin of the present embodiment may be similar to that of the water-absorbing resin (D) of the first embodiment.

The particle size distribution, and the logarithmic standard deviation of the particle size distribution, of the water absorbing resin of the present embodiment may be similar to that of the water-absorbing resin (D) the first embodiment.

By arranging such that the water-absorbing resin of the present invention has the particle size distribution, it is possible to attain the water absorbent of the present invention having the excellent liquid permeability.

(2) Properties and Shape of Water Absorbing Resin

The properties and the shape of the water absorbing resin (particles of water-absorbing resin) of the present embodiment are described below.

The water-absorbing resin is generally in a particle shape having the particle size distribution and the logarithmic standard deviation (σζ) thereof in the ranges mentioned above, that is, such particle size distribution that the particles less than 850 μm but not less than 106 μm shares 90% by weight in the total of the water-absorbing resin, and the logarithmic standard deviation (σζ) thereof is in a range of from 0.25 to 0.45.

Moreover, in the water-absorbing resin, an absorbency (CRCs (Centrifuge Retention Capacity for saline)) for 0.9 wt % saline is preferably similar to that of the water-absorbing resin (D) described in the first embodiment.

Moreover, a swelling pressure (B) of a gel layer of the water-absorbing resin is preferably 35.0 (kdyne/cm$^2$) or more, and more preferably 40.0 (kdyne/cm$^2$) or more, the swelling pressure (B) being measured by a later-described measuring method. If the swelling pressure (B) was less than 35.0 (kdyne/cm$^2$), the instinct gel strength of the interior of the water-absorbing resin would be lowered. This would possibly lead to failure in attaining the target liquid permeability, even if adding a later-described liquid permeability improver after the surface cross-linking of the water-absorbing resin.

(3) Surface Cross-Linking

The water absorbent used in the present embodiment is preferably prepared by surface cross-linking, in the similar manner to that of the first embodiment, the water-absorbing resin prepared by the above method. An amount of the surface cross-linking agent to add in the present embodiment is similar to that of the first embodiment.

(4) Liquid Permeability Improver

The liquid permeability improvers described in the first embodiment are applicable as the liquid permeability improver for use in the present embodiment.

(5) Properties and Shape of Water Absorbent

The properties and shape of the water absorbent of the present embodiment are described below.

The water absorbent of the present embodiment is similar to that of the first embodiment in terms of shape, particle size distribution, logarithmic standard deviation ($\sigma\zeta$) of the particle size distribution, weight-average diameter (D50), absorbency (CRCs) for 0.9 wt % saline, saline flow conductivity (SFC) for 0.69 wt % saline, absorbency against pressure (AAPs) for 0.9 wt % saline, capillary absorbency (capillary suction force) (CSF), water soluble content, moisture content, bulk density, phosphorus compound content, liquid permeability improver content.

Specifically, a particle-shape water absorbent of the present invention contains water-absorbing resin particles, which are surface cross-linked and prepared from a water-absorbing resin prepared by cross-linking polymerization of a monomer including acrylic acid and/or its salt, wherein: CRCs is in a range of 20 g/g to 32 g/g; AAPs is 22 g/g or more; SFC is in a range of 80 to 300 ($10^{-7} \cdot cm^3 \cdot s \cdot g^{-1}$); the particles has such a particle size distribution that 95% to 100% by weight of the particles have a diameter less than 850 μm but not less than 106 μm; and a logarithmic standard deviation ($\sigma\zeta$) of the particle size distribution is in a range of 0.25 to 0.45. It is preferable that this novel water absorbent contain a chain transfer. It is also preferable that a polymer of this novel water absorbent contain a phosphorus compound.

Moreover, the water absorbent of the present invention containing the liquid permeability improver is preferably such that every one percent by weight of the liquid permeability improver to the surface cross-linked water-absorbing resin particles, increases, at a rate (Increasing Rate of SFC; hereinafter IRS) of 3.5 times or more, SFC for the sodium chloride solution of 0.69% by weight. The IRS is preferably 4 times or more, more preferably 6.0 times or more, and further preferably 8.0 times or more. IRS less than 3.5 times is not preferable because the more amount of the liquid permeability improver (such as the inorganic particulates or the like) is required to attain the high liquid permeability.

In the present invention, the water soluble content of 15% by weight would possibly lead to failure in attaining the effect of the present invention. Further, the water soluble content of 15% by weight would possibly result in lower properties of the water absorbing material in which the water absorbent is used.

(6) Usage of Water Absorbent

The water absorbent of the present invention is preferably used in the sanitary/hygienic material such as paper diapers, sanitary napkins, incontinent pads, the medical-use pads, and the like. The water absorbing material is prepared, for example, by forming a sheet or the like including the water absorbent and a fiber material. The water absorbing material contains the water absorbent according to the present invention, in such a high concentration as 10% by weight or more, and preferably 20% by weight or more. The water-absorbing material is preferably used with such an arrangement that the water-absorbing material is disposed between a liquid permeable top sheet and a liquid impermeable back sheet. The water-absorbing material may be multi-layered (two or more layers). Further, the water-absorbing material may be used in combination with a pulp layer or the like.

The use of the water absorbent according to the present invention gives the sanitary/hygienic material an excellent diffusibility for an aqueous solution due to the addition of the liquid permeability improver to the surface cross-linked water-absorbing resin. Further, because the swelling pressure of the gel layer of the water-absorbing resin is excellent before the water-absorbing resin is surface cross-linked, the use of the water absorbent according to the present invention make it difficult to cause, in the sanitary/hygienic material, the gel blocking after swelling. Therefore, if the absorbing material of the diaper or the like contains the water absorbent of the present invention in high content, the absorbing material can absorb urine or a body fluid more than twice because the urine or the body fluid applied to the absorbing material can be diffused inside the absorbing material, which provides the urine or the body fluid a room to be absorbed. Furthermore, the water-absorbing resin particles prepared from the water-absorbing resin (particles of water-absorbing resin) by surface cross-linking has an excellent IRS according to the amount of the liquid permeability improver to be added. Thus, the desirable liquid permeability can be attained with a smaller amount of the liquid permeability improver. With this arrangement, it is possible to prevent foaming in the production line, clogging of exhaust vent, and to reduce the amount of the inorganic particulates or the like. Thus, it is possible to provide a water-absorbing resin having a high liquid permeability and the excellent safety.

The following will explain the present invention in more detail with reference to Examples and Comparative Examples, but the present invention is not limited to the Examples described herein. Properties of water-absorbing resins, water-absorbing resin particles, and water absorbents were measured by following methods. Following measurements were carried out at a room temperature (23° C.±2° C.) and under humidity of 50RH %, unless otherwise specified. Moreover, in the following measurement methods, the water absorbent was used as an actual example, but the same measurement methods are applicable to the water-absorbing resins and the water-absorbing resin particles.

Note that, in case of the water absorbent that has been used in a final product such as a sanitary/hygienic material, the water absorbent has absorbed moisture. Therefore, the measurement was carried out after the water absorbent which was separated from the final product was dried under reduced pressure and at a low temperature (for example, dried for 12 hours under the reduced pressure of less than 1 mmHg and at the low temperature of 60° C.). Note that, a moisture content ratio of the water absorbent used in the Examples and the Comparative Examples of the present invention was less than 6 wt %.

(1) Absorbency for 0.9 wt % Saline (CRCs)

The absorbency for the 0.90 wt % saline (CRCs) here is an absorbency measured after immersing a sample in the 0.90 wt % saline for 30 minutes without applying pressure thereon. In the present invention, the absorbency (CRCs) for 0.9 wt % saline has the same meaning as absorbency under no pressure.

First, 0.20 g of the water-absorbing resin or the water absorbent was evenly put into a pouch (85 mm×60 mm) made of nonwoven fabric (Trade name: Heatron Paper, Type:GSP-22 produced by Nangoku pulp Kogyo Co., Ltd.). After being sealed, the pouch was immersed in an excessive amount (normally, about 500 ml) of the 0.9 wt % saline at the room temperature (in case of measuring CRCs of the water-absorbing resin, the water-absorbing resin which is classified between 300 μm and 500 μm is used. If a sample does not contain the water-absorbing resin whose particle size is in the foregoing particle size range, the sample is used for measurement without classification). The pouch was taken out of the 0.9 wt % saline 30 minutes later, and was centrifuged for 3 minutes by a centrifugal separator (Centrifuge: TypeH-122, produced by KOKUSAN corporation) with a centrifugal force (250G) described in "edana ABSORBENCY II 441.1-99". After that, weight W1 (g) of the pouch was measured. In addition, the same process was carried out with a pouch containing no water-absorbing resin or no water absorbent, and its weight W0 (g) was measured. Then, the absorbency for the 0.90 wt % saline (CRCs) (g/g) was calculated by a following equation using W1 and W0.

Absorbency for 0.9 wt % saline (g/g)=($W1$(g)−$W0$ (g))/(weight(g) of water absorbent)−1

(2) Absorbency for Deionized Water (CRCdw)

The absorbency for the deionized water (CRCdw) here is an absorbency measured by immersing a sample in the deionized water for 30 minutes without applying pressure thereon. Note that, electric conductivity of the deionized water is between 1.0 µS/cm and 2.0 µS/cm at a temperature of 25° C.

0.050 g of the water absorbent was evenly put into a pouch (85 mm×60 mm) made of nonwoven fabric (of the same kind as the pouch used in the measurement of Absorbency (CRCs) for 0.9 wt % saline). After being sealed, the pouch was immersed in an excessive amount (normally, about 500 ml) of the deionized water at the room temperature. The pouch was taken out of the deionized water 30 minutes later, and was centrifuged for 3 minutes by a centrifugal separator (Centrifuge: TypeH-122, produced by KOKUSAN corporation) with a centrifugal force (250G) described in "edana ABSORBENCY II 441.1-99". After that, weight W2 (g) of the pouch was measured. In addition, the same process was carried out with a pouch containing no water absorbent, and its weight W0 (g) was measured. Then, the absorbency for the deionized water (g/g) was calculated by a following equation using W2 and W0.

Absorbency for deionized water=($W2$(g)−$W0$(g))/ (weight(g) of water absorbent)−1

(3) Absorbency Against Pressure for 0.9 wt % Saline (AAPs)

The absorbency against pressure for 0.9 wt % saline (AAPs) here is an absorbency measured by immersing a sample in the 0.90 wt % saline for 60 minutes with pressure of 4.83 kPa applied thereon. The following explains an apparatus and method for measuring the absorbency for the 0.90 wt % saline against pressure (AAPs).

A 400-mesh stainless metal net 101 (mesh size: 38 µm) was fused to a bottom of a plastic supporter cylinder 100 whose internal diameter was 60 mm. 0.90 g of the water absorbent composition was evenly scattered on the net at the room temperature (20° C. to 25° C.) and under the humidity of 50RH %. A piston 103 and a load 104 were mounted in this order on the water absorbent. The piston 103 and the load 104 were provided such that (i) they were adjusted to be able to apply pressure of 4.83 kPa (0.7 psi) evenly to the water absorbent, (ii) those external diameters were slightly less than 60 mm so that there was no gap between those and the supporter cylinder, and (iii) it was possible to smoothly move up and down. Weight Wa (g) of this measuring apparatus was measured.

A glass filter 106 (produced by SOGO RIKAGAKUGARASU SEISAKUSHO, pore diameter: 100 µm to 120 µm) whose diameter was 90 mm was placed inside a petri dish 105 whose diameter was 150 mm, and a 0.90 wt % saline 108 (20° C. to 25° C.) was poured to the petri dish 105 until the 0.90 wt % saline 108 reaches the same level in height as an upper surface of the glass filter. On the glass filter, a piece of filter paper 107 was placed so that the entire surface of the filter paper 107 got wet. The filter paper used here had a diameter of 90 mm (Product Name: (JIS P 3801, No. 2), produced by Advantec Toyo Kaisha, Ltd. 0.26 mm in thickness and capable of retaining particles of 5 µm in diameter). Then, the excess saline was removed.

The above measuring apparatus was mounted on the above wet filter paper, and the liquid was absorbed under load. Moreover, while the water absorbent was swelling, the level of the 0.90 wt % saline 108 was kept at the same level in height as the upper surface of the glass filter 106 by adding the 0.90 wt % saline as needed. One hour later, the measuring apparatus was removed, and its weight Wb (g) was measured. Then, the absorbency (g/g) for the 0.90 wt % saline against pressure was calculated by a following equation using Wa and Wb.

Absorbency (g/g) for 0.90 wt % saline against pressure=($Wb$(g)−$Wa$(g))/(weight of water absorbent (0.90 g))

(4) Absorbency for Deionized Water Against Pressure (AAPdw)

The absorbency for the deionized water against pressure (AAPdw) here is an absorbency measured by immersing a sample in the deionized water for 60 minutes with pressure of 4.83 kPa applied thereon.

AAPdw was obtained by carrying out the same process as (3) (Absorbency for 0.9 wt % saline against pressure (AAPs)) except that, instead of using the 0.90 wt % saline, the deionized water was used as absorbed liquid.

(5) Weight Average Diameter (D50) and Logarithmic Standard Deviation (σζ) of the Particle Size Distribution The water absorbent was classified by sieving with JIS standard sieves whose mesh sizes were 850 µm, 710 µm, 600 µm, 500 µm, 425 µm, 300 µm, 212 µm, 150 µm, 45 µm, and so on. Then, residual percentage R was plotted to a logarithmic probability paper. Thus, the particle diameter corresponding to R=50 wt % was considered as the weight average diameter (D50). Moreover, the logarithmic standard deviation (σζ) of the particle size distribution was expressed by a following equation. The smaller σζ was, the narrower a particle size distribution was.

σζ=0.5×ln($X2/X1$), (where X1 was the particle diameter when R=84.1% and X2 was the particle diameter when R=15.9%).

The classification for the measurement of the weight average diameter (D50) and the logarithmic standard deviation (σζ) of the particle size distribution was carried out as follows. 10.0 g of the water absorbent was put into JIS standard sieves (THE IIDA TESTING SIEVE: Diameter of 8 cm) whose mesh sizes were 850 µm, 710 µm, 600 µm, 500 µm, 425 µm, 300 µm, 212 µm, 150 µm, 45 µm and so on and classified with a sieve shaker (IIDA SIEVE SHAKER, TYPE: ES-65, SER. No. 0501) for five minutes at the room temperature (20° C. to 25° C.) and under the humidity of 50RH %. Note that the logarithmic standard deviation has the same meaning as the logarithmic standard deviation of the particle diameter or the logarithmic standard deviation of the particle size distribution.

(6) Saline Flow Conductivity of 0.69 wt % Saline (SFC)

Saline flow conductivity of the 0.69 wt % saline (SFC) is a value showing liquid permeability of the water absorbent which is swelled. The larger the value of SFC, the higher the liquid permeability.

A test was carried out according to Saline Flow Conductivity (SFC) test disclosed in Publication of PCT international patent applications No. 509591/1997.

An apparatus shown in FIG. 1 was used for the test. First, the water absorbent (0.900 g) was evenly spread in a container 40 and swelled with artificial urine for 60 minutes with pressure of 0.3 psi (2.07 kPa). Then, the height of a layer of a gel 44 was recorded. Next, while pressure of 0.3 psi (2.07 kPa) was applied thereon, a 0.69 wt % saline 33 from a tank 31 with a constant hydrostatic pressure was flowed through the gel layer thus swelled. This SFC test was carried out at the room temperature (20° C. to 25° C.). As a function of time, an amount of the liquid which flowed through the gel layer was recorded every 20 seconds for 10 minutes by using a computer and a scale. Flow speed Fs(T) of the liquid which flowed through the swelled gel 44 (mainly, between the particles) was determined in a unit of g/s by dividing increasing weight (g) by increasing time (s). Ts was a period of time in which the constant hydrostatic pressure and stable flow speed were obtained. By only using Ts and data obtained during the ten minutes, Fs(T=0), that is, initial flow speed of the liquid which passed through the gel layer was calculated. Fs(T=0) was calculated by extrapolating into T=0 the result of least-squares method of Fs(T) against time.

$$\text{Saline flow conductivity of 0.69 wt \% saline}(SFC)= \\ (Fs(T=0)\times L0)/(\rho\times A\times\Delta P)=(Fs(T=0)\times L0)/139506$$

where

Fs(T=0): flow speed expressed by g/s,

L0: height of the gel layer expressed by cm,

P: concentration of NaCl solution (1.003 g/cm$^3$),

A: area of an upper side of the gel layer in a cell 41 (28.27 cm$^2$), $\Delta P$: hydrostatic pressure applied to the gel layer (4920 dyne/cm$^2$), and Unit of SFC value: ($10^{-7}$ cm$^3$s$^{-1}$).

The apparatus shown in FIG. 1 is arranged as follows. A glass tube 32 was inserted into the tank 31, and a lower end of the glass tube 32 was located such that the height level of the 0.69 wt % saline 33 in the cell 41 was kept to be 5 cm above a bottom of the swelled gel 44 in the cell 41. The 0.69 wt % saline 33 in the tank 31 was supplied to the cell 41 through an L-shaped tube 34 with a cock. Under the cell 41, a container 48 was provided to collect the liquid passed through the cell 41, and the collecting container 48 was placed on an even balance 49. An internal diameter of the cell 41 was 6 cm and a No. 400 stainless metal net 42 (mesh size: 38 µm) was provided on a bottom of the container 40. The piston 46 had a hole 47 at its lower portion, the hole 47 was sufficiently large to allow a liquid to pass there through. At a bottom of the piston 46, a glass filter 45 having high transmittance was provided to cover the hole 47 so that the water absorbent and its swelled gel would not go into the hole 47. The cell 41 was placed on a stand for the cell, and a surface which contacts with the cell 41 was a stainless metal net 43 which could not prevent the liquid from transmitting.

Artificial urine (1) used here was a mixture of 0.25 g of dihydrate of calcium chloride, 2.0 g of potassium chloride, 0.50 g of hexahydrate of magnesium chloride, 2.0 g of sodium sulfate, 0.85 g of ammonium dihydrogen phosphate, 0.15 g of diammonium hydrogenphosphate, and 994.25 g of the deionized water.

(7) Capillary Suction Force (CSF)

CSF is an index for capillary suction force of water absorbent.

Figure 2:
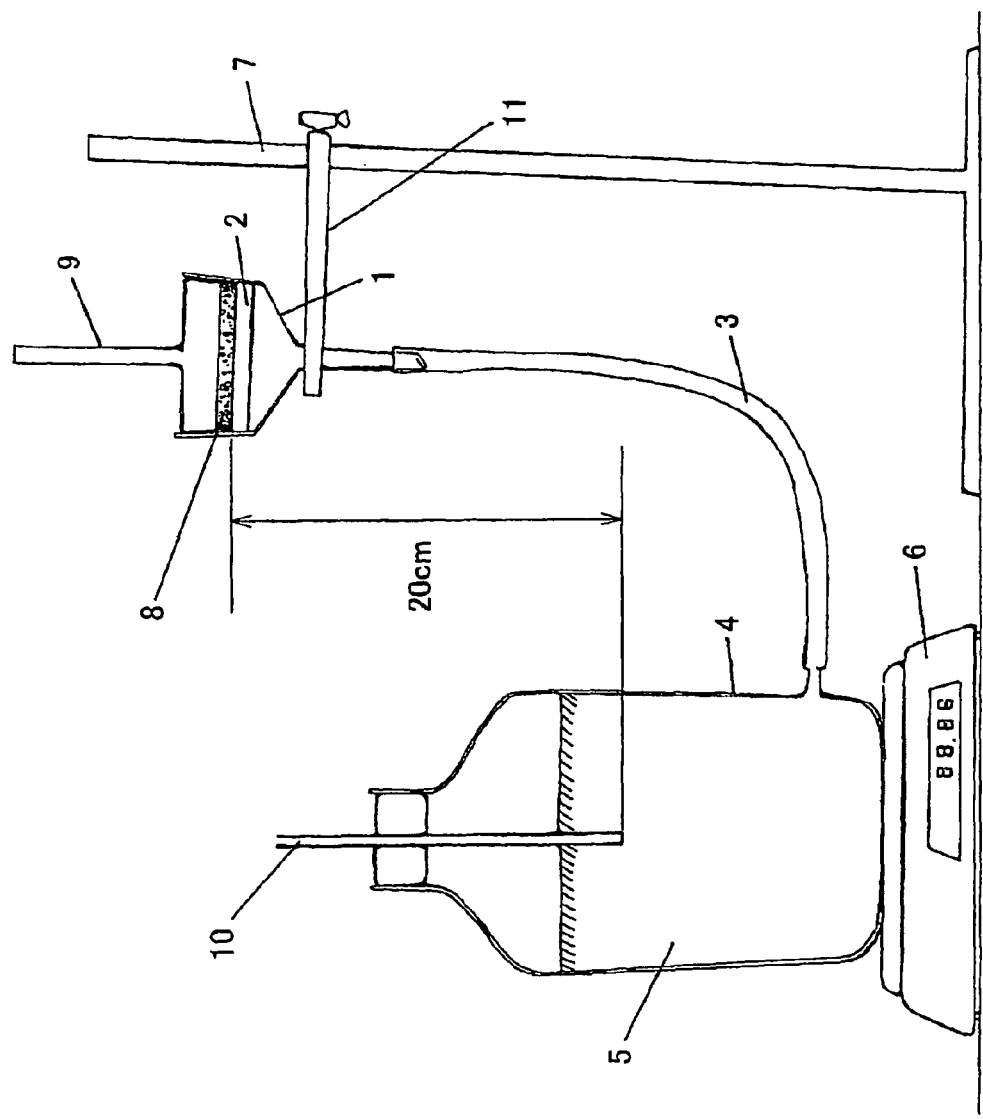
FIG. 2 is a cross sectional view schematically showing a measuring apparatus for use in measurement of capillary absorbency (CSF).
Figure 3:
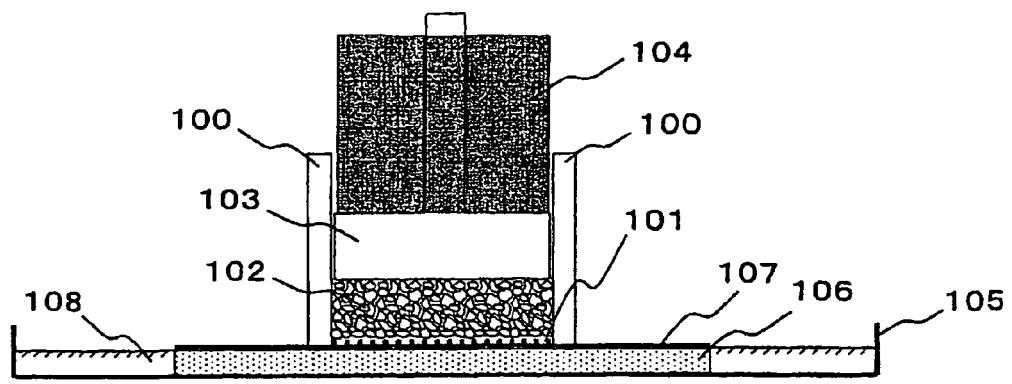
FIG. 3 is a cross-sectional view schematically showing an apparatus for measuring absorbency against pressure (AAPs) for 0.9 wt % saline.
Figure 4:
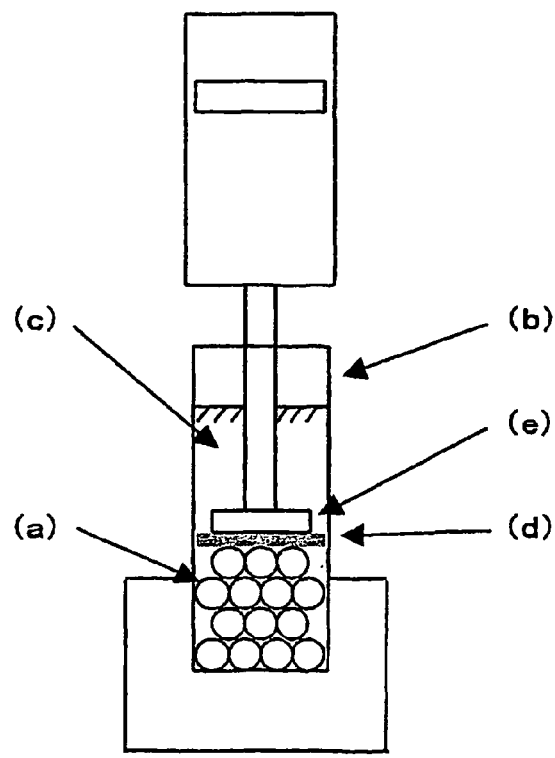
FIG. 4 is a cross-sectional view schematically showing a measuring apparatus for use in measurement of swelling pressure (A) of a gel layer.

CSF of the present invention was a liquid absorption capacity of absorption body, measured within a predetermined time, under load of 0.06 psi (0.41 kPa) applied thereon, and with a negative pressure gradient of 20 cm. The following explains an apparatus and method for measuring CSF with reference to FIG. 2.

1. A tube 3 was connected to a lower part of a glass filter 1 whose diameter was 60 cm, and the tube 3 was also connected to an opening provided at a lower part of a liquid container 4 whose diameter was 10 cm. The glass filter 1 had a liquid absorption surface which was a porous glass plate 2 (glass filter particle #3; Buccaneer type filter TOP17G-3 (code No. 1175-03) produced by SOGO RIKAGAKUGARASU SEI-SAKUSHO). The average pore size of the porous glass plate 2 of the glass filter 1 was in a range of 20 µm to 30 µm. Even if the gap of the liquid levels in height was 60 cm, its capillary force made it possible to keep water inside the porous glass plate against the pressure from the water column, thereby preventing air from entering. The glass filter 1 was attached to a supporter ring 11 which was for adjusting the height, 0.9 wt % saline 5 was filled in the apparatus, and the liquid container 4 was mounted on a scale 6. After checking that there was no air in the tube and in a portion under the porous glass plate 2 of the glass filter 1, the glass filter 1 was fixed to a stand 7 such that the liquid level of the 0.9 wt % saline 5 in the liquid container 4 was higher than the upper surface of the porous glass plate 2 by 20 cm.

2. 0.44 g of a measurement sample 8 (water absorbent) was quickly and evenly scattered on the porous glass plate 2 (on the glass filter in a funnel), and a load 9 whose diameter was 59 mm (0.06 psi (0.41 kPa)) was mounted on the measurement sample 8. 30 minutes later, a value (W20) of the 0.9 wt % saline absorbed in the measurement sample 8 was measured. CSF was obtained by a following equation:

$$CSF\, D1\text{ (g/g) when the vertical interval was 20 cm} \\ = \text{absorbing amount }(W20)(g)/0.44(g)$$

(8) Soluble Content (Water Soluble Content)

184.3 g of the 0.9 wt % saline was poured in a 250 ml plastic container with a cover, and 1.00 g of the water-absorbing resin or the water absorbent was added thereto. The saline was stirred by a stirrer for 16 hours. As a result, a soluble content in the resin was extracted to prepare an extraction liquid. This extraction liquid was passed through a filter paper (Product Name: JIS P 3801, No. 2), produced by Advantec Toyo Kaisha, Ltd. 0.26 mm in thickness and capable of retaining particles of 5 µm in diameter) in order to obtain a filtrate. 50 g of the filtrate was used as a measurement solution.

First, the 0.90 wt % saline was titrated by using NaOH aqueous solution of 0.1N until pH10 was obtained. After that, the 0.90 wt % saline was titrated by using HCl aqueous solution of 0.1N until pH2.7 was obtained. In this way, controls ([bNaOH]ml, [bHCl]ml) were obtained.

The measurement solution was titrated in the same way as above in order to obtain titer ([NaOH]ml, [HCl]ml).

In case of the water absorbent which was composed of a known amount of an acrylic acid and its sodium salt, it was possible to calculate the soluble content in the water-absorbing resin by a following equation based on average molecular weight of a monomer of the water absorbent and the titer obtained above. In case of the water absorbent which was composed of an unknown amount of acrylic acid and its sodium salt, the average molecular weight of a monomer of the water absorbent was calculated by using a neutralization ratio obtained by the titration.

$$\text{Soluble content (wt \%)}=0.1\times(\text{average molecular weight})\times184.3\times100\times([HCl]-[bHCl])/1000/1.0/50.0$$

$$\text{Neutralization ratio (mol \%)}=(1-([NaOH]-[bNaOH])/([HCl]-[bHCl]))\times100$$

(9) Evaluation Method of Water-Absorbing Body

Water-absorbing body using the water absorbent of the present invention was evaluated by a following method.

Referring to a method disclosed in Japanese Patent Publication 10-265582 (corresponding to U.S. Pat. No. 6,110, 992), a water-absorbing body sandwiched between a liquid permeability top sheet and a liquid impermeability back sheet was prepared. Weight of the water absorbent, of the present invention, in the water-absorbing body was more than 50 wt %. The evaluation of the water-absorbing body was carried out by absorbing adult urine which was diluted by 3 times. The water-absorbing body was evaluated on a scale of 1 to 5 in terms of four points such as absorbing amount, liquid absorbing rate, dryness of absorbed water-absorbing body against pressure, and stability of the gel swelled 16 hours before. The standard of the 1-to-5 scale was as follows.

5: very good
4: good
3: average
2: bad
1: very bad

The sum of the scores of the above four points was a comprehensive evaluation score which showed properties of each water absorbent. The higher the evaluation score was, the more excellent the water-absorbing body was.

(10) Swelling Pressure of Gel Layer (SPGL)

Measurement was carried out by a following method using a measuring apparatus (Accuforce Cadnet Force Gage X5931C (Digital Force Gage), produced by AMETEK). 0.358 g of water-absorbing resin (a) classified to have a diameter in a range between 300 μm and 500 μm was put into a cell (b) that was for use in FISHER ELECTRO-PHOTOMETER, and the above-mentioned artificial urine (1) (c) whose temperature was adjusted to 25° C. was poured into the cell (b) (for a sample of a water-absorbing resin particles whose sizes are out of the foregoing particle size range, the measurement is carried out without subjecting the sample to classification). A lid (d) made of polyethylene was immediately placed on a surface of the artificial urine so that the lid would be floated in the artificial urine in the cell (b). By using a lifting/lowering lever and control knob, a load/measurement supporter stick (e) having a round plate whose diameter was 20 mm was adjusted to be in contact with the lid (d). Next, 10 g of the artificial urine (c) was further added. After a gel layer of the water-absorbing resin was swelled to reach the lid (d), the measurement was carried out for 30 minutes. A maximal value which was obtained in the above 30-minute measurement was used to calculate SPGL. SPGL(A) was calculated by a following equation:

$SPGL(A)[kdyne/cm^2]$=Value [g] measured by Force Gage×981 [cm·s−2]/3.14 [cm$^2$]/1000.

Figure 5:
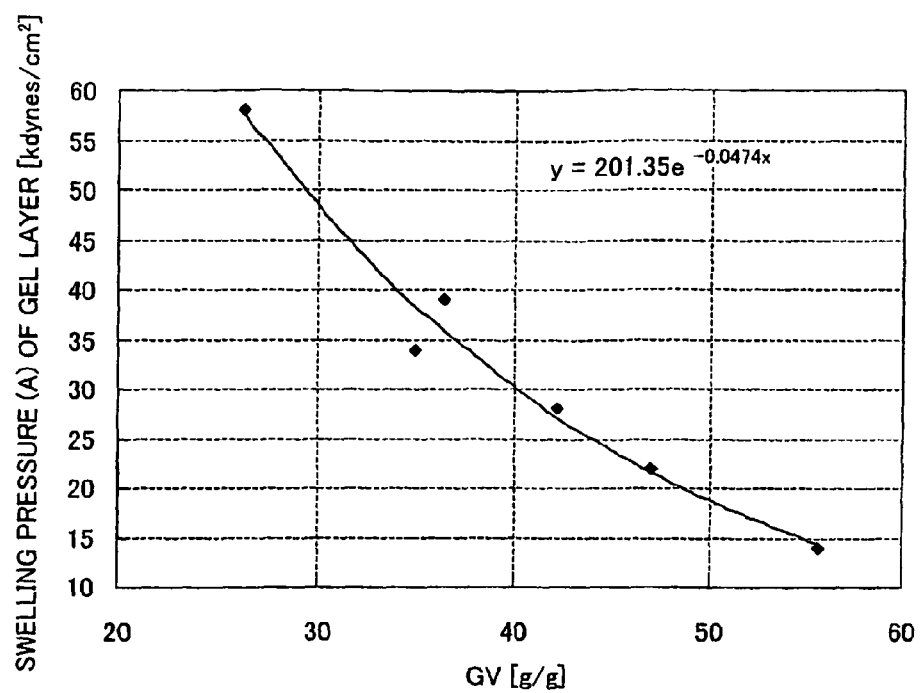
FIG. 5 is a graph showing a relationship between measured swelling pressure (A) of a gel layer and CRCs, of a water absorbing resin.

Here, a value of SPGL(A) was a value which was converted by the above equation from a measured value (load [g]) to a force per unit area. As shown in FIG. 5, the value of SPGL(A) depended heavily on the absorbency for 0.9 wt % saline (CRCs) of the sample used in the measurement. Therefore, for water-absorbing resins having different CRCs values, it is not easy to judge which one of the water-absorbing resins is superior or inferior, by using the value of SPGL(A). By using a relational equation (approximate equation), which was experimentally obtained from FIG. 5, of CRCs and SPGL(A), comparison of SPGL was carried out for the samples of the CRCs having the same CRCs (the data in FIG. 5 are the measured values of the water-absorbing resins, which were obtained by the same polymerization method as in a Comparative Example 14 (as will be described later), in which the polymerization was carried out with 39 wt % of monomer concentration, 71.3 mmol % of a neutralization ratio, and various amounts of a cross-linking agent ranging from 0.02 and 0.20. (Table 16)). SPGL(B), which is a converted value when CRCs=40 [g/g], was calculated by using a following conversion equation:

$SPGL(B)[kdyne/cm^2]$=201.35×$e$([ln($SPGL(A)$/ 201.35)]/$CRCs$×40)

Here, ln(SPGL(A)/201.35) showed a naturalized logarithm of (SPGL(A)/201.35).

In following Examples, the value of SPGL is SPGL(B) which is a converted value when CRCs=40 [g/g].

(11) Increasing Rate of SFC (IRS) per 1 wt % of Liquid Permeability Improver

SFC(A) and SFC(B) were measured in order to calculate IRS by using a following equation. Note that, SFC(A) was SFC of the surface cross-linked water-absorbing resin particles, to which the liquid-permeability improver was not yet added. Moreover, SFC(B) was SFC of the water absorbent to which the liquid-permeability improver was added:

Increasing rate of $SFC(IRS)$ per 1 wt % of liquid permeability improver=($SFC(B)$−$SFC(A)$)/($SFC(A)$/ (wt % of liquid permeability improver used)

Note that, in the case where the liquid-permeability improver is added in the form of an aqueous solution, (wt % of liquid-permeability improver used) described here is calculated based on weight of a compound (for example, a multivalent metal compound) dissolved in the aqueous solution.

(12) Measurement of Concentration of Solid Content in Hydrate Polymer

A smaller portion of the hydrate polymer taken out of a polymerizing vessel was cut off, and was cooled down quickly, and then fragmented with a pair of scissors. 5 g of the thus prepared fragmented hydrate polymer was put onto a petri dish whose internal diameter was 50 mm. The hydrate polymer was dried in a stationary drier at a 180° C. for 12 hours. In this way, solid content in the hydrate polymer was calculated.

Solid content (wt %)=Weight of dried hydrate polymer (g)/Weight of undried hydrate polymer (g)× 100

(13) Calculation of Condensation Ratio

A ratio (Condensation Ratio) is a ratio of the solid content in the hydrate polymer generated by the polymerization to the solid content in a monomer aqueous solution. The solid content in the monomer aqueous solution was a monomer and another additive, and do not include water or solvents. If the solid content in the monomer aqueous solution was 40 wt % and the solid content in the hydrate polymer generated was 48 wt %, the condensation ratio=48/40=1.20.

(a) Polymerization and Surface Treatment

EXAMPLE 1

In a reactor vessel which was composed of a lid and a twin-arm type stainless kneader (content volume of 10 liters) jacketed and provided with two sigma blades, a reaction liquid was prepared by dissolving 11.9 g (0.1 mol %) of polyethyleneglycol diacrylate and 3.65 g of disodium hydrogenphosphite pentahydrate in 5432 g of an aqueous solution of sodium acrylic acid (a sodium acrylic acid aqueous solution). The aqueous solution had monomer concentration of 39 wt % and a neutralization ratio of 71 mol %. Then, the reaction liquid was deaerated for 30 minutes under a nitrogen gas atmosphere. Then, 29.36 g of a 10 wt % sodium persulfate aqueous solution and 24.47 g of a 0.1 wt % L-ascorbic acid aqueous solution were added to the reaction liquid with stirring. About one minute later, polymerization started. The polymerization was carried out at a temperature in a range of 20° C. to 95° C. while crushing gels generated via the polymerization. After 30 minutes from the start of the polymerization, a hydrogel cross-linked polymer was removed from the reactor vessel.

The hydrogel cross-linked polymer thus obtained had were in a form (shape) of small pieces having a diameter of less than or equal to about 5 mm. The small pieces of hydrogel cross-linked polymer were spread (scattered) on a 50-mesh metal wire (mesh size: 300 μm), and was dried by hot air of 180° C. for 50 minutes. The water-absorbing resin obtained was crushed (pulverized) with a roll mill and classified with JIS standard sieves of mesh sizes of 600 μm and 150 μm so as to adjust a particle size distribution of the water-absorbing resin. In this way, water-absorbing resin (D1) was obtained. CRCs of the water-absorbing resin (D1) obtained was 35.2 g/g. 100 g of the hydrogel cross-linked polymer was mixed with an aqueous solution which contained 1.0 g of ethylene glycol and 2.5 g of the deionized water. The mixture was subjected to a heat treatment by which the mixture was kept at 210° C. for 20 minutes. After that, the mixture was cooled down to 60° C. After that, the mixture was passed through the JIS standard sieve whose mesh size was 600 μm in order to obtain the water-absorbing resin particles (E1). The water-absorbing resin particles (E1) thus obtained was regarded as the water absorbent (1).

EXAMPLE 2

The polymerization and the drying were carried out in the same way described in the Example 1 except that, instead of using the reaction liquid described in the Example 1, a reaction liquid was prepared by dissolving 11.9 g (0.1 mol %) of polyethyleneglycol diacrylate and 18.23 g of disodium hydrogenphosphite pentahydrate in 5416 g of a sodium acrylic acid aqueous solution (39 wt % of monomer concentration) having the neutralization ratio of 71 mol %. The water-absorbing resin obtained was pulverized with the roll mill and was classified with JIS standard sieves whose mesh sizes were 710 μm and 150 μm, so as to adjust the particle size distribution of the water-absorbing resin. In this way, water-absorbing resin (D2) was obtained. CRCs of the water-absorbing resin (D2) obtained was 39.4 g/g. 100 g of the water-absorbing resin (D2) was mixed with an aqueous solution which contained 0.5 g of 2-oxazolidone, 0.5 g of propylene glycol, and 3.0 g of the deionized water. The mixture was subjected to a heat treatment by which the mixture was kept at 200° C. for 30 minutes. After that, the mixture was cooled down to 60° C. After that, the mixture was passed through the JIS standard sieve whose mesh size was 710 μm in order to obtain water-absorbing resin particles (E2). The water-absorbing resin particles (E2) obtained was regarded as the water absorbent (2).

EXAMPLE 3

The polymerization and the drying were carried out in the same way described in the Example 1 except that, instead of using the reaction liquid described in the Example 1, a reaction liquid was prepared by dissolving 11.9 g (0.1 mol %) of polyethyleneglycol diacrylate and 2.19 g of disodium hydrogenphosphite pentahydrate in 5426 g of a sodium acrylic acid aqueous solution (39 wt % of monomer concentration) having the neutralization ratio of 71 mol %. The water-absorbing resin obtained was pulverized with the roll mill and was classified with JIS standard sieves whose mesh sizes were 850 μm and 150 μm, so as to adjust the particle size distribution of the water-absorbing resin. In this way, water-absorbing resin (D3) was obtained. CRCs of the water-absorbing resin (D3) obtained was 32.8 g/g. 100 g of the water-absorbing resin (D3) was mixed with an aqueous solution which contained 1.0 g of 1,4-butanediol and 2.5 g of the deionized water. The mixture was subjected to a heat treatment by which the mixture was kept at 200° C. for 20 minutes. After that, the mixture was cooled down to 60° C. After that, the mixture was passed through the JIS standard sieve whose mesh size was 850 μm in order to obtain water-absorbing resin particles (E3). The water-absorbing resin particles (E3) obtained was regarded as the water absorbent (3).

EXAMPLE 4

An aqueous solution which contained 1.5 g of aluminum sulfate 14-18 water (produced by Asada Chemical Industry Co., Ltd.) and 1.6 g of the deionized water was thoroughly (uniformly) mixed with 100 g of the water-absorbing resin particles (E1) obtained in the Example 1. The mixture was dried at 60° C. for 30 minutes. After that, the mixture was passed through the JIS standard sieve whose mesh size was 600 μm. The composition obtained was regarded as the water absorbent (4).

EXAMPLE 5

2.0 g of a 20 wt % polyvinyl amine aqueous solution and 0.3 g of Reolosil QS-20 (hydrophilic amorphous silica, produced by TOKUYAMA) were thoroughly mixed with 100 g of the water-absorbing resin particles (E2) obtained in the Example 2. The mixture was dried at a temperature of 60° C. for 30 minutes. After that, the mixture was passed through the JIS standard sieve whose mesh size was 710 μm. The composition obtained was regarded as the water absorbent (5).

EXAMPLE 6

1.0 g of aluminum sulfate 14-18 water (weight average diameter of about 150 μm) was thoroughly mixed with 100 g of the water-absorbing resin particles (E3) obtained in the Example 3. The composition obtained was regarded as the water absorbent (6)

COMPARATIVE EXAMPLE 1

The water-absorbing resin (D3) obtained in the Example 3 was regarded as the comparative water absorbent (1).

COMPARATIVE EXAMPLE 2

The polymerization was carried out in the same way described in the Example 1 except that a reaction liquid was prepared by dissolving 4.02 g (0.035 mol %) of polyethyleneglycol diacrylate in 5444 g of a sodium acrylic acid aqueous solution (38 wt % of monomer concentration) having the neutralization ratio of 75 mol %. The water-absorbing resin obtained was pulverized with the roll mill and was classified with JIS standard sieves whose mesh sizes were 710 μm and 150 μm, so as to adjust the particle size distribution of the water-absorbing resin. In this way, comparative water-absorbing resin (2) was obtained. CRCs of the water-absorbing resin (2) obtained was 44.0 g/g. 100 g of the water-absorbing resin (2) was mixed with an aqueous solution which contained 0.5 g of 2-oxazolidone, 0.5 g of propylene glycol, and 3.0 g of the deionized water. The mixture was subjected to a heat treatment by which the mixture was kept at 200° C. for 30 minutes. After that, the mixture was cooled down to 60° C. After that, the mixture was passed through the JIS standard sieve whose mesh size was 710 μm in order to obtain comparative water-absorbing resin particles (2). The comparative water-absorbing resin particles (2) obtained were used as the comparative water absorbent (2).

COMPARATIVE EXAMPLE 3

In a reactor vessel which was composed of a lid and a twin-arm type stainless kneader (content volume of 10 liters) jacketed and provided with two sigma blades, a reaction liquid was prepared by dissolving 5.74 g (0.06 mol %) of polyethyleneglycol diacrylate and 10.6 g of disodium hydrogenphosphite 2.5 hydrate in 5367 g of a sodium acrylic acid aqueous solution (33 wt % of monomer concentration) having the neutralization ratio of 75 mol %. The reaction liquid was deaerated for 30 minutes under a nitrogen gas atmosphere. Then, 12 g of a 20 wt % sodium persulfate aqueous solution and 10 g of a 1 wt % L-ascorbic acid aqueous solution was added to the reaction liquid with stirring. Then, polymerization started. The polymerization was carried out at a temperature of 20° C. to 95° C. while crushing gels generated via the polymerization. After 60 minutes from the start of the polymerization, hydrogel cross-linked polymer was obtained.

The hydrogel cross-linked polymers obtained was comminuted to have a diameter of less than or equal to about 5 mm. The hydrogel cross-linked polymer thus comminuted was spread on a 50-mesh metal wire (mesh size: 300 μm), and was dried by hot air of 160° C. for 60 minutes. The water-absorbing resin obtained was pulverized with a vibrating mill and classified, and the particle size distribution was adjusted. In this way, comparative water-absorbing resin (3) whose diameter was in a range of 75 μm to 850 μm was obtained. CRCs of the comparative water-absorbing resin (3) obtained was 51.0 g/g. 100 g of the comparative water-absorbing resin (3) was mixed with an aqueous solution which contained 0.05 g of ethylene glycol diglycidyl ether, 3.0 g of the deionized water, and 0.75 g of isopropyl alcohol. The mixture was subjected to a heat treatment by which the mixture was kept at 200° C. for 50 minutes in order to obtain comparative water-absorbing resin particles (3). The comparative water-absorbing resin particles (3) obtained was regarded as the water absorbent (3).

COMPARATIVE EXAMPLE 4

The polymerization and drying was carried out using the same reaction liquid described in the Example 3. The water-absorbing resin obtained was pulverized with a hammer mill and was classified with JIS standard sieves whose mesh sizes were 850 μm and 150 μm, and the particle size distribution was not especially adjusted. In this way, comparative water-absorbing resin (4) was obtained. CRCs of the comparative water-absorbing resin (4) obtained was 32.7 g/g. 100 g of the comparative water-absorbing resin (4) was mixed with an aqueous solution which contained 1.0 g of 1,4-butanediol and 2.5 g of the deionized water. The mixture was subjected to a heat treatment by which the mixture was kept at 200° C. for 20 minutes. After that, the mixture was cooled down to 60° C. After that, the mixture was passed through the JIS standard sieve whose mesh size was 850 μm in order to obtain comparative water-absorbing resin particles (4). The comparative water-absorbing resin particles (4) obtained were used as the comparative water absorbent (4).

COMPARATIVE EXAMPLE 5

0.3 g of Reolosil QS-20 (hydrophilic amorphous silica, produced by TOKUYAMA) was thoroughly mixed with 100 g of the comparative water absorbent (1) obtained in the Comparative Example 1. The component obtained was regarded as the comparative water absorbent (5).

COMPARATIVE EXAMPLE 6

1.0 g of aluminum sulfate 14-18 water (weight average diameter of about 150 μm) was thoroughly mixed with 100 g of the comparative water absorbent (2) obtained in the Comparative Example 2. The component obtained was regarded as the comparative water absorbent (6).

COMPARATIVE EXAMPLE 7

1.0 g of aluminum chloride hexahydrate (weight average diameter of about 150 μm) was thoroughly mixed with 100 g of the comparative water absorbent (3) obtained in the Comparative Example 3. The component obtained was regarded as the comparative water absorbent (7).

Table 1 shows properties (ratio of particles whose diameter was greater than or equal to (not less than) 150 μm but less than 850 μm, σζ, CRCs, AAPs, SFC, CRCdw, and chemical cross-linked index) of the water absorbents (1) to (6) obtained in the Examples 1 to 6 and properties of the comparative water, absorbents (1) to (7) obtained in the Comparative Examples 1 to 7. Tables 2 and 3 show particle size distributions.

TABLE 1

| Example No. | Water absorbent or Comparative water absorbent | Ratio of particles whose diameter was not less than 150 μm but less than 850 μm | σζ | CRCs (g/g) | AAPs (g/g) | SFC ($10^{-7} \cdot cm^3 \cdot s \cdot g^{-1}$) | CRCdw (g/g) | Chemical cross-linked index |
|---|---|---|---|---|---|---|---|---|
| Example 1 | Water absorbent (1) | 96.2 | 0.37 | 31.4 | 26.1 | 35 | 170.1 | 184.6 |
| Example 2 | Water absorbent (2) | 95.3 | 0.38 | 34.3 | 24.1 | 7 | 198.2 | 173.1 |
| Example 3 | Water absorbent (3) | 97.5 | 0.40 | 29.3 | 25.2 | 51 | 166.1 | 176.4 |
| Example 4 | Water absorbent (4) | 96.2 | 0.37 | 30.8 | 24.9 | 115 | 169.0 | 182.2 |
| Example 5 | Water absorbent (5) | 95.3 | 0.38 | 34.5 | 22.1 | 29 | 197.0 | 175.1 |
| Example 6 | Water absorbent (6) | 97.5 | 0.40 | 29.3 | 24.2 | 160 | 165.0 | 177.6 |
| Comparative Example 1 | Comparative water absorbent (1) | 97.2 | 0.41 | 32.8 | 9.0 | 0 | 195.9 | 167.4 |
| Comparative Example 2 | Comparative water absorbent (2) | 95.2 | 0.38 | 34.0 | 24.1 | 3 | 259.9 | 130.8 |
| Comparative Example 3 | Comparative water absorbent (3) | 94.4 | 0.45 | 39.0 | 26.0 | 0 | 241.8 | 161.3 |

TABLE 1-continued

| Example No. | Water absorbent or Comparative water absorbent | Ratio of particles whose diameter was not less than 150 μm but less than 850 μm | σζ | CRCs (g/g) | AAPs (g/g) | SFC ($10^{-7} \cdot cm^3 \cdot s \cdot g^{-1}$) | CRCdw (g/g) | Chemical cross-linked index |
|---|---|---|---|---|---|---|---|---|
| Comparative Example 4 | Comparative water absorbent (4) | 89.0 | 0.60 | 29.3 | 22.8 | 18 | 168.4 | 174.0 |
| Comparative Example 5 | Comparative water absorbent (5) | 97.1 | 0.41 | 32.9 | 13.0 | 0 | 194.0 | 169.6 |
| Comparative Example 6 | Comparative water absorbent (6) | 95.1 | 0.38 | 34.2 | 23.2 | 12 | 257.0 | 133.1 |
| Comparative Example 7 | Comparative water absorbent (7) | 94.3 | 0.45 | 39.1 | 25.1 | 0 | 239.0 | 163.6 |

TABLE 2

| | Example No. | | | | | |
|---|---|---|---|---|---|---|
| | 1 | 2 | 3 | 4 | 5 | 6 |
| | Water absorbent | | | | | |
| | (1) | (2) | (3) | (4) | (5) | (6) |
| Greater than or equal to 850 μm (wt %) | 0.0 | 0.0 | 0.0 | 0.0 | 0.0 | 0.0 |
| 850-710 (wt %) | 0.0 | 0.0 | 2.9 | 0.0 | 0.0 | 2.8 |
| 710-600 (wt %) | 0.0 | 6.6 | 28.1 | 0.0 | 6.5 | 28.2 |
| 600-500 (wt %) | 3.1 | 8.7 | 17.2 | 3.0 | 8.8 | 17.1 |
| 500-425 (wt %) | 16.9 | 18.2 | 13.5 | 17 | 18.2 | 13.8 |
| 425-300 (wt %) | 35.5 | 37.5 | 20.5 | 35.6 | 37.5 | 20.5 |
| 300-212 (wt %) | 27.5 | 17 | 10.9 | 27.4 | 16.9 | 10.8 |
| 212-150 (wt %) | 13.2 | 7.3 | 4.4 | 13.2 | 7.4 | 4.3 |
| 150-45 μm (wt %) | 3.7 | 4.6 | 2.4 | 3.7 | 4.6 | 2.3 |
| Less than or equal to 45 μm (wt %) | 0.1 | 0.1 | 0.1 | 0.1 | 0.1 | 0.2 |
| Total (wt %) | 100.0 | 100.0 | 100.0 | 100.0 | 100.0 | 100.0 |
| D50 (μm) | 315 | 365 | 488 | 315 | 365 | 489 |
| 850-150 μm (wt %) | 96.2 | 95.3 | 97.5 | 96.2 | 95.3 | 97.5 |
| σζ | 0.37 | 0.38 | 0.40 | 0.37 | 0.38 | 0.40 |

"Greater than or equal to A μm" shows water-absorbing resin particles or water absorbent which remained, after classification, on a sieve whose mesh size is A.
"Less than or equal to B μm" shows water-absorbing resin particles or water absorbent which passed through, after classification, a sieve whose mesh size is B.
"A μm-B μm" shows water-absorbing resin particles or water absorbent which passed through, after classification, a sieve whose mesh size is A and are remained, after classification, on a sieve whose mesh size is B.

TABLE 3

| | Comparative Example No. | | | | | | |
|---|---|---|---|---|---|---|---|
| | 1 | 2 | 3 | 4 | 5 | 6 | 7 |
| | Comparative water absorbent | | | | | | |
| | (1) | (2) | (3) | (4) | (5) | (6) | (7) |
| Greater than or equal to 850 μm (wt %) | 0.0 | 0.0 | 0.0 | 0.0 | 0.0 | 0.0 | 0.0 |
| 850-710 μm (wt %) | 2.7 | 0.0 | 1.2 | 2.1 | 2.6 | 0.0 | 1.1 |
| 710-600 μm (wt %) | 27.8 | 6.1 | 15.1 | 21.0 | 27.9 | 6 | 14.9 |
| 600-500 μm (wt %) | 17.3 | 8.6 | 20.1 | 16.0 | 17.4 | 8.6 | 20.2 |
| 500-425 μm (wt %) | 13.6 | 18.3 | 18.8 | 12.0 | 13.7 | 18.2 | 18.9 |
| 425-300 μm (wt %) | 20.3 | 37.4 | 19.5 | 18.0 | 20 | 37.5 | 19.4 |
| 300-212 μm (wt %) | 11 | 17.4 | 14.5 | 12.0 | 11.1 | 17.3 | 14.6 |
| 212-150 μm (wt %) | 4.5 | 7.4 | 5.2 | 7.9 | 4.4 | 7.5 | 5.2 |
| 150-45 μm (wt %) | 2.6 | 4.7 | 5.3 | 10.0 | 2.7 | 4.8 | 5.4 |
| Less than or equal to 45 μm (wt %) | 0.2 | 0.1 | 0.3 | 1.0 | 0.2 | 0.1 | 0.3 |
| Total (wt %) | 100.0 | 100.0 | 100.0 | 100.0 | 100.0 | 100.0 | 100.0 |
| D50 (μm) | 487 | 363 | 444 | 431 | 488 | 363 | 444 |

TABLE 3-continued

|  | Comparative Example No. | | | | | | |
|---|---|---|---|---|---|---|---|
|  | 1 | 2 | 3 | 4 | 5 | 6 | 7 |
|  | Comparative water absorbent | | | | | | |
|  | (1) | (2) | (3) | (4) | (5) | (6) | (7) |
| 850-150 μm (wt %) | 97.2 | 95.2 | 94.4 | 89.0 | 97.1 | 95.1 | 94.3 |
| σζ | 0.41 | 0.38 | 0.45 | 0.60 | 0.41 | 0.38 | 0.45 |

"Greater than or equal to A μm" shows water-absorbing resin particles or water absorbent which remained, after classification, on a sieve whose mesh size is A.
"Less than or equal to B μm" shows water-absorbing resin particles or water absorbent which passed through, after classification, a sieve whose mesh size is B.
"A μm-B μm" shows water-absorbing resin particles or water absorbent which passed through, after classification, a sieve whose mesh size is A and are remained, after classification, on a sieve whose mesh size is B.

It is clear from Table 1 that each water absorbent obtained in the Examples of the present invention had the excellent chemical cross-linked index, and also had excellent APPs and SFC. In contrast, the comparative water absorbents (1) and (5) did not have enough APPs. The comparative water absorbents (2) and (6) did not have enough chemical cross-linked index. Because the comparative water absorbents (3) and (7) had too high CRCs, they did not have enough liquid permeability and diffusibility. Because the particle size distribution of the comparative water absorbent (4) was not adjusted, AAPs and SFC were low. As a result, the comparative water absorbent (4) did not have enough properties. In addition, the comparative water absorbent (4) had much dust and was fine particles which were very difficult to use.

Table 4 shows the evaluation result of the water-absorbing body using the water absorbents (1) to (6) and the comparative water absorbents (1) to (7).

TABLE 4

| Example No. | Water absorbent or Comparative water absorbent | A | B | C | D | Comprehensive evaluation |
|---|---|---|---|---|---|---|
| Example 1 | Water absorbent (1) | 4 | 3 | 4 | 4 | 15 |
| Example 2 | Water absorbent (2) | 5 | 2 | 3 | 4 | 14 |
| Example 3 | Water absorbent (3) | 4 | 3 | 3 | 4 | 14 |
| Example 4 | Water absorbent (4) | 4 | 4 | 3 | 4 | 15 |
| Example 5 | Water absorbent (5) | 5 | 3 | 2 | 4 | 14 |
| Example 6 | Water absorbent (6) | 4 | 5 | 3 | 4 | 16 |
| Comparative Example 1 | Comparative water absorbent (1) | 4 | 1 | 1 | 3 | 9 |
| Comparative Example 2 | Comparative water absorbent (2) | 5 | 2 | 3 | 2 | 12 |
| Comparative Example 3 | Comparative water absorbent (3) | 5 | 1 | 3 | 3 | 12 |
| Comparative Example 4 | Comparative water absorbent (4) | 4 | 2 | 2 | 4 | 12 |
| Comparative Example 5 | Comparative water absorbent (5) | 4 | 1 | 1 | 3 | 9 |
| Comparative Example 6 | Comparative water absorbent (6) | 5 | 2 | 2 | 2 | 11 |
| Comparative Example 7 | Comparative water absorbent (7) | 5 | 1 | 3 | 3 | 12 |

A: absorbing amount,
B: liquid absorbing rate,
C: dryness of absorbed water-absorbing body against pressure,
D: stability of the gel swelled 16 hours before
5-grade Evaluation:
5: very good,
4: good,
3: average,
2: bad,
1: very bad
Comprehensive evaluation = A + B + C + D It is clear from Table 4 that each water-absorbing body using, the water absorbents obtained in the Examples of the present invention had excellent properties as compared with the water-absorbing body using the comparative water absorbents.

EXAMPLE 7

The polymerization and drying were carried out in the same way described in the Example 1 except that a reaction liquid was prepared by dissolving 17.87 g (0.15 mol %) of polyethyleneglycol diacrylate and 2.19 g of disodium hydrogenphosphite pentahydrate in 5426 g of a sodium acrylic acid aqueous solution (39 wt % of monomer concentration) having the neutralization ratio of 71 mol %. The water-absorbing resin obtained was pulverized with the roll mill and was classified with JIS standard sieves whose mesh sizes were 600 μm and 150 μm, so as to adjust the particle size distribution of the water-absorbing resin. In this way, water-absorbing resin (D7) was obtained. CRCs of the water-absorbing resin (D7) obtained was 31.2 g/g. 100 g of the water-absorbing resin (D7) was mixed with an aqueous solution which contained 0.4 g of 1,4-butanediol, 0.6 g of propylene glycol, and 3.0 g of the deionized water. The mixture was subjected to a heat treatment by which the mixture was kept at 200° C. for 30 minutes. After that, the mixture was cooled down to 60° C. After that, the mixture was passed through the JIS standard sieve whose mesh size was 600 µm in order to obtain water-absorbing resin particles (E7). The water-absorbing resin particles (E7) obtained were used as the water absorbent (7).

EXAMPLE 8

The polymerization and drying were carried out in the same way described in the Example 1 except that a reaction liquid was prepared by dissolving 17.87 g (0.15 mol %) of polyethyleneglycol diacrylate and 3.65 g of disodium hydrogenphosphite pentahydrate in 5425 g of a sodium acrylic acid aqueous solution (39 wt % of monomer concentration) having the neutralization ratio of 71 mol %. The water-absorbing resin obtained was pulverized with the roll mill and was classified with JIS standard sieves whose mesh sizes were 850 µm and 150 µm, so as to adjust the particle size distribution of the water-absorbing resin. In this way, water-absorbing resin (D8 was obtained. CRCs of the water-absorbing resin (D8) obtained was 31.9 g/g. 100 g of the water-absorbing resin (D8) was mixed with an aqueous solution which contained 1.0 g of 1,3-propanediol and 3.0 g of the deionized water. The mixture was subjected to a heat treatment by which the mixture was kept at 190° C. for 30 minutes. After that, the mixture was cooled down to 60° C. After that, the mixture was passed through the JIS standard sieve whose mesh size was 850 µm in order to obtain water-absorbing resin particles (E8). The water-absorbing resin particles (E8) obtained were used as the water absorbent (8).

EXAMPLE 9

The polymerization and drying were carried out in the same way described in the Example 1 except that a reaction liquid was prepared by dissolving 23.83 g (0.20 mol %) of polyethyleneglycol diacrylate and 2.19 g of disodium hydrogenphosphite pentahydrate in 5426 g of a sodium acrylic acid aqueous solution (39 wt % of monomer concentration) having the neutralization ratio of 71 mol %. The water-absorbing resin obtained was pulverized with the roll mill and was classified with JIS standard sieves whose mesh sizes were 710 µm and 150 µm, so as to adjust the particle size distribution of the water-absorbing resin. In this way, water-absorbing resin (D9) was obtained. CRCs of the water-absorbing resin (D9) obtained was 27.4 g/g. 100 g of the water-absorbing resin (D9) was mixed with an aqueous solution which contained 1.0 g of ethylene carbonate and 3.0 g of the deionized water. The mixture was subjected to a heat treatment by which the mixture was kept at 195° C. for 30 minutes. After that, the mixture was cooled down to 60° C. After that, the mixture was passed through the JIS standard sieve whose mesh size was 710 µm in order to obtain water-absorbing resin particles (E9). The water-absorbing resin particles (E9) obtained were used as the water absorbent (9).

EXAMPLE 10

100 g of the water-absorbing resin particles (E7) were heated up to 160° C., and were mixed with 1.6 g of potassium alum (aluminum potassium sulfate 12-water, weight average diameter of 150 µm) with stirring. The mixture was stirred for 10 minutes. In this way, water absorbent (10) was obtained.

EXAMPLE 11

100 g of the water-absorbing resin (D8) obtained in the Example 8 was mixed with an aqueous solution which contained 0.6 g of propylene glycol, 1.0 g of aluminum sulfate 14-18 water, and 1.5 g of the deionized water. The mixture was subjected to a heat treatment by which the mixture was kept at 190° C. for 30 minutes. After that, the mixture was cooled down to 60° C. After that, the mixture was passed through the JIS standard sieve whose mesh size was 850 µm in order to obtain water-absorbing resin (11).

EXAMPLE 12

1.0 g of aluminum sulfate 14-18 water (weight average diameter of about 150 µm) were thoroughly mixed with 100 g of the water-absorbing resin particles (E9) obtained in the Example 9. 5 g of the deionized water was evenly added to the mixture. The mixture was dried at a temperature of 60° C. for 30 minutes. After that, the mixture was passed through the JIS standard sieve whose mesh size was 710 µm. The composition obtained was regarded as the water absorbent (12).

COMPARATIVE EXAMPLE 8

The water-absorbing resin (D9) obtained in the Example 9 was regarded as the comparative water absorbent (8).

COMPARATIVE EXAMPLE 9

The polymerization and drying were carried out in the same way described in the Example 1 except that a reaction liquid was prepared by dissolving 11.91 g (0.10 mol %) of polyethyleneglycol diacrylate in 5434 g of a sodium acrylic acid aqueous solution (39 wt % of monomer concentration) having the neutralization ratio of 71 mol %. The water-absorbing resin obtained was pulverized with the roll mill and was classified with JIS standard sieves whose mesh sizes were 600 µm and 150 µm, so as to adjust the particle size distribution of the water-absorbing resin. In this way, comparative water-absorbing resin (9) was obtained. 100 g of the comparative water-absorbing resin (9) was mixed with an aqueous solution which contained 0.4 g of 1,4-butanediol, 0.6 g of propylene glycol, and 3.0 g of the deionized water. The mixture was subjected to a heat treatment by which the mixture was kept at 200° C. for 30 minutes. After that, the mixture was cooled down to 60° C. After that, the mixture was passed through the JIS standard sieve whose mesh size was 600 µm in order to obtain comparative water-absorbing resin particles (9). The comparative water-absorbing resin particles (9) obtained were used as the comparative water absorbent (9).

COMPARATIVE EXAMPLE 10

The polymerization and drying were carried out in the same way described in the Example 1 except that a reaction liquid was prepared by dissolving 7.74 g (0.065 mol %) of polyethyleneglycol diacrylate in 5434 g of a sodium acrylic acid aqueous solution (39 wt % of monomer concentration) having the neutralization ratio of 71 mol %. The water-absorbing resin obtained was pulverized with the roll mill and was classified with JIS standard sieves whose mesh sizes were 850 µm and 150 µm, so as to adjust the particle size distribution of the water-absorbing resin. In this way, comparative water-absorbing resin (10) was obtained. CRCs of the comparative water-absorbing resin (10) obtained was 35.2 g/g. 100 g of the comparative water-absorbing resin (10) was mixed with an aqueous solution which contained 1.0 g of 1,3-propanediol and 3.0 g of the deionized water. The mixture was subjected to a heat treatment by which the mixture was kept at 190° C. for 30 minutes. After that, the mixture was cooled down to 60° C. After that, the mixture was passed through the JIS standard sieve whose mesh size was 850 μm in order to obtain comparative water-absorbing resin particles (10). The comparative water-absorbing resin particles (10) obtained were used as the comparative water absorbent (10).

COMPARATIVE EXAMPLE 11

100 g of the comparative water-absorbing resin particles (8) was heated up to 160° C., and was mixed with 1.6 g of potassium alum (aluminum potassium sulfate 12-water, weight average diameter of 150 μm) with stirring. The mixture was stirred for 10 minutes. In this way, the comparative water absorbent (11) was obtained.

COMPARATIVE EXAMPLE 12

100 g of the comparative water-absorbing resin (9) obtained in the Comparative Example 9 was mixed with an aqueous solution which contained 0.6 g of propylene glycol, 1.0 g of aluminum sulfate 14-18 water, and 1.5 g of the deionized water. The mixture was subjected to a heat treatment by which the mixture was kept at 190° C. for 30 minutes. After that, the mixture was cooled down to 60° C. After that, the mixture was passed through the JIS standard sieve whose mesh size was 600 μm in order to obtain the comparative water absorbent (12).

COMPARATIVE EXAMPLE 13

1.0 g of aluminum sulfate 14-18 water (weight average diameter of about 150 μm) was thoroughly mixed with 100 g of the comparative water-absorbing resin particles (10) obtained in the Comparative Example 10. 5 g of the deionized water was evenly added to the mixture. The mixture was dried at a temperature of 60° C. for 30 minutes. After that, the mixture was passed through the JIS standard sieve whose mesh size was 850 μm. The composition obtained was regarded as the comparative water absorbent (13).

Table 5 shows properties (ratio of particles whose diameter was greater than or equal to 150 μm and less than 850 μm, σζ, CRCs, AAPs, SFC, CRCdw, and chemical cross-linked index against pressure) of the water absorbents (7) to (12) obtained in the Examples 7 to 12 and properties of the comparative water absorbents (8) to (13) obtained in the Comparative Examples 8 to 13. Tables 6 and 7 show particle size distributions.

TABLE 5

| Example No. | Water absorbent or Comparative water absorbent | Ratio of particles whose diameter was Greater than or equal to 150 μm and less than 850 μm | σζ | CRCs (g/g) | AAPs (g/g) | SFC ($10^{-7} \cdot cm^3 \cdot s \cdot g^{-1}$) | AAPdw (g/g) | Chemical cross-linked index against pressure |
|---|---|---|---|---|---|---|---|---|
| Example 7 | Water absorbent (7) | 96.4 | 0.36 | 26.1 | 24.4 | 88 | 90.0 | 116.1 |
| Example 8 | Water absorbent (8) | 97.7 | 0.40 | 28.5 | 25.3 | 91 | 97.0 | 125.5 |
| Example 9 | Water absorbent (9) | 95.8 | 0.36 | 24.6 | 24.0 | 171 | 100.0 | 124.6 |
| Example 10 | Water absorbent (10) | 96.3 | 0.36 | 26.3 | 24.2 | 240 | 90.0 | 116.3 |
| Example 11 | Water absorbent (11) | 97.8 | 0.40 | 28.6 | 23.1 | 178 | 94.0 | 122.6 |
| Example 12 | Water absorbent (12) | 95.2 | 0.37 | 24.6 | 22.9 | 256 | 98.0 | 122.6 |
| Comparative Example 8 | Comparative water absorbent (8) | 95.7 | 0.36 | 27.4 | 16.3 | 5 | 29.7 | 57.1 |
| Comparative Example 9 | Comparative water absorbent (9) | 96.7 | 0.36 | 25.8 | 23.8 | 76 | 54.9 | 80.7 |
| Comparative Example 10 | Comparative water absorbent (10) | 97.3 | 0.41 | 28.4 | 25.1 | 50 | 58.1 | 86.5 |
| Comparative Example 11 | Comparative water absorbent (11) | 95.8 | 0.36 | 27.5 | 19.4 | 14 | 41.9 | 69.4 |
| Comparative Example 12 | Comparative water absorbent (12) | 96.5 | 0.36 | 24.9 | 21.9 | 123 | 53.0 | 77.9 |
| Comparative Example 13 | Comparative water absorbent (13) | 97.6 | 0.40 | 28.4 | 23.1 | 95 | 55.0 | 83.4 |

TABLE 6

| | Example No. | | | | | |
|---|---|---|---|---|---|---|
| | 7 | 8 | 9 | 10 | 11 | 12 |
| | \multicolumn{6}{c}{Water absorbent} |
| | (7) | (8) | (9) | (10) | (11) | (12) |
| Greater than or equal to 850 μm (wt %) | 0.0 | 0.0 | 0.0 | 0.0 | 0.0 | 0.0 |
| 850-710 μm (wt %) | 0.0 | 2.1 | 0.0 | 0.0 | 2.2 | 0.0 |
| 710-600 μm (wt %) | 0.0 | 26.7 | 6.1 | 0.0 | 26.8 | 6.2 |
| 600-500 μm (wt %) | 2.7 | 16.5 | 8.1 | 2.5 | 16.6 | 8.0 |
| 500-425 μm (wt %) | 16.7 | 14.6 | 19.1 | 16.7 | 14.6 | 18.9 |

TABLE 6-continued

| | Example No. | | | | | |
|---|---|---|---|---|---|---|
| | 7 | 8 | 9 | 10 | 11 | 12 |
| | Water absorbent | | | | | |
| | (7) | (8) | (9) | (10) | (11) | (12) |
| 425-300 μm (wt %) | 36.0 | 22.1 | 38.2 | 36.1 | 22 | 37.5 |
| 300-212 μm (wt %) | 28.3 | 11.4 | 17.5 | 28.2 | 11.1 | 17.3 |
| 212-150 μm (wt %) | 12.7 | 4.3 | 6.8 | 12.8 | 4.5 | 7.3 |
| 150-45 μm (wt %) | 3.5 | 2.2 | 4.1 | 3.6 | 2.1 | 4.0 |
| Less than or equal to 45 μm (wt %) | 0.1 | 0.1 | 0.1 | 0.1 | 0.1 | 0.1 |
| Total (wt %) | 100.0 | 100.0 | 100.0 | 100.0 | 100.0 | 99.3 |
| D50 (μm) | 315 | 475 | 366 | 314 | 476 | 364 |
| 850-150 μm (wt %) | 96.4 | 97.7 | 95.8 | 96.3 | 97.8 | 95.2 |
| σζ | 0.36 | 0.40 | 0.36 | 0.36 | 0.40 | 0.37 |

"Greater than or equal to A μm" shows water-absorbing resin particles or water absorbent which remained, after classification, on a sieve whose mesh size is A.
"Less than or equal to B μm" shows water-absorbing resin particles or water absorbent which passed through, after classification, a sieve whose mesh size is B.
"A μm-B μm" shows water-absorbing resin particles or water absorbent which passed through, after classification, a sieve whose mesh size is A and are remained, after classification, on a sieve whose mesh size is B.

TABLE 7

| | Comparative Example No. | | | | | |
|---|---|---|---|---|---|---|
| | 8 | 9 | 10 | 11 | 12 | 13 |
| | Comparative water absorbent | | | | | |
| | (8) | (9) | (10) | (11) | (12) | (13) |
| Greater than or equal to 850 μm (wt %) | 0.0 | 0.0 | 0.0 | 0.0 | 0.0 | 0.0 |
| 850-710 μm (wt %) | 0.0 | 0.0 | 3.1 | 0.0 | 0.0 | 3.2 |
| 710-600 μm (wt %) | 6.4 | 0.0 | 28.0 | 6.3 | 0.0 | 28.1 |
| 600-500 μm (wt %) | 8.2 | 2.9 | 17.0 | 8.2 | 2.8 | 17.1 |
| 500-425 μm (wt %) | 19.0 | 16.7 | 13.6 | 18.9 | 16.6 | 13.7 |
| 425-300 μm (wt %) | 38.3 | 36.2 | 20.2 | 38.2 | 36.3 | 20.4 |
| 300-212 μm (wt %) | 17.1 | 28.1 | 10.9 | 17.3 | 28.1 | 11.0 |
| 212-150 μm (wt %) | 6.7 | 12.8 | 4.5 | 6.9 | 12.7 | 4.1 |
| 150-45 μm (wt %) | 4.2 | 3.2 | 2.6 | 4.1 | 3.4 | 2.3 |
| Less than or equal to 45 μm (wt %) | 0.1 | 0.1 | 0.1 | 0.1 | 0.1 | 0.1 |
| Total (wt %) | 100.0 | 100.0 | 100.0 | 100.0 | 100.0 | 100.0 |
| D50 (μm) | 367 | 316 | 489 | 366 | 315 | 491 |
| 850-150 μm (wt %) | 95.7 | 96.7 | 97.3 | 95.8 | 96.5 | 97.6 |
| σζ | 0.36 | 0.36 | 0.41 | 0.36 | 0.36 | 0.40 |

"Greater than or equal to A μm" shows water-absorbing resin particles or water absorbent which remained, after classification, on a sieve whose mesh size is A.
"Less than or equal to B μm" shows water-absorbing resin particles or water absorbent which passed through, after classification, a sieve whose mesh size is B.
"A μm-B μm" shows water-absorbing resin particles or water absorbent which passed through, after classification, a sieve whose mesh size is A and are remained, after classification, on a sieve whose mesh size is B.

It is clear from Table 5 that each water absorbent of the present invention has excellent chemical cross-linked index against pressure, and also has excellent APPs and SFC. In contrast, the comparative water absorbents (8) and (11) do not have enough APPs. The comparative water absorbents (8) to (13) do not have enough chemical cross-linked-index against pressure. Table 8 shows the evaluation result of water-absorbing bodies using the water absorbents (7) to (12) and the comparative water absorbents (8) to (13).

TABLE 8

| Example No. | Water absorbent or Comparative water absorbent | A | B | C | D | Comprehensive evaluation |
|---|---|---|---|---|---|---|
| Example 7 | Water absorbent (7) | 3 | 3 | 5 | 5 | 16 |
| Example 8 | Water absorbent (8) | 3 | 3 | 5 | 5 | 16 |
| Example 9 | Water absorbent (9) | 2 | 5 | 5 | 5 | 17 |
| Example 10 | Water absorbent (10) | 3 | 5 | 5 | 5 | 18 |
| Example 11 | Water absorbent (11) | 3 | 5 | 5 | 5 | 18 |
| Example 12 | Water absorbent (12) | 2 | 5 | 5 | 5 | 17 |

TABLE 8-continued

| Example No. | Water absorbent or Comparative water absorbent | A | B | C | D | Comprehensive evaluation |
|---|---|---|---|---|---|---|
| Comparative Example 8 | Comparative water absorbent (8) | 3 | 2 | 1 | 4 | 10 |
| Comparative Example 9 | Comparative water absorbent (9) | 3 | 3 | 2 | 4 | 12 |
| Comparative Example 10 | Comparative water absorbent (10) | 3 | 3 | 3 | 3 | 12 |
| Comparative Example 11 | Comparative water absorbent (11) | 3 | 2 | 1 | 4 | 10 |
| Comparative Example 12 | Comparative water absorbent (12) | 2 | 4 | 2 | 4 | 12 |
| Comparative Example 13 | Comparative water absorbent (13) | 3 | 3 | 3 | 3 | 12 |

A: absorbing amount,
B: liquid absorbing rate,
C: dryness of absorbed water-absorbing body against pressure,
D: stability of the gel swelled 16 hours before
5-grade Evaluation
5: very good,
4: good,
3: average,
2: bad,
1: very bad
Comprehensive evaluation = A + B + C + D It is clear from Table 8 that the water-absorbing bodies using the water absorbents obtained in the Examples of the present invention have excellent properties as compared with the water-absorbing bodies using the comparative water absorbents.

Table 9 shows CRCs and SPGL(B) of the water-absorbing resins (D1) to (D3) and (D7) to (D9) obtained in the Examples 1 to 3 and 7 to 9, and also shows CRCs and SPGL(B) of the comparative water-absorbing resins (2) to (4), (9), and (10) obtained in the Comparative Examples 2 to 4, 9, and 10. Tables 10 and 11 show ratio of particles whose diameter was greater than or equal to 106 μm and less than 850 μm, σζ, and particle size distributions.

TABLE 9

| Example No. | Water-absorbing resin | CRCs (g/g) | SPGL(B) (kdyne/cm$^2$) |
|---|---|---|---|
| Example 1 | Water-absorbing resin (D1) | 35.2 | 43.3 |
| Example 2 | Water-absorbing resin (D2) | 39.4 | 35.1 |
| Example 3 | Water-absorbing resin (D3) | 32.8 | 41.9 |
| Example 7 | Water-absorbing resin (D7) | 31.2 | 49.3 |
| Example 8 | Water-absorbing resin (D8) | 31.9 | 48.4 |
| Example 9 | Water-absorbing resin (D9) | 27.4 | 49.2 |
| Comparative Example 2 | Comparative water-absorbing resin (2) | 44.0 | 27.8 |
| Comparative Example 3 | Comparative water-absorbing resin (3) | 51.0 | 33.2 |
| Comparative Example 4 | Comparative water-absorbing resin (4) | 32.7 | 41.9 |
| Comparative Example 9 | Comparative water-absorbing resin (9) | 31.5 | 33.6 |
| Comparative Example 10 | Comparative water-absorbing resin (10) | 35.2 | 29.8 |

TABLE 10

| | Example No. | | | | | |
|---|---|---|---|---|---|---|
| | 1 | 2 | 3 | 7 | 8 | 9 |
| | Water-absorbing resin | | | | | |
| | (D1) | (D2) | (D3) | (D7) | (D8) | (D9) |
| Greater than or equal to 850 μm (wt %) | 0.0 | 0.0 | 0.0 | 0.0 | 0.0 | 0.0 |
| 850-710 μm (wt %) | 0.0 | 0.0 | 2.7 | 0.0 | 2.7 | 0.0 |
| 710-600 μm (wt %) | 0.0 | 6.5 | 27.8 | 0.0 | 27.7 | 6.4 |
| 600-500 μm (wt %) | 2.9 | 8.5 | 17.3 | 2.6 | 17.1 | 8.2 |
| 500-425 μm (wt %) | 16.7 | 18.1 | 13.6 | 16.7 | 13.4 | 19.0 |
| 425-300 μm (wt %) | 35.3 | 37.5 | 20.3 | 35.9 | 20.8 | 38.3 |
| 300-212 μm (wt %) | 27.9 | 17.2 | 11.0 | 28.6 | 11.2 | 17.1 |
| 212-150 μm (wt %) | 13.4 | 7.5 | 4.5 | 12.6 | 4.6 | 6.7 |
| 150-106 μm (wt %) | 2.5 | 3.1 | 1.6 | 2.3 | 1.5 | 2.8 |
| 106-45 μm (wt %) | 1.2 | 1.5 | 1.0 | 1.2 | 0.9 | 1.4 |
| Less than or equal to 45 μm (wt %) | 0.1 | 0.1 | 0.2 | 0.1 | 0.1 | 0.1 |
| Total (wt %) | 100.0 | 100.0 | 100.0 | 100.0 | 100.0 | 100.0 |
| D50 (μm) | 313 | 364 | 487 | 314 | 473 | 367 |

TABLE 10-continued

| | Example No. | | | | | |
|---|---|---|---|---|---|---|
| | 1 | 2 | 3 | 7 | 8 | 9 |
| | Water-absorbing resin | | | | | |
| | (D1) | (D2) | (D3) | (D7) | (D8) | (D9) |
| 850-106 μm (wt %) | 98.7 | 98.4 | 98.8 | 98.7 | 99.0 | 98.5 |
| σζ | 0.37 | 0.38 | 0.41 | 0.36 | 0.40 | 0.36 |

"Greater than or equal to A μm" shows water-absorbing resin particles or water absorbent which remained, after classification, on a sieve whose mesh size is A.
"Less than or equal to B μm" shows water-absorbing resin particles or water absorbent which passed through, after classification, a sieve whose mesh size is B.
"A μm-B μm" shows water-absorbing resin particles or water absorbent which passed through, after classification, a sieve whose mesh size is A and are remained, after classification, on a sieve whose mesh size is B.

TABLE 11

| | Example No. | | | | |
|---|---|---|---|---|---|
| | 2 | 3 | 4 | 9 | 10 |
| | Comparative water-absorbing resin | | | | |
| | (2) | (3) | (4) | (9) | (10) |
| Greater than or equal to 850 μm (wt %) | 0.0 | 0.0 | 0.0 | 0.0 | 0.0 |
| 850-710 μm (wt %) | 0.0 | 1.1 | 2.0 | 0.0 | 3.0 |
| 710-600 μm (wt %) | 6.0 | 15.0 | 20.9 | 0.0 | 28 |
| 600-500 μm (wt %) | 8.4 | 20.0 | 15.9 | 2.7 | 16.8 |
| 500-425 μm (wt %) | 18.1 | 18.6 | 12 | 16.6 | 13.6 |
| 425-300 μm (wt %) | 37.6 | 19.7 | 18.1 | 36.1 | 20.3 |
| 300-212 μm (wt %) | 17.6 | 14.7 | 12.2 | 28.3 | 11.1 |
| 212-150 μm (wt %) | 7.5 | 5.3 | 7.9 | 13.0 | 4.6 |
| 150-106 μm (wt %) | 3.2 | 3.0 | 5.4 | 2.0 | 1.7 |
| 106-45 μm (wt %) | 1.5 | 2.3 | 4.6 | 1.2 | 0.8 |
| Less than or equal to 45 μm (wt %) | 0.1 | 0.3 | 1.0 | 0.1 | 0.1 |
| Total (wt %) | 100.0 | 100.0 | 100.0 | 100.0 | 100.0 |
| D50 (μm) | 362 | 443 | 430 | 314 | 487 |
| 850-106 μm (wt %) | 98.4 | 97.4 | 94.4 | 98.7 | 99.1 |
| σζ | 0.38 | 0.43 | 0.60 | 0.36 | 0.41 |

"Greater than or equal to A μm" shows water-absorbing resin particles or water absorbent which remained, after classification, on a sieve whose mesh size is A.
"Less than or equal to B μm" shows water-absorbing resin particles or water absorbent which passed through, after classification, a sieve whose mesh size is B.
"A μm-B μm" shows water-absorbing resin particles or water absorbent which passed through, after classification, a sieve whose mesh size is A and are remained, after classification, on a sieve whose mesh size is B.

EXAMPLE 13

While a solution (A) was stirred in a polypropylene container by a magnetic stirrer, a solution (B) was poured at a stretch in an open system in order to mix the solutions (A) and (B). The solution (A) was a mixture of 173.0 g of acrylic acids, 2.5 g of polyethyleneglycol diacrylate (molecular weight 523), and 0.01 g of diethylenetriamine pentaacetic acid 5 sodium salt. The solution (B) was a mixture of 138.6 g of a 48.5 wt % NaOH aqueous solution and 276.2 g of ion-exchange water whose temperature was adjusted to 50° C. The polypropylene container, covered with polystylene foam (heat insulating material), had an internal diameter of 80 mm, and a capacity of 1 liter. As a result, a monomer aqueous solution (35 wt % of monomer concentration, 70 mol % of the neutralization ratio), whose temperature went up to about 100° C. because of heat of neutralization and dissolution, was obtained. Further, 9.6 g of a 3 wt % sodium persulfate aqueous solution was added to the monomer aqueous solution and stirred for several seconds. Right after that, the aqueous solution thus stirred was poured in the open system into a stainless vat-type container, whose surface was heated up to 100° C. by a hotplate (NEO HOTPLATE H1-1000, produced by Iuchi Seieido), in which Teflon (registered mark) film was applied to an inner surface, whose bottom surface was 250 mm×250 mm. The bottom surface of the stainless vat-type container was 250 mm×250 mm, an upper surface of that was 640 mm×640 mm, the height of that was 50 mm, a central cross-section was a trapezoid, and the upper surface was open.

Polymerization started soon after the monomer aqueous solution was poured into the vat. The polymerization proceeded, as water vapor was generated and a gel expanded in all directions with foaming. Finally, the gel shrank and its size became a bit larger than the bottom surface. The expansion and shrinkage ended within about 1 minute. After kept in a polymerization container for 4 minutes, hydrate polymer was taken out.

The hydrate polymer obtained was comminuted with a meat chopper (ROYAL MEAT CHOPPER VR400K, produced by IIZUKA) whose dice diameter was 9.5 mm. In this way, the hydrate polymer thus comminuted was obtained.

The hydrate polymer thus comminuted was spread on a 50-mesh metal net, and was dried by hot air of 180° C. for 40 minutes. The hydrate polymer thus dried was pulverized with a roll mill, and was classified with the JIS standard sieve whose mesh size was 600 μm. As a result, irregularly-shaped and pulverized water-absorbing resin, whose weight average diameter was 323 μm and whose logarithmic standard deviation (σζ) was 0.36, was obtained. CRCs of the water-absorbing resin thus obtained was 34.0 g/g, and SPGL was 37.6 kdyne/cm². The other properties were shown in Tables 12 and 13.

After 100 parts by weight of water-absorbing resin obtained was mixed with a surface cross-linking agent made of a mixed liquid of 0.3 parts by weight of 1,4-butanediol, 0.6 parts by weight of propylene glycol, and 3 parts by weight of deionized water, a mixture was subjected to a heat treatment by which the mixture was kept at 195° C. for 30 minutes. Then, particles thus treated were disintegrated so that they passed through the JIS standard sieve whose mesh size was 600 μm. As a result, the water-absorbing resin whose surface was cross-linked was obtained. Table 12 shows properties of the water absorbent (13) obtained.

EXAMPLE 14

The operation was carried out in the same way described in the Example 13 except that 0.25 mol % polyethyleneglycol diacrylate was used. As a result, irregularly-shaped and pulverized water-absorbing resin, whose weight average diameter was 328 μm and whose logarithmic standard deviation (σζ) was 0.36, was obtained. CRCs of the water-absorbing resin obtained was 30.2 g/g, and SPGL was 41.4 kdyne/cm². The other properties were shown in Tables 12 and 13.

EXAMPLE 14-1

Surface cross-linking was carried out under the same condition described in the Example 13, and the water-absorbing resin whose surface was cross-linked was obtained. Table 12 shows properties of the water absorbent (14-1) obtained.

EXAMPLE 14-2

After 100 parts by weight of water-absorbing resin obtained was mixed with a surface cross-linking agent made of a mixed liquid of 0.3 parts by weight of 1,4-butanediol, 0.6 parts by weight of propylene glycol, and 3 parts by weight of deionized water, a mixture was subjected to a heat treatment by which the mixture was kept at 195° C. for 35 minutes. Then, particles thus treated were disintegrated so that they passed through the JIS standard sieve whose mesh size was 600 μm. As a result, the water-absorbing resin whose surface was cross-linked was obtained. Table 12 shows properties of the water absorbent (14-2) obtained.

EXAMPLE 15

While a solution (A) was stirred in a polypropylene container by a magnetic stirrer, a solution (B) was poured at a stretch in an open system in order to mix the solutions (A) and (B). The solution (A) was a mixture of 192.2 g of acrylic acids, 2.79 g of polyethyleneglycol diacrylate (molecular weight 523), and 0.01 g of diethylenetriamine pentaacetic acid 5 sodium salt. The solution (B) was a mixture of 156.8 g of a 48.5 wt % NaOH aqueous solution and 239.3 g of ion-exchange water whose temperature was adjusted to 40° C. The polypropylene container, covered with polystylene foam (heat insulating material), had an internal diameter of 80 mm, and a capacity of 1 liter. As a result, a monomer aqueous solution (39 wt % of monomer concentration, 71.3 mol % of the neutralization ratio), whose temperature went up to about 100° C. because of heat of the neutralization and dissolution, was obtained. Further, 8.89 g of a 3 wt % sodium persulfate aqueous solution was added to the monomer aqueous solution and stirred for several seconds. Right after that, the aqueous solution thus stirred was poured in the open system into a stainless vat-type container, whose surface was heated up to 100° C. by a hotplate (NEO HOTPLATE H1-1000, produced by Iuchi Seieido), in which Teflon (registered mark) film was applied to an inner surface, whose bottom surface was 250 mm×250 mm.

Polymerization started soon after the monomer aqueous solution was poured into the vat. The polymerization proceeded, as water vapor was generated and a gel expanded in all directions with foaming. Finally, the gel shrank and its size became a bit larger than the bottom surface. The expansion and shrinkage ended within about 1 minute. After kept in a polymerization container for 3 minutes, hydrate polymer was taken out.

The hydrate polymer, which was in a small-piece form, was spread on a 50-mesh metal net, and was dried by hot air of 180° C. for 40 minutes. The hydrate polymer thus dried was pulverized with a roll mill, and was classified with the JIS standard sieve whose mesh size was 600 μm. As a result, irregularly-shaped and pulverized water-absorbing resin, whose weight average diameter was 325 μm and whose logarithmic standard deviation (σζ) was 0.35, was obtained. CRCs of the water-absorbing resin obtained was 31.4 g/g, and SPGL was 40.1 kdyne/cm². The other properties were shown in Tables 12 and 13.

After the 100 parts by weight of water-absorbing resin obtained was mixed with a surface cross-linking agent made of a mixed liquid of 0.4 parts by weight ethylene carbonate, 1 part by weight propylene glycol, and 3 parts by weight of deionized water, a mixture was subjected to a heat treatment by which the mixture was kept at 190° C. for 35 minutes. Then, particles thus treated were disintegrated so that they passed through the JIS standard sieve whose mesh size was 600 μm. As a result, the water-absorbing resin whose surface was cross-linked was obtained. Table 12 shows properties of the water absorbent (15) obtained.

EXAMPLE 16

While a solution (A) was stirred in a polypropylene container by a magnetic stirrer, a solution (B) was poured at a stretch in an open system in order to mix the solutions (A) and (B). The solution (A) was a mixture of 259.6 g of acrylic acids, 2.26 g of polyethyleneglycol diacrylate (molecular weight 523), and 0.01 g of diethylenetriamine pentaacetic acid 5 sodium salt. The solution (B) was a mixture of 208.0 g of a 48.5 wt % NaOH aqueous solution and 223.0 g of ion-exchange water whose temperature was adjusted to 25° C. The polypropylene container, covered with polystylene foam (heat insulating material), had an internal diameter of 80 mm, and a capacity of 1 liter. As a result, a monomer aqueous solution (45 wt % of monomer concentration, 70 mol % of the neutralization ratio), whose temperature went up to about 100° C. because of heat of the neutralization and dissolution, was obtained. Further, 7.2 g of a 5 wt % sodium persulfate aqueous solution was added to the monomer aqueous solution and stirred for several seconds. Right after that, the aqueous solution thus stirred was poured in the open system into a stainless vat-type container, whose surface was heated up to 100° C. by a hotplate (NEO HOTPLATE H1-1000, produced by Iuchi Seieido), in which Teflon (registered mark) film was applied to an inner surface, whose bottom surface was 250 mm×250 mm. The bottom surface of the stainless vat-type container was 250 mm×250 mm, an upper surface of that was 640 mm×640 mm, the height of that was 50 mm, a central cross-section was a trapezoid, and the upper surface was open.

Polymerization started soon after the monomer aqueous solution was poured into the vat. The polymerization proceeded, as water vapor was generated and a gel expanded in all directions with foaming. Finally, the gel shrank and its size became a bit larger than the bottom surface. The expansion and shrinkage ended within about 1 minute. After kept in a polymerization container for 3 minutes, hydrate polymer was taken out.

The hydrate polymer, which was in a small-piece form, was spread on a 50-mesh metal net, and was dried by hot air of 190° C. for 40 minutes. The hydrate polymer thus dried was pulverized with a roll mill, and was classified with the JIS standard sieve whose mesh size was 600 μm. As a result, irregularly-shaped and pulverized water-absorbing resin, whose weight average diameter was 312 μm and whose logarithmic standard deviation (σζ) was 0.40, was obtained. CRCs of the water-absorbing resin obtained was 32.4 g/g, and SPGL was 35.2 kdyne/cm². The other properties were shown in Tables 12 and 13.

After 100 parts by weight of water-absorbing resin obtained was mixed with a surface cross-linking agent made of a mixed liquid of 0.6 parts by weight of 1,4-butanediol, 0.8 parts by weight propylene glycol, and 3.8 parts by weight of deionized water, a mixture was subjected to a heat treatment by which the mixture was kept at 190° C. for 50 minutes.

Then, particles thus treated were disintegrated so that they passed through the JIS standard sieve whose mesh size was 600 µm. As a result, the water-absorbing resin whose surface was cross-linked was obtained. Table 12 shows properties of the water absorbent (16) obtained.

EXAMPLE 17

While a solution (A) was stirred in a polypropylene container by a magnetic stirrer, a solution (B) was poured at a stretch in an open system in order to mix the solutions (A) and (B). The solution (A) was a mixture of 214.7 g of acrylic acids, 3.12 g of polyethyleneglycol diacrylate (molecular weight 523), 0.03 g of 2-hydroxy-2-methyl-1-phenyl-propane-1-one, 0.01 g of diethylenetriamine pentaacetic acid 5 sodium salt, and 2.63 g of polypropylene glycol (molecular weight 6000). The solution (B) was a mixture of 179.4 g of a 48.5 wt % NaOH aqueous solution and 338.3 g of ion-exchange water whose temperature was adjusted to 40° C. The polypropylene container, covered with polystylene foam (heat insulating material), had an internal diameter of 80 mm, and a capacity of 1 liter. As a result, a monomer aqueous solution (35 wt % of monomer concentration, 73.0 mol % of the neutralization ratio), whose temperature went up to about 100° C. because of heat of the neutralization and dissolution, was obtained. Further, 11.9 g of a 3 wt % sodium persulfate aqueous solution was added to the monomer aqueous solution and stirred for several seconds. Right after that, the aqueous solution thus stirred was poured in the open system into a stainless vat-type container, whose surface was heated up to 100° C. by a hotplate (NEO HOTPLATE H1-1000, produced by Iuchi Seieido), in which Teflon (registered mark) film was applied to an inner surface, whose bottom surface was 250 mm×250 mm.

Ultraviolet rays were irradiated by a black light mercury lamp H400BL (352 nm of peak wavelength) installed in a floodlight MT-420 (both the lamp and the floodlight are produced by TOSHIBA LIGHTING & TECHNOLOGY CORPORATION) simultaneously with pouring of the monomer aqueous solution into the vat. In this way, polymerization started. The polymerization proceeded, as water vapor was generated and a gel expanded in all directions with foaming. Finally, the gel shrank and its size became a bit larger than the bottom surface. The expansion and shrinkage ended within about 1 minute. After kept in a polymerization container for 3 minutes, hydrate polymer was taken out.

The hydrate polymer, which was in a small-piece form, was spread on a 50-mesh metal net, and was dried by hot air of 180° C. for 40 minutes. The hydrate polymer thus dried was pulverized with a roll mill, and was classified with the JIS standard sieve whose mesh size was 600 µm. As a result, irregularly-shaped and pulverized water-absorbing resin, whose weight average diameter was 327 µm and whose logarithmic standard deviation (σζ) was 0.34, was obtained. CRCs of the water-absorbing resin obtained was 34 g/g, and SPGL was 35.7 kdyne/cm² The other properties were shown in Tables 12 and 13.

After 100 parts by weight of water-absorbing resin obtained was mixed with a surface cross-linking agent made of a mixed liquid of 0.3 parts by weight of 1,4-butanediol, 0.6 parts by weight of propylene glycol, and 3 parts by weight of deionized water, a mixture was subjected to a heat treatment by which the mixture was kept at 200° C. for 30 minutes. Then, particles thus treated were disintegrated so that they passed through the JIS standard sieve whose mesh size was 600 µm. As a result, the water-absorbing resin whose surface was cross-linked was obtained. Table 12 shows properties of the water absorbent (17) obtained.

EXAMPLE 18

While a solution (A) was stirred in a polypropylene container by a magnetic stirrer, a solution (B) was poured at a stretch in an open system in order to mix the solutions (A) and (B). The solution (A) was a mixture of 172.5 g of acrylic acids, 3.5 g of polyethyleneglycol diacrylate (molecular weight 523), 0.01 g of diethylenetriamine pentaacetic acid 5 sodium salt, and 0.31 g of disodium hydrogenphosphite pentahydrate. The solution (B) was a mixture of 140.8 g of a 48.5 wt % NaOH aqueous solution and 273.4 g of ion-exchange water which was heated up to 50° C. The polypropylene container, covered with polystylene foam (heat insulating material), had an internal diameter of 80 mm, and a capacity of 1 liter. As a result, a monomer aqueous solution (35 wt % of monomer concentration, 71.3 mol % of the neutralization ratio), whose temperature went up to about 100° C. because of heat of the neutralization and dissolution, was obtained. Further, 9.6 g of a 3 wt % sodium persulfate aqueous solution was added to the monomer aqueous solution and stirred for several seconds. Right after that, the aqueous solution thus stirred was poured in the open system into a stainless vat-type container, whose surface was heated up to 100° C. by a hotplate (NEO HOTPLATE H1-1000, produced by Iuchi Seieido), in which Teflon (registered mark) film was applied to an inner surface, whose bottom surface was 250 mm×250 mm.

Polymerization started soon after the monomer aqueous solution was poured into the vat. The polymerization proceeded, as water vapor was generated and a gel expanded in all directions with foaming. Finally, the gel shrank and its size became a bit larger than the bottom surface. The expansion and shrinkage ended within about 1 minute. After kept in a polymerization container for 3 minutes, hydrate polymer was taken out.

The hydrate polymer, which was in a small-piece form, was spread on a 50-mesh metal net, and was dried by hot air of 180° C. for 40 minutes. The hydrate polymer thus dried was pulverized with a roll mill, and was classified with the JIS standard sieve whose mesh size was 600 µm. As a result, irregularly-shaped and pulverized water-absorbing resin, whose weight average diameter was 321 µm and whose logarithmic standard deviation (σζ) was 0.36, was obtained. CRCs of the water-absorbing resin obtained was 32.6 g/g, and SPGL was 44.2 kdyne/cm². The other properties were shown in Tables 12 and 13.

EXAMPLE 18-1

After 100 parts by weight of water-absorbing resin obtained in the Example 18 was mixed with a surface cross-linking agent made of a mixed liquid of 0.3 parts by weight of 1,4-butanediol, 0.6 parts by weight of propylene glycol, and 3 parts by weight of deionized water, a mixture was subjected to a heat treatment by which the mixture was kept at 190° C. for 30 minutes. Then, particles thus treated were disintegrated so that they passed through the JIS standard sieve, whose mesh size was 600 µm. As a result, the water-absorbing resin whose surface was cross-linked was obtained. Table 12 shows properties of the water absorbent (18-1) obtained.

EXAMPLE 18-2

After 100 parts by weight of water-absorbing resin obtained in the Example 18 was mixed with a surface cross-linking agent made of a mixed liquid of 0.3 parts by weight of 1,4-butanediol, 0.6 parts by weight of propylene glycol, and 3 parts by weight of deionized water, a mixture was subjected to a heat treatment by which the mixture was kept at 190° C. for 35 minutes. Then, particles thus treated were disintegrated so that they passed through the JIS standard sieve whose mesh size was 600 µm. As a result, the water-absorbing resin whose surface was cross-linked was obtained. Table 12 shows properties of the water absorbent (18-2) obtained.

EXAMPLE 19

While a solution (A) was stirred in a polypropylene container by a magnetic stirrer, a solution (B) was poured at a stretch in an open system in order to mix the solutions (A) and (B). The solution (A) was a mixture of 192.2 g of acrylic acids, 3.49 g of polyethyleneglycol diacrylate (molecular weight 523), 0.01 g of diethylenetriamine pentaacetic acid 5 sodium salt, and 0.35 g of disodium hydrogenphosphite pentahydrate. The solution (B) was a mixture of 156.8 g of a 48.5 wt % NaOH aqueous solution and 238.3 g of ion-exchange water which was heated up to 40° C. The polypropylene container, covered with polystylene foam (heat insulating material), an internal diameter of 80 mm, and a capacity of 1 liter. As a result, a monomer aqueous solution (39 wt % of monomer concentration, 71.3 mol % of the neutralization ratio), whose temperature went up to about 100° C. because of heat of the neutralization and dissolution, was obtained. Further, 8.9 g of a 3 wt % sodium persulfate aqueous solution was added to the monomer aqueous solution and stirred for several seconds. Right after that, the aqueous solution thus stirred was poured in the open system into a stainless vat-type container, whose surface was heated up to 100° C. by, a hotplate (NEO HOTPLATE H1-1000, produced by Iuchi Seieido), in which Teflon (registered mark) film was applied to an inner surface, whose bottom surface was 250 mm×250 mm.

Polymerization started soon after the monomer aqueous solution was poured into the vat. The polymerization proceeded, as water vapor was generated and a gel expanded in all directions with foaming. Finally, the gel shrank and its size became a bit larger than the bottom surface. The expansion and shrinkage ended within about 1 minute. After kept in a polymerization container for 3 minutes, hydrate polymer was taken out.

The hydrate polymer, which was in a small-piece form, was spread on a 50-mesh metal net, and was dried by hot air of 180° C. for 40 minutes. The hydrate polymer thus dried was pulverized with a roll mill, and was classified with the JIS standard sieve whose mesh size was 600 µm. As a result, irregularly-shaped and pulverized water-absorbing resin, whose weight average diameter was 325 µm and whose logarithmic standard deviation (σζ) was 0.35, was obtained. CRCs of the water-absorbing resin obtained was 30.6 g/g, and SPGL was 42.8 kdyne/cm$^2$. The other properties were shown in Tables 12 and 13.

EXAMPLE 19-1

After 100 parts by weight of water-absorbing resin obtained in the Example 19 was mixed with a surface cross-linking agent made of a mixed liquid of 0.3 parts by weight of 1,4-butanediol, 0.6 parts by weight of propylene glycol, and 3 parts by weight of deionized water, a mixture was subjected to a heat treatment by which the mixture was kept at 190° C. for 35 minutes. Then, particles thus treated were disintegrated so that they passed through the JIS standard sieve whose mesh size was 600 µm. As a result, the water-absorbing resin whose surface was cross-linked was obtained. Table 12 shows properties of the water absorbent (19-1) obtained.

EXAMPLE 19-2

After 100 parts by weight of water-absorbing resin obtained in the Example 19 was mixed with a surface cross-linking agent made of a mixed liquid of 0.3 parts by weight of 1,4-butanediol, 1 part by weight propylene glycol, and 3 parts by weight of deionized water, a mixture was subjected to a heat treatment by which the mixture was kept at 190° C. for 40 minutes. Then, particles thus treated were disintegrated so that they passed through the JIS standard sieve whose mesh size was 600 µm. As a result, the water-absorbing resin whose surface was cross-linked was obtained. Table 12 shows properties of the water absorbent (19-2) obtained.

EXAMPLE 20

The operation was carried out in the same way described in the Example 15 except that 0.05 mol % polyethyleneglycol diacrylate was used. As a result, irregularly-shaped and pulverized water-absorbing resin, whose weight average diameter was 323 µm and whose logarithmic standard deviation (σζ) was 0.37, was obtained. CRCs of the water-absorbing resin obtained was 43.5 g/g, and SPGL was 35.1 kdyne/cm$^2$. The other properties were shown in Tables 12 and 13.

After 100 parts by weight of water-absorbing resin obtained was mixed with a surface cross-linking agent made of a mixed liquid of 0.5 parts by weight of 1,4-butanediol, 0.5 parts by weight of propylene glycol, and 4 parts by weight of deionized water, a mixture was subjected to a heat treatment by which the mixture was kept at 200° C. for 35 minutes. Then, particles thus treated were disintegrated so that they passed through the JIS standard sieve whose mesh size was 600 µm. As a result, the water-absorbing resin whose surface was cross-linked was obtained. Table 12 shows properties of the water absorbent (20) obtained.

(b) Addition of Liquid Permeability Improver

EXAMPLE 21

0.3 parts by weight of Reolosil QS-20 (hydrophilic amorphous silica, produced by TOKUYAMA) was thoroughly mixed with 100 parts by weight of water absorbent (13), obtained in the Example 13, in order to obtain a water absorbent. Tables 14 and 15 show properties of the water absorbent obtained.

EXAMPLE 22

0.3 parts by weight of Reolosil QS-20 (hydrophilic amorphous silica, produced by TOKUYAMA) was thoroughly mixed with 100 parts by weight of water absorbent (14-1), obtained in the Example 14-1, in order to obtain a water absorbent. Tables 14 and 15 show properties of the water absorbent obtained.

EXAMPLE 23

0.3 parts by weight of Reolosil QS-20 (hydrophilic amorphous silica, produced by TOKUYAMA) was thoroughly mixed with 100 parts by weight of water absorbent (14-2), obtained in the Example 14-2, in order to obtain a water absorbent. Tables 14 and 15 show properties of the water absorbent obtained.

EXAMPLE 24

0.7 parts by weight of aluminum sulfate 14-18 water (acquired from Wako Pure Chemical Industries, Ltd.) was thoroughly mixed with 100 parts by weight of water absorbent (14), obtained in the Example 14-2, in order to obtain a water absorbent. Tables 14 and 15 show properties of the water absorbent obtained.

EXAMPLE 25

0.3 parts by weight of Reolosil QS-20 (hydrophilic amorphous silica, produced by TOKUYAMA) was thoroughly mixed with 100 parts by weight of water absorbent (15), obtained in the Example 15, in order to obtain a water absorbent. Tables 14 and 15 show properties of the water absorbent obtained.

EXAMPLE 26

0.3 parts by weight of Reolosil QS-20 (hydrophilic amorphous silica, produced by TOKUYAMA) was thoroughly mixed with 100 parts by weight of water absorbent (16), obtained in the Example 16, in order to obtain a water absorbent. Tables 14 and 15 show properties of the water absorbent obtained.

EXAMPLE 27

0.3 parts by weight of Reolosil QS-20 (hydrophilic amorphous silica, produced by TOKUYAMA) was thoroughly mixed with 100 parts by weight of water absorbent (17), obtained in the Example 17, in order to obtain a water absorbent. Tables 14 and 15 show properties of the water absorbent obtained.

EXAMPLE 28

0.3 parts by weight of Reolosil QS-20 (hydrophilic amorphous silica, produced by TOKUYAMA) was thoroughly mixed with 100 parts by weight of water absorbent (18-1), obtained in the Example 18-1, in order to obtain a water absorbent. Tables 14 and 15 show properties of the water absorbent obtained.

EXAMPLE 29

0.3 parts by weight of Reolosil QS-20 (hydrophilic amorphous silica, produced by TOKUYAMA) was thoroughly mixed with 100 parts by weight of water absorbent (18-2), obtained in the Example 18-2, in order to obtain a water absorbent. Tables 14 and 15 show properties of the water absorbent obtained.

EXAMPLE 30

0.3 parts by weight of Reolosil QS-20 (hydrophilic amorphous silica, produced by TOKUYAMA) was thoroughly mixed with 100 parts by weight of water absorbent (19-1), obtained in the Example 19-1, in order to obtain a water absorbent. Tables 14 and 15 show properties of the water absorbent obtained.

EXAMPLE 31

0.3 parts by weight of Reolosil QS-20 (hydrophilic amorphous silica, produced by TOKUYAMA) was thoroughly mixed with 100 parts by weight of water absorbent (19-2), obtained in the Example 19-2, in order to obtain a water absorbent. Tables 14 and 15 show properties of the water absorbent obtained.

EXAMPLE 32

0.3 parts by weight of Reolosil QS-20 (hydrophilic amorphous silica, produced by TOKUYAMA) was thoroughly mixed with 100 parts by weight of water absorbent (20), obtained in the Example 20, in order to obtain a water absorbent. Tables 14 and 15 show properties of the water absorbent obtained.

(a) Polymerization and Surface Treatment

COMPARATIVE EXAMPLE 14

In a reactor vessel which was composed of a lid and a twin-arm type stainless kneader (content volume of 10 liters) jacketed and provided with two sigma blades, a reaction liquid was prepared by dissolving 11.7 g (0.10 mol %) of polyethyleneglycol diacrylate in 5438 g of a sodium acrylic acid aqueous solution (39 wt % of monomer concentration) having the neutralization ratio of 71.3 mol %. The reaction liquid was deaerated under a nitrogen gas atmosphere. Then, 29.34 g of a 10 wt % sodium persulfate aqueous solution and 24.45 g of a 0.1 wt % L-ascorbic acid aqueous solution were added to the reaction liquid with stirring. One minute later, polymerization started. The polymerization was carried out at a temperature of 20° C. to 95° C. while gels generated were crushed. After 30 minutes from the start of the polymerization, hydrate polymer was taken out.

Hydrogel cross-linked polymer (1) obtained was comminuted to have a diameter of less than or equal to about 5 mm. The hydrogel cross-linked polymer (1) thus comminuted was spread on a 50-mesh metal wire (mesh size: 300 μm), and was dried by hot air of 175° C. for 50 minutes. The polymer thus dried was pulverized with a roll mill. Next, the polymer thus crushed was classified with the JIS standard sieve whose mesh sizes was 850 μm. As a result, irregularly-shaped and pulverized water-absorbing resin, most of which have a particle diameter of 150 μm to 850 μm, whose weight average diameter was 323 μm, whose logarithmic standard deviation ($\sigma\zeta$) was 0.36, was obtained. CRCs of the water-absorbing resin obtained was 31.3 g/g, and SPGL was 33 kdyne/cm$^2$. The other properties were shown in Tables 12 and 13.

After 100 parts by weight of water-absorbing resin obtained was mixed with a surface cross-linking agent made of a mixed liquid of 0.3 parts by weight of 1,4-butanediol, 0.6 parts by weight propylene glycol, and 3 parts by weight of deionized water, a mixture was subjected to a heat treatment by which the mixture was kept at 195° C. for 30 minutes. Then, particles thus treated were disintegrated so that they passed through the JIS standard sieve whose mesh size was 600 μm. As a result, the water-absorbing resin whose surface was cross-linked was obtained. Table 14 shows properties of the comparative water absorbent (14) obtained.

COMPARATIVE EXAMPLE 15

An operation was carried out in the same way described in the Example 25 except that the water-absorbing resin had 278 μm in a weight average diameter and 0.49 in a logarithmic standard deviation ($\sigma\zeta$). In this way, the water-absorbing resin particles were obtained. (93.8 wt % of the particles was greater than or equal to 106 μm and less than 850 μm). CRCs of the water-absorbing resin obtained was 34.0 g/g, and SPGL was 37.6 kdyne/cm². The other properties were shown in Tables 12 and 13.

After 100 parts by weight of water-absorbing resin obtained was mixed with a surface cross-linking agent made of a mixed liquid of 0.3 parts by weight of 1,4-butanediol, 0.6 parts by weight of propylene glycol, and 3 parts by weight of deionized water, a mixture was subjected to a heat treatment by which the mixture was kept at 195° C. for 30 minutes. Then, particles thus treated were disintegrated so that they passed through the JIS standard sieve whose mesh size was 600 µm. As a result, the water-absorbing resin whose surface was cross-linked was obtained. Table 12 shows properties of the comparative water absorbent (15) obtained.

COMPARATIVE EXAMPLE 16

While a solution (A) was stirred in a polypropylene container by a magnetic stirrer, a solution (B) was poured at a stretch in an open system in order to mix the solutions (A) and (B). The solution (A) was a mixture of 194.35 g of acrylic acids and 0.58 g of polyethyleneglycol diacrylate (molecular weight 478). The solution (B) was a mixture of 166.7 g of a 48.5 wt % NaOH aqueous solution and 235.7 g of ion-exchange water which was heated up to 40° C. The polypropylene container, covered with polystyrene foam (heat insulating material), had an internal diameter of 80 mm, and a capacity of 1 liter. As a result, a monomer aqueous solution (40 wt % of monomer concentration, 75 mol % of the neutralization ratio), whose temperature went up to about 100° C. because of heat of the neutralization and dissolution, was obtained. Further, 2.70 g of a 10 wt % sodium persulfate aqueous solution was added to the monomer aqueous solution and stirred for several seconds. Right after that, the aqueous solution thus stirred was poured in the open system into a stainless vat-type container, whose surface was heated up to 100° C. by a hotplate (NEO HOTPLATE H1-1000, produced by Iuchi Seieido), in which Teflon (registered mark) film was applied to an inner surface, whose bottom surface was 250 mm×250 mm.

Polymerization started soon after the monomer aqueous solution was poured into the vat. The polymerization proceeded, as water vapor was generated and a gel expanded in all directions with foaming. Finally, the gel shrank and its size became a bit larger than the bottom surface. The expansion and shrinkage ended within about 1 minute. After kept in a polymerization container for 3 minutes, hydrate polymer was taken out.

The hydrate polymer, which was in a small-piece form, was spread on a 50-mesh metal net, and was dried by hot air of 170° C. for 40 minutes. The hydrate polymer thus dried was pulverized with a roll mill, and was classified with the JIS standard sieve whose mesh size was 600 µm. As a result, irregularly-shaped and pulverized water-absorbing resin, whose weight average diameter was 323 µm and whose logarithmic standard deviation (σζ) was 0.37, was obtained. CRCs of the water-absorbing resin obtained was 47.2 g/g, and SPGL was 32.2 kdyne/cm². The other properties were shown in Tables 12 and 13.

After the 100 parts by weight of water-absorbing resin obtained was mixed with a surface cross-linking agent made of a mixed liquid of 0.5 parts by weight of ethylene glycol diglycidyl ether, 1 part by weight of propylene glycol, and 2 parts by weight of deionized water, a mixture was subjected to a heat treatment by which the mixture was kept at 80° C. for 40 minutes. Then, particles thus treated were disintegrated so that they passed through the JIS standard sieve whose mesh size was 600 µm. As a result, the water-absorbing resin whose surface was cross-linked was obtained. Table 12 shows properties of the comparative water absorbent (16) obtained.

(b) Addition of Liquid-Permeability Improver

COMPARATIVE EXAMPLE 17

0.3 parts by weight of Reolosil QS-20 (hydrophilic amorphous silica, produced by TOKUYAMA) was thoroughly mixed with 100 parts by weight of comparative water absorbent (14), obtained in the Comparative Example 14, in order to obtain a water absorbent. Tables 14 and 15 show properties of the comparative water absorbent obtained.

COMPARATIVE EXAMPLE 18

1 part by weight of aluminum sulfate 14-18 water (acquired from Wako Pure Chemical Industries, Ltd.) was thoroughly mixed with 100 parts by weight of comparative water absorbent (14), obtained in the Comparative Example 14, in order to obtain a water absorbent. Tables and 15 show properties of the comparative water absorbent obtained.

COMPARATIVE EXAMPLE 19

0.3 parts by weight of Reolosil QS-20 (hydrophilic amorphous silica, produced by TOKUYAMA) was thoroughly mixed with 100 parts by weight of comparative water absorbent (15), obtained in the Comparative Example 15, in order to obtain a water absorbent. Tables and 15 show properties of the comparative water absorbent obtained.

COMPARATIVE EXAMPLE 20

0.3 parts by weight of Reolosil QS-20 (hydrophilic amorphous silica, produced by TOKUYAMA) was thoroughly mixed with 100 parts by weight of comparative water absorbent (16), obtained in the Comparative Example 16, in order to obtain a water absorbent. Tables and 15 show properties of the comparative water absorbent obtained.

TABLE 12

| | Conditions of Polymerization | | Properties of | | | | | | | | |
|---|---|---|---|---|---|---|---|---|---|---|---|
| | Peak | | Water-absorbing resin | | | | Properties of cross-linked water absorbent | | | | |
| | temperature [° C.] | Condensed ratio | CRCs [g/g] | SPGL(B) [kdyne/cm²] | D50 [µm] | σζ | CRCs [g/g] | AAPs [g/g] | SFC(A) [$10^{-7} \cdot cm^3 \cdot s \cdot g^{-1}$] | AAPdw [g/g] | Chemical cross-linked index against pressure |
| Ex. 13 | 108 | 1.32 | 34 | 37.6 | 323 | 0.36 | 26 | 24.5 | 81 | 82.8 | 108.8 |
| Ex. 14 | 109 | 1.30 | 30.2 | 41.4 | 328 | 0.36 | — | — | — | — | — |
| Ex. 14-1 | AS | AS | AS | AS | AS | AS | 27.2 | 24.6 | 46 | 85.9 | 113.1 |
| Ex. 14-2 | AS | AS | AS | AS | AS | AS | 26.3 | 24.4 | 57 | 83.6 | 109.9 |

TABLE 12-continued

|  | Conditions of Polymerization | | Properties of Water-absorbing resin | | | | Properties of cross-linked water absorbent | | | | |
| --- | --- | --- | --- | --- | --- | --- | --- | --- | --- | --- | --- |
|  | Peak temperature [° C.] | Condensed ratio | CRCs [g/g] | SPGL(B) [kdyne/cm$^2$] | D50 [μm] | σζ | CRCs [g/g] | AAPs [g/g] | SFC(A) [10$^{-7}$·cm$^3$·s·g$^{-1}$] | AAPdw [g/g] | Chemical cross-linked index against pressure |
| Ex. 15 | 110 | 1.32 | 31.4 | 40.1 | 325 | 0.35 | 26.1 | 24.1 | 65 | 81.7 | 107.8 |
| Ex. 16 | 112 | 1.36 | 32.4 | 35.2 | 312 | 0.40 | 26.2 | 25.1 | 58 | 81.9 | 108.1 |
| Ex. 17 | 109 | 1.32 | 34 | 35.7 | 327 | 0.34 | 26.1 | 23.8 | 70 | 83.4 | 109.5 |
| Ex. 18 | 109 | 1.30 | 32.6 | 44.2 | 321 | 0.36 | — | — | — | — | — |
| Ex. 18-1 | AS | AS | AS | AS | AS | AS | 27.4 | 24.8 | 52 | 90.8 | 118.2 |
| Ex. 18-2 | AS | AS | AS | AS | AS | AS | 26.5 | 24.8 | 68 | 89 | 115.5 |
| Ex. 19 | 111 | 1.31 | 30.6 | 42.8 | 325 | 0.35 | — | — | — | — | — |
| Ex. 19-1 | AS | AS | AS | AS | AS | AS | 27.3 | 24.2 | 43 | 88.5 | 115.8 |
| Ex. 19-2 | AS | AS | AS | AS | AS | AS | 26.7 | 24.7 | 52 | 88.4 | 115.1 |
| Ex. 20 | 110 | 1.31 | 43.5 | 35.1 | 323 | 0.37 | 35.1 | 26.9 | 3 | — | — |
| Com. Ex. 14 | 91 | 1.03 | 31.3 | 33.0 | 325 | 0.35 | 26.2 | 24.2 | 72 | 54.8 | 81.0 |
| Com. Ex. 15 | 108 | 1.32 | 34 | 37.6 | 278 | 0.49 | 25.8 | 23.7 | 38 | 67.8 | 93.6 |
| Com. Ex. 16 | 108 | 1.32 | 47.2 | 32.2 | 323 | 0.37 | 39.2 | 25.1 | 0 | — | — |

Abbreviation:
AS stands for "as above".
Ex. stands for Example
Com. Ex. stands for Comparative Example.

TABLE 13

|  | Above 850 μm | 850 μm~710 μm | 710 μm~600 μm | 600 μm~500 μm | 500 μm~425 μm | 425 μm~300 μm | 300 μm~212 μm | 212 μm~150 μm | 150 μm~106 μm | 106 μm~45 μm | Below 45 μm |
| --- | --- | --- | --- | --- | --- | --- | --- | --- | --- | --- | --- |
| Ex. 13 | 0.0 | 0.0 | 0.0 | 2.7 | 19.1 | 36.3 | 26.6 | 12.6 | 1.8 | 0.8 | 0.1 |
| Ex. 14 | 0.0 | 0.0 | 0.0 | 2.9 | 20.2 | 36.7 | 25.4 | 11.8 | 2.1 | 0.8 | 0.1 |
| Ex. 15 | 0.0 | 0.0 | 0.1 | 2.8 | 19.2 | 36.8 | 26.4 | 12.1 | 1.8 | 0.7 | 0.1 |
| Ex. 16 | 0.0 | 0.0 | 0.0 | 2.0 | 17.2 | 35.2 | 24.9 | 15.3 | 3.4 | 1.8 | 0.2 |
| Ex. 17 | 0.0 | 0.0 | 0.1 | 3.1 | 19.6 | 37.2 | 26.8 | 11.2 | 1.4 | 0.5 | 0.1 |
| Ex. 18 | 0.0 | 0.0 | 0.0 | 2.1 | 17.8 | 38.3 | 25.7 | 12.4 | 2.4 | 1.2 | 0.1 |
| Ex. 19 | 0.0 | 0.0 | 0.1 | 2.8 | 19.2 | 36.8 | 26.4 | 12.1 | 1.8 | 0.7 | 0.1 |
| Ex. 20 | 0.0 | 0.0 | 0.0 | 2.8 | 19.4 | 35.8 | 26.1 | 12.3 | 2.6 | 0.9 | 0.1 |
| Com. Ex. 14 | 0.0 | 0.0 | 0.1 | 2.8 | 19.2 | 36.8 | 26.4 | 12.1 | 1.8 | 0.7 | 0.1 |
| Com. Ex. 15 | 0.0 | 0.0 | 0.0 | 2.7 | 18.3 | 23.0 | 26.3 | 17.1 | 6.4 | 5.4 | 0.8 |
| Com. Ex. 16 | 0.0 | 0.0 | 0.0 | 2.6 | 19.4 | 36.2 | 25.5 | 13.2 | 2.0 | 1.0 | 0.1 |

Abbreviation:
Ex.: Example
Com. Ex.: Comparative Example

TABLE 14

|  | Water absorbent | Liquid-permeability improver | CRCs [g/g] | SFC(B) [10$^{-7}$·cm$^3$·s·g$^{-1}$] | AAPs [g/g] | SFC(B) − SFC(A) [10$^{-7}$·cm$^3$·s·g$^{-1}$] | IRS | AAPdw [g/g] | Chemical cross-linked index against pressure |
| --- | --- | --- | --- | --- | --- | --- | --- | --- | --- |
| Ex. 21 | Water absorbent (13) | Reolosil QS-20 | 26.0 | 192 | 22.1 | 111 | 4.57 | 75.2 | 101.2 |
| Ex. 22 | Water absorbent (14-1) | Reolosil QS-20 | 27.2 | 175 | 22.8 | 129 | 9.35 | 78.5 | 105.7 |
| Ex. 23 | Water absorbent (14-2) | Reolosil QS-20 | 25.8 | 210 | 22.2 | 153 | 8.95 | 76.4 | 102.2 |
| Ex. 24 | Water absorbent (14-2) | Aluminum sulfate 14-18 water | 26.5 | 198 | 24.3 | 141 | 3.53 | 76.8 | 103.3 |
| Ex. 25 | Water absorbent (15) | Reolosil QS-20 | 26.0 | 183 | 22.4 | 118 | 6.05 | 76.1 | 102.1 |
| Ex. 26 | Water absorbent (16) | Reolosil QS-20 | 26.2 | 154 | 23.0 | 96 | 5.52 | 74.5 | 100.7 |
| Ex. 27 | Water absorbent (17) | Reolosil QS-20 | 26.1 | 192 | 22.2 | 122 | 5.81 | 77.3 | 103.4 |
| Ex. 28 | Water absorbent (18-1) | Reolosil QS-20 | 27.1 | 174 | 23.9 | 122 | 7.82 | 85.3 | 112.4 |
| Ex. 29 | Water absorbent (18-2) | Reolosil QS-20 | 26.3 | 200 | 23.6 | 132 | 6.47 | 84.2 | 110.5 |
| Ex. 30 | Water absorbent (19-1) | Reolosil QS-20 | 27.2 | 163 | 23.3 | 120 | 9.30 | 81.0 | 108.2 |

TABLE 14-continued

| | Water absorbent | Liquid-permeability improver | CRCs [g/g] | SFC(B) [$10^{-7} \cdot cm^3 \cdot s \cdot g^{-1}$] | AAPs [g/g] | SFC(B) − SFC(A) [$10^{-7} \cdot cm^3 \cdot s \cdot g^{-1}$] | IRS | AAPdw [g/g] | Chemical cross-linked index against pressure |
|---|---|---|---|---|---|---|---|---|---|
| Ex. 31 | Water absorbent (19-2) | Reolosil QS-20 | 26.7 | 170 | 23.0 | 122 | 7.82 | 79.8 | 106.5 |
| Ex. 32 | Water absorbent (20) | Reolosil QS-20 | 34.8 | 12 | 23.6 | 9 | 10.0 | — | — |
| Com. Ex. 17 | Comparative water absorbent (14) | Reolosil QS-20 | 26.0 | 146 | 21.8 | 74 | 3.43 | 51.6 | 77.6 |
| Com. Ex. 18 | Comparative water absorbent (14) | aluminum sulfate 14-18 water | 25.9 | 147 | 22.2 | 75 | 1.04 | 52.1 | 78.0 |
| Com. Ex. 19 | Comparative water absorbent (15) | Reolosil QS-20 | 25.6 | 70 | 21.1 | 32 | 2.81 | 62.7 | 88.3 |
| Com. Ex. 20 | Comparative water absorbent (16) | Reolosil QS-20 | 39.0 | 3 | 23.2 | 3 | — | — | — |

Abbreviation:
Ex.: Example
Com. Ex.: Comparative Example

TABLE 15

| | Above 850 μm | 850 μm~710 μm | 710 μm~600 μm | 600 μm~500 μm | 500 μm~425 μm | 425 μm~300 μm | 300 μm~212 μm | 212 μm~150 μm | 150 μm~106 μm | 106 μm~45 μm | Below 45 μm | D50 [μm] | σζ |
|---|---|---|---|---|---|---|---|---|---|---|---|---|---|
| Ex. 21 | 0.0 | 0.0 | 0.0 | 3.0 | 20.5 | 39.8 | 24.5 | 10.5 | 1.2 | 0.4 | 0.1 | 335 | 0.33 |
| Ex. 22 | 0.0 | 0.0 | 0.0 | 3.2 | 24.2 | 40.2 | 21.8 | 9.1 | 1.1 | 0.3 | 0.1 | 349 | 0.32 |
| Ex. 23 | 0.0 | 0.0 | 0.0 | 3.1 | 23.4 | 38.9 | 23.8 | 8.7 | 1.5 | 0.5 | 0.1 | 343 | 0.32 |
| Ex. 24 | 0.0 | 0.0 | 0.0 | 3.0 | 23.2 | 38.5 | 23.6 | 9.2 | 1.7 | 0.7 | 0.1 | 341 | 0.33 |
| Ex. 25 | 0.0 | 0.0 | 0.0 | 3.0 | 20.7 | 37.5 | 27.0 | 10.3 | 1.0 | 0.4 | 0.1 | 331 | 0.33 |
| Ex. 26 | 0.0 | 0.0 | 0.1 | 2.9 | 19.4 | 37.1 | 25.5 | 12.3 | 1.7 | 0.9 | 0.1 | 326 | 0.36 |
| Ex. 27 | 0.0 | 0.0 | 0.0 | 3.3 | 20.4 | 39.8 | 25.7 | 9.6 | 0.8 | 0.3 | 0.1 | 336 | 0.32 |
| Ex. 28 | 0.0 | 0.0 | 0.0 | 2.5 | 19.2 | 40.2 | 26.1 | 10.0 | 1.2 | 0.7 | 0.1 | 331 | 0.33 |
| Ex. 29 | 0.0 | 0.0 | 0.0 | 2.3 | 18.6 | 38.9 | 26.5 | 11.4 | 1.4 | 0.8 | 0.1 | 326 | 0.34 |
| Ex. 30 | 0.0 | 0.0 | 0.0 | 3.0 | 21.2 | 38.9 | 27.1 | 8.4 | 0.9 | 0.4 | 0.1 | 336 | 0.32 |
| Ex. 31 | 0.0 | 0.0 | 0.0 | 2.9 | 20.9 | 37.9 | 26.8 | 9.8 | 1.1 | 0.5 | 0.1 | 332 | 0.33 |
| Ex. 32 | 0.0 | 0.0 | 0.0 | 3.2 | 21.1 | 36.2 | 25.7 | 11.6 | 1.5 | 0.6 | 0.1 | 330 | 0.35 |
| Com. Ex. 17 | 0.0 | 0.0 | 0.0 | 3.0 | 22.4 | 35.2 | 28.8 | 9.3 | 0.8 | 0.4 | 0.1 | 332 | 0.33 |
| Com. Ex. 18 | 0.0 | 0.0 | 0.0 | 2.9 | 22.1 | 36.1 | 28.2 | 9.2 | 0.9 | 0.5 | 0.1 | 332 | 0.33 |
| Com. Ex. 19 | 0.0 | 0.0 | 0.0 | 2.8 | 18.8 | 24.4 | 27.6 | 15.3 | 6.0 | 4.7 | 0.4 | 286 | 0.47 |
| Com. Ex. 20 | 0.0 | 0.0 | 0.0 | 2.4 | 20.1 | 37.2 | 26.1 | 12.1 | 1.5 | 0.5 | 0.1 | 327 | 0.35 |

Abbreviation:
Ex.: Example
Com. Ex. Comparative Example

TABLE 16

| Amount of cross-linking agent [mol %] | GV [g/g] | SPGL(A) [kdyne/cm$^2$] |
|---|---|---|
| 0.20 | 26.4 | 58.0 |
| 0.07 | 35.0 | 34.0 |
| 0.065 | 36.4 | 39.1 |
| 0.045 | 42.3 | 28.0 |
| 0.035 | 47.1 | 22.0 |
| 0.02 | 55.7 | 14.0 |

EXAMPLES 13-20, COMPARATIVE EXAMPLE 14

The water-absorbing resin obtained in the Examples 13-20 of the present invention had more than 35.0 kdyne/cm$^2$ in SPGL(B), and had high gel-stability when the water-absorbing resin was swelled. On the contrary, the water-absorbing resin obtained in the Comparative Example 14 did not have more than 35.0 kdyne/cm$^2$ in SPGL(B).

EXAMPLES 21-32, COMPARATIVE EXAMPLES 17-19

The water absorbent obtained in the Examples 21-32 of the present invention can be greatly improved in liquid-permeability by adding the liquid-permeability improver. Increasing rate of SFC per 1 wt % of the liquid-permeability improver used was more than 3.5 times. In case of producing the water absorbent having desired permeability, it is possible to reduce the amount of the liquid-permeability improver. On the contrary, the comparative water absorbent obtained in the Comparative Examples 17-19 did not have excellent liquid-permeability (SFC) or the increasing rate of SFC per 1 wt % of the liquid-permeability improver.

EXAMPLE 21, COMPARATIVE EXAMPLE 19

In the present invention, in order to obtain high permeability, it is important that the particles be distributed in a specific range (more than 95 wt % of the particles needed to be greater than or equal to 106 μm and less than 850 μm and the logarithmic standard deviation (σζ) of the particle size distribution needed to be 0.25-0.45). The comparative water absorbent of the Comparative Example 19 could not obtain excellent liquid-permeability because its weight average diameter and logarithmic standard deviation were inappropriate.

EXAMPLE 21, EXAMPLE 32

If the water-absorbing resin whose surface is not yet cross-linked has too high absorbency under no pressure (CRCs), the cross-linking agent is not enough and stability of a gel is essentially low to obtain high permeability in the present invention. In addition, SFC of the cross-linked water-absorbing resin is also low. Even if the water-absorbing resin includes the liquid-permeability improver, it is impossible to obtain desired permeability.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

According to the present invention, it is possible to provide a water absorbent having excellent gel properties, and showing excellent properties when used in a water-absorbing material of a sanitary/hygienic material such as paper diapers and the like. Moreover, the present invention provides a method of producing a water absorbent having excellent gel properties, and showing excellent properties when used in a water-absorbing material of a sanitary/hygienic material such as paper diapers and the like.

The water absorbent obtained by the method according to the present invention has a high gel stability when swelled, and an liquid permeability in the case it is used in the water-absorbing material such as diaper. Thus, the water-absorbing material having the water absorbent obtained by the method according to the present invention is very excellent because the water-absorbing material attains fast liquid absorption and a little residual amount of liquid on a surface of the water-absorbing material.

Moreover, the water absorbent obtained by the method according to the present invention makes it possible to reduce an amount of a liquid permeability improver (such as inorganic particles) used for attaining a target liquid dispersibility. Further, the water absorbent solves the problems in production thereof, and in production of the diaper such as foaming, dust problems (clogging of a filter). Furthermore, the water absorbent is more safe for consumers.

The invention claimed is:
1. A water absorbent, comprising:
water-absorbing resin particles, which are surface cross-linked and formed of a water-absorbing resin having a cross-linked structure prepared by polymerizing a monomer including 70 mol % to 100 mol % of an acrylic acid and a salt of the acrylic acid; and a liquid permeability improver (F), an additive amount of the liquid permeability improver (F) being 0.01 part by weight to 10 parts by weight with respect to 100 parts by weight of the water-absorbing resin particles, the liquid permeability improver (F) being selected from the group consisting of water-insoluble hydrophilic inorganic particles, water-soluble multivalent metal salt, a cationic polymer compound, and hydrophobic inorganic particles, the water absorbent satisfying the conditions that:
(a) 90% to 100% by weight of the water-absorbing resin particles have a diameter ranging from 150 μm to 850 μm;
(b) a logarithmic standard deviation (σζ) of a size distribution of the water-absorbing resin particles ranges from 0.25 to 0.45;
(c) AAPs for 0.9 wt % saline is at least 20 g/g;
(d) CRCs for 0.9 wt % saline ranges from 29 g/g to 39 g/g; and
(e) a chemical cross-linking index is at least 160, the chemical cross-linking index represented by Formula (1):

$$\text{Chemical Cross-Linking Index} = (CRCs)/(CRCdw) \times 1000 \qquad (1),$$

wherein CRCs (g/g) is an absorbency for 0.9 wt % saline, and CRCdw (g/g) is an absorbency for deionized water.

2. The water-absorbent of claim 1 wherein the chemical cross-linking index is at least 170.

3. The water absorbent of claim 1, further comprising phosphorus.

4. The water absorbent of claim 1, wherein the water absorbent has a Saline Flow Conductivity (SFC) ranging from 30 to 3000 ($10^{-7} \cdot cm^3 \cdot s \cdot g^{-1}$).

5. The water absorbent of claim 1, wherein the water absorbent has a Saline Flow Conductivity (SFC) ranging from 100 to 250 ($10^{-7} \cdot cm^3 \cdot s \cdot g^{-1}$).

6. The water absorbent of claim 3, wherein the phosphorous is derived from a phosphorous compound which is a water-soluble chain transfer agent.

7. The water absorbent of claim 6, wherein the water-soluble chain transfer agent is at least one selected from the group consisting of a hypophosphorous acid and its salt and a phosphorous acid and its salt.

8. The water absorbent of claim 1, wherein the liquid permeability improver (F) is the water-soluble multivalent metal salt.

9. The water absorbent of claim 8, wherein the water-soluble multivalent metal salt is an aluminum compound.

10. The water absorbent of claim 1, wherein:
the water-absorbing resin is prepared by polymerizing the monomer in the presence of 0.001 mol % to 10 mol % of a water-soluble chain transfer agent with respect to the monomer;
the water-absorbing resin, which has not yet been surface cross-linked, satisfies the following conditions (a) and (b), (a) at least 90% by weight of the water-absorbing resin particles have a diameter ranging from 150 μm to 850 μm; and
(b) a logarithmic standard deviation (σζ) of a size distribution of the water-absorbing resin particles ranges from 0.25 to 0.45; and
AAPs for 0.9 wt % saline of the water-absorbing resin particles which have been surface cross-linked is at least 20 g/g.

11. The water absorbent of claim 10, wherein the monomer is polymerized by boiling polymerization.

* * * * *